US012011475B2

(12) United States Patent
Wei et al.

(10) Patent No.: US 12,011,475 B2
(45) Date of Patent: Jun. 18, 2024

(54) POLYPEPTIDE, POLYPEPTIDE FRAGMENT, DERIVATIVE THEREOF, AND APPLICATIONS THEREOF

(71) Applicant: CHENGDU HUITAI BIOMEDICINE CO., LTD., Sichuan (CN)

(72) Inventors: De Wei, Sichuan (CN); Yi Ding, Sichuan (CN); Xiaomei Li, Sichuan (CN); Wen Yu, Sichuan (CN); Xiaohong Chen, Sichuan (CN); Ling Xiao, Sichuan (CN); Rui Chen, Sichuan (CN); Ling Chen, Sichuan (CN)

(73) Assignee: CHENGDU HUITAI BIOMEDICINE CO., LTD., Sichuan (CN)

( * ) Notice: Subject to any disclaimer, the term of this patent is extended or adjusted under 35 U.S.C. 154(b) by 737 days.

(21) Appl. No.: 16/490,543

(22) PCT Filed: Feb. 28, 2018

(86) PCT No.: PCT/CN2018/077492
§ 371 (c)(1),
(2) Date: Sep. 1, 2019

(87) PCT Pub. No.: WO2018/157807
PCT Pub. Date: Sep. 7, 2018

(65) Prior Publication Data
US 2022/0072082 A1 Mar. 10, 2022

(30) Foreign Application Priority Data

Mar. 1, 2017 (CN) .......................... 201710115604.4
Aug. 9, 2017 (CN) .......................... 201710677602.4

(51) Int. Cl.
*A61K 38/04* (2006.01)
*A61P 43/00* (2006.01)

(52) U.S. Cl.
CPC .............. *A61K 38/04* (2013.01); *A61P 43/00* (2018.01)

(58) Field of Classification Search
None
See application file for complete search history.

(56) References Cited

U.S. PATENT DOCUMENTS

| 6,090,367 A * | 7/2000 | Khalil ..................... A61P 11/00 424/45 |
| 2006/0270618 A1 | 11/2006 | Bevec |
| 2008/0194486 A1 | 8/2008 | Bridon et al. |
| 2010/0286028 A1 | 11/2010 | Bevec |
| 2012/0315282 A1 | 12/2012 | Bedinger |

FOREIGN PATENT DOCUMENTS

| CN | 1620309 A | 5/2005 |
| CN | 103732623 A | 4/2014 |
| CN | 104313028 A | 1/2015 |
| CN | 105061600 A | 11/2015 |
| CN | 106860855 A | 6/2017 |
| JP | 2010168384 A | 8/2010 |
| WO | 9636349 A1 | 11/1996 |
| WO | 2009043525 A2 | 4/2009 |
| WO | 2016054114 A1 | 4/2016 |

OTHER PUBLICATIONS

The Canadian 3rd Office Action dated Jun. 30, 2022 for Canadian Application No. CA3054839.
The 1st Office Action regarding Chinese Patent Application No. CN201710115604.4, dated Apr. 28, 2020. English Translation Provided by http://globaldossier.uspto.gov.
Ying Chen, A TSP-1 synthetic peptide inhibits bleomycin-induced lung fibrosis in mice, Experimental and Toxicologic Pathology 61(1):59-65, Jun. 24, 2008.
Wang Xin, Study of Fibrosis Inhibition in Silicotic Mice by CD36 Synthetic Peptide, Ind Hlth & Occup Dis, Jan. 20, 2010, vol. 36 , No. 1, pp. 32-35.
International Search Report for PCT/CN2018/077492 dated May 30, 2018, ISA/CN.
Leung et al., "CD36 Peptides Enhance or Inhibit CD36-Thrombospondin Binding", The Journal of Biological Chemistry, 267(25), pp. 18244-18250,Sep. 5, 1992.
Wang et al., "A CD36 synthetic peptide inhibits silica-induced lung fibrosis in the mice", Toxicology and Industrial Health, 26(1), pp. 47-53, Jan. 7, 2010.
The Canadian 1st Office Action dated Sep. 18, 2020 for Canadian Application No. CA3054839.
The Australian 1st Office Action dated Sep. 10, 2020 for Australian Application No. AU2018227737.
The Extended European Search Report dated Dec. 8, 2020 for European Application No. EP18760361.8.
Cui Wenpeng et al: "Interaction of thrombospondinl and CD36 contributes to obesity-associated podocytopathy", Biochimica et Biophysica Acta. Molecular Basis of Disease, Amsterdam, NL,vol. 1852, No. 7, Mar. 31, 2015 (Mar. 31, 2015), pp. 1323-1333.
Yehualaeshet Teshome et al: "A CD36 synthetic peptide inhibits bleomycin-induced pulmonary inflammation and connective tissue synthesis in the rat", American Journal of Respiratory Cell and Molecular Biology, American Lung Association, New York, NY, US,vol. 23, No. 2, Aug. 1, 2000 (Aug. 1, 2000), pp. 204-212.
Wang Xin et al: "Silencing CD36 gene expression results in the inhibition of latent-TGF-β1 activation and suppression of silica-induced lung fibrosis in the rat". Respiratory Research, Biomed Central Ltd., London, GB, vol. 10, No. 1, May 13, 2009 (May 13, 2009), p. 36.

(Continued)

*Primary Examiner* — Maury A Audet
(74) *Attorney, Agent, or Firm* — Yue (Robert Xu; Apex Attorneys at Law, LLP

(57) ABSTRACT

Disclosed in the present invention are a polypeptide fragment, a derivative of the polypeptide fragment, and applications of the derivative of the polypeptide in the preparation of drugs for preventing and treating fibrosis diseases.

6 Claims, 20 Drawing Sheets

Specification includes a Sequence Listing.

(56) References Cited

OTHER PUBLICATIONS

Fengyun Xu et al.: "TGF-β/SMAD Pathway and Its Regulation in Hepatic Fibrosis", Journal of Histochemistry and Cytochemistry, vol. 64, No. 3, Mar. 8, 2016 (Mar. 8, 2016), pp. 157-167.
Wayne A.Border,M.D., Transforming Growth Factor β in Tissue Fibrosis, The New England Journal of Medicine, vol. 331, No. 19, pp. 1286-1292, Nov. 10, 1994.
Isabel Fabregat et al., TGF-b signalling and liver disease, The FEBS Journal (2016) ,Federation of European Biochemical Societies, State-Of-The-Art Review, Received Dec. 3, 2015, revised Dec. 29, 2015, accepted Jan. 20, 2016, pp. 1-14.
Katrin Palumbo-Zerr et al., Orphan nuclear receptor NR4A1 regulates transforming growth factor-β signaling and fibrosis, Articles, vol. 21 | No. 2 | Feb. 2015 nature medicine, pp. 150-160.
Xiao-ming Meng et al., TGF-β: the master regulator of fibrosis, Nature Reviews | Nephrology, Reviews, vol. 12 | Jun. 2016 | pp. 325-338.https://www.nature.com/nrneph/.
Archana Agarwal et al., Bone marrow fibrosis in primary myelofibrosis: pathogenic mechanisms and the role of TGF-β, Stem Cell Investigation 2016;3:5, pp. 1-10.
Rudolf Fuchshofer & Ernst R. Tamm, The role of TGF-β in the pathogenesis of primary open-angle glaucoma, Cell Tissue Res (2012) 347:279-290, DOI 10.1007/s00441-011-1274-7.
Shizuya Saika1 et al., TGFβ in fibroproliferative diseases in the eye, Frontiers in Bioscience S1, 376-390, Jun. 1, 2009, pp. 376-390. Frontiers in Bioscience S1, 376-390, Jun. 1, 2009.
J. F. Santibanez, M. Quintanilla and C. Bernabeu, TGF-β/TGF-β receptor system and its role in physiological and pathological conditions, Clinical Science (2011) 121, 233-251 (Printed in Great Britain) doi:10.1042/CS20110086.

\* cited by examiner

POLYPEPTIDE, POLYPEPTIDE FRAGMENT, DERIVATIVE THEREOF, AND APPLICATIONS THEREOF

CROSS REFERENCE TO RELATED APPLICATIONS

This application is the national stage entry of PCT application PCT/CN2018/077492, filed on Feb. 28, 2018, with China Patent Office, titled "POLYPEPTIDE, POLYPEPTIDE FRAGMENT, DERIVATIVE THEREOF, AND APPLICATIONS THEREOF", which claims the priority of Chinese Patent Application No. 201710115604.4, filed on Mar. 1, 2017, filed with China Patent Office and titled with "POLYPEPTIDE, DERIVATIVE THEREOF, AND APPLICATIONS IN PREVENTION AND TREATMENT OF FIBROSIS DISEASES THEREOF", and the priority of Chinese Patent Application No. 201710677602.4, filed on Aug. 9, 2017, filed with China Patent Office and titled with "POLYPEPTIDE, POLYPEPTIDE FRAGMENT, DERIVATIVE THEREOF, AND APPLICATIONS IN PREVENTION AND TREATMENT OF FIBROSIS DISEASES THEREOF", and the disclosures of which are hereby incorporated by reference.

SEQUENCE LISTING

Sequence Listing is being submitted as an ASCII text file via EFS-Web, file name "190090-APXU-HUITAI-Amended-Sequence-Listing.txt", size 14,970 bytes, created on Dec. 2, 2019, the content of which is incorporated herein by reference.

FIELD

The present invention belongs to the field of medical technology, relates to the field of prevention and treatment of fibrosis diseases, and specifically relates to a polypeptide, a polypeptide fragment and a derivative thereof, and applications in the preparation of medicaments for prevention and/or treatment of fibrosis diseases.

BACKGROUND

Protein is a material basis of the organism and a main bearer of life activities, involving physiological processes such as growth, development, immune regulation, and metabolism. Protein and signal transduction abnormalities in which it involved are root causes of the occurrence and development of diseases. The use of the body's own regulation to control disease is the essential thought of biomedicine. Therefore, protein is both a source of drug targets and an important class of biopharmaceuticals, and protein functional fragments provide a guarantee for precision drug use. Polypeptides are active fragments of proteins that function. When studies find that the activity of polypeptide fragments is associated with disease, these active polypeptides can be used to develop drugs with clinical application value. The study of protein functional fragments provides a theoretical basis for treatment of diseases, and also provides a broader space for the development of polypeptide drugs based on protein functional fragments.

Polypeptide drugs have obvious advantages in the field of drug research and development: compared with general organic small molecule drugs, polypeptide drugs have outstanding advantages such as high activity, small doses, and low toxicity and side effects; while compared with protein drugs, small polypeptides are relatively less immunogenic and can be chemically synthesized, with high purity and controllable quality. Most of the current polypeptide drugs originate from or mimic endogenous peptides or other natural peptides. The structure is clear and the mechanism of action is definite, the metabolites are amino acids, which do not accumulate in the body, and the toxicity and side effects are low. Currently, with the development of polypeptide synthesis technology, the production, process and purity problems of polypeptides have been effectively solved. In addition, by further studying the structure-activity relationship of the active polypeptide, the shortest fragment necessary for the biological activity of the polypeptide are discovered so that shorter polypeptides can be used as replacements; or the amino acid substitution can be used to increase its biological activity or change its clinical adverse reaction, so that small fragments of polypeptides have better biocompatibility, reduce clinical adverse reactions, and can delay the rate of enzymatic hydrolysis by replacing amino acids which are easily digested in the peptide chain, so that the half-life of the polypeptide drugs is effectively extended.

However, the polypeptide itself still has some disadvantages, such as the polypeptide is easily hydrolyzed by enzymes, the half-life is short, and the bioavailability is low. In order to solve the problem of polypeptide application in preparation of drugs, in addition to changing the route of administration of polypeptide drugs, chemical modification has become a very important research direction in the research and development of polypeptide drugs, which is one of the important technical means for realizing long-acting effects and extending the half-life of protein polypeptide molecules. According to the characteristics of polypeptide drugs, various means are used to carry out structural design and chemical modification to modify the molecular structure of the polypeptide drugs, using suitable modification methods and modifiers to chemically modify the main chain structure or the side chain group of the protein polypeptide drugs can change its molecular size as well as charge and receptor binding ability, improve fat solubility. And at the same time the steric hindrance formed by the modified group protects the region likely to be attacked by proteolytic enzymes, delays the degradation of the active protein, improves the stability of the drug, and finally changes the physicochemical properties and pharmacokinetics of the polypeptides, and fully exploits the advantages of the polypeptide drugs, overcome or even avoid its disadvantages.

Currently known polypeptide modification methods include acetylation modification, amidation modification, glycosylation modification, polyethylene glycol (PEG) modification, fatty acid modification, phosphorylation modification, etc. The main chain end modification methods commonly used in polypeptide drugs are amino (N) terminal acetylation and carboxyl (C) terminal amidation modification, respectively protecting the amino and carboxyl groups at the ends of the peptide chain. The basic principle is to increase the relative molecular weight and steric hindrance of the polypeptide molecule, continue or inhibit the action of the polypeptide proteolytic enzymes, improve the stability of the polypeptide drugs and reduce the filtration effect of the glomerulus. Glycosylation modification is the binding of a monosaccharide, oligosaccharide or polysaccharide structure to a functional group on a side chain of certain special amino acids in a polypeptide chain, for example, N-glycosylation is an binding of the amide nitrogen of the side chain by asparagine; O-glycosylation is an binding to the oxygen on serine or threonine residues. Glycosylation can increase the steric hindrance of the side chain and increase the stability of polypeptides against enzymes. For example, erythropoietin (EPO), which is used to treat chronic kidney failure and anemia, the frequency of use of glycosylation-modified EPO can be reduced from 2 to 3 times a week to once a week or once every 2 weeks. The PEG modification is obtaining a modified product by covalently linking different PEG modifiers to a functional group such as an amino group or a carboxyl group of a polypeptide main chain or a side chain, an imidazolyl group, a sulfhydryl group or a hydroxyl group of a side chain. PEG itself is a macromolecular polymer polymerized by ethylene oxide, which has different structures and different molecular weights and can be degraded in vivo. It is non-toxic, non-antigenic, and has the advantages of relatively high hydrophilicity and biocompatibility and a wide range of relative molecular choices. The solubility of the PEG-modified polypeptide drug increases significantly, the release in vivo is slow, the half-life is extended, and steric hindrance can be formed, the immune response is reduced, and the proteolysis is inhibited. PEG is currently the most commonly used modifier. There are more PEG-modified proteins or polypeptide drugs in research or market compared with other modification methods. The world's first PEG-modified protein drug, PEG-adenosine deaminase, was approved by the FDA in 1991, there are also PEG-modified asparaginase, colony-stimulating growth factor, interferon alpha, etc. Fatty acid modification is the modification covalently linking fatty acid structure to certain special functional groups in protein polypeptide molecules, including modifications of an amino group, a carboxyl group a sulfhydryl group, a hydroxyl group, etc. Fatty acid is a component constituting cell membrane phospholipids and human body fats and lipoids. Therefore, fatty acid modification can effectively improve the liposolubility and absorption of polypeptide drugs, block the region where polypeptide molecules are likely to be degraded by enzymes, delay or inhibit proteolysis; fatty acids also enhance the binding of polypeptide drugs to plasma albumin to form relatively large complexes to extend the drug's residence time in the body. Such as Liraglutide (Novo Nordisk), one of the fatty acid modified polypeptide drugs in market used to treat type 2 diabetes, replaces lysine (Lys) at position 34 of human GLP-1 with arginine (Arg) and introduce a glutamic acid (Glu)-mediated 16-carbon palmitic acid side chain at the Lys at position 26, which significantly reduces the adverse reactions of GLP-1 while completely retains its biological activity.

In actual clinical applications, the chemically modified polypeptide drugs as described above have been shown to have significant advantages, which can significantly extend the half-life of the polypeptide drugs, improve the efficacy of the drugs, reduce the frequency of administration, and thereby bringing good therapeutic compliance. Polypeptide modification types and modification methods will continue to develop, and the ultimate goal is to enable polypeptide drugs to move from laboratory research to safe and effective clinical applications.

The present disclosure is based on the development of polypeptide drug technology in biomedical field, and provides a use of a kind of chemically modified derivatives of polypeptide in the preparation of medicaments in prevention and treatment of fibrosis diseases having complicated mechanism and being difficult to be treated.

Fibrosis is an excessive deposition and remodeling disorder of fibrous connective tissue caused by an increase in extracellular matrix such as collagen and fibronectin at the site of injury or inflammatory lesions and surrounding areas, causing permanent scars, organ dysfunction and even death. Fibrosis is closely related to the occurrence of various diseases. This common clinical pathological change is the final pathological outcome of common chronic inflammatory diseases, and is also the main pathological symptom of chronic autoimmune diseases. It can also affect tumor invasion and metastasis and chronic graft rejection. Fibrosis can occur in a variety of tissues and organs, especially in important functional organs (the liver, lung, kidney and heart), often irreversibly and progressively aggravate, severely destroy organ structure, and ultimately lead to organ dysfunction and to failure and thereby greatly reducing the quality of life of patients and seriously threatens human health. Statistics show that 45% of people who die from various diseases can be attributed to fibrosis.

Despite the high incidence and mortality of fibrosis diseases, it is currently mainly focused on non-pharmacological treatments such as prevention and organ transplantation, and other drugs are used as adjuvant therapies, and even palliative treatments. There are very few specific drugs for treatment of fibrosis diseases, which are far from meeting the clinically effective and safe needs. For example, Marfan syndrome, a hereditary connective tissue disease caused by mutations in autosomal gene encoding glycoprotein microfibrin (FBN1). The patient's limbs are slender and uneven, accompanied by abnormalities of the cardiovascular system, and important tissues and organs involvement, such as bones, nervous system, skin and eyes. Most of the patients die from aortic aneurysm rupture and heart failure and can only survive to middle age, but there are currently no drug available worldwide for the treatment of Marfan syndrome.

Another type of connective tissue disease characterized by localized or diffuse skin thickening and fibrosis, involving the heart, lung, kidney, digestive tract and other internal organs, is called systemic sclerosis (SSc). According to relevant statistics, there are about 2 million patients with systemic sclerosis in the world, which often develop slowly but have a poor prognosis. As much as 90% of the patients may have different degrees of lung scars, accounting for about 35% of deaths. There is currently only one drug for treatment in the world: Nintedanib (Boehringer Ingelheim), which was approved in 2016 by the European Commission and the FDA's orphan drug certification fast track. Nintedanib is only a symptomatic treatment of systemic sclerosis-associated interstitial lung disease (S Sc-ILD), its clinical efficacy after marketing remains to be evaluated. However, systemic sclerosis is a new indication in the development of Nintedanib. Initially, Nintedanib was a drug used to treat one of the most severe pulmonary fibrosis diseases: idiopathic pulmonary fibrosis (IPF).

Idiopathic pulmonary fibrosis is a chronic, progressive, fibrotic interstitial lung disease with an unknown cause, and is also called a tumor-like disease. It is often accompanied by acute exacerbation. The average survival after diagnosis is only 2.8 years, and the mortality rate is higher than all tumor diseases except lung cancer. Currently, the drugs for the treatment of idiopathic pulmonary fibrosis worldwide are Pirfenidone (Roche) and Nintedanib, which are orphan drugs entered the market through the FDA rapid approval channel in 2014, and also the two types of drugs received the highest recommendations (conditional recommendations) in the Clinical Practice Guideline: Treatment of Idiopathic Pulmonary Fibrosis published by American Thoracic Society/European Respiratory Society/Japanese Respiratory Society/Latin American Thoracic Association. Wherein, Pirfenidone is an anti-fibrotic, anti-inflammatory and antioxidant compound, of which the exact mechanism of action is not fully understood yet. Nintedanib is a multi-tyrosine kinase inhibitor that acts on three important cytokine receptors that regulate the fibrotic signaling pathway: fibroblast growth factor receptor (FGFR), platelet-derived growth factor receptor (PDGFR), and vascular endothelial growth factor receptor (VEGFR). Nintedanib can specifically bind to the ATP binding site on the receptor, preventing the activation of phosphorylation of the receptor, thereby blocking signaling pathway transduction it mediated. The emergence of Pirfenidone and Nintedanib has filled a gap in the field of pulmonary fibrosis treatment. However, Global Data analysis (2016) believes that these two drugs are only used to delay the decline of lung function in patients, and are not effective drugs to interrupt the progression of lung disease. Clinical studies have also shown that there is no significant improvement in mortality and far from meeting the needs of pulmonary fibrosis treatment. In addition, since both drugs are small molecule compounds, they are not suitable for pregnant women or patients with liver problems, a large oral dose is required to achieve an effective lung drug concentration, and there is a significant adverse gastrointestinal reaction. Pirfenidone also causes severe photosensitivity and rash, and patient compliance is poor in clinical use.

In addition to the above-mentioned three indications, fibrosis diseases also involve other important organs such as the liver, kidney, heart and eyes. Patients with fibrosis diseases often have organ and tissue involvements. In the absence of a drug that effectively delays or blocks the progression of fibrotic lesions, the ultimate treatment option is limited to organ transplants with difficulties in donors, relatively high risks and expense, which also brings a very heavy social and economic burden. However, the clinical treatment effect and safety of available drugs cannot meet the treatment needs, and the number of confirmed cases of fibrosis diseases will still increase in the future. Therefore, it is urgent to further study the mechanism of action of fibrosis diseases, fully integrate the innovative medical development trend, and develop new therapeutic drugs that can effectively block fibrosis diseases and are safe for clinical use.

Fibrosis is a pathological process that gradually progresses from inflammation to fibrosis caused by repetitive or relatively severe damage, and generally the pathogenesis can be divided into three stages. The first stage is an injury stage and hemostasis stage. The epithelial or endothelial cell damage, which is caused by infection, toxin, drug, trauma, etc., triggers the coagulation reaction. The platelets in the circulating blood are activated by contacting with the collagen fibers exposed to the damaged blood vessels, releasing platelet factors and forming fibrin clots to ensure rapid hemostasis. The activated platelets simultaneously release a variety of cytokines such as platelet-derived growth factor (PDGF), chemokine, and transforming growth factor beta (TGF-beta). The second stage is an inflammation and proliferation stage, i.e., a stage of regeneration. Mediated by chemokines, the inflammatory cells chemotaxis and aggregate to the site of injury, bone marrow stem cells are activated into inflammatory cells, such as macrophages and neutrophils, and secrete various cytokines (such as IL-13, IL-17, TGF-β, etc.) to promote immune repair and inflammation. Epithelial and innate immune cell-derived cytokines can activate specific immune responses that further promote inflammation and immune repair. Inflammation and immune mediators (cytokines, chemokines, free radicals, etc.) activate resting fibroblasts, stimulate collagen synthesis in the extracellular matrix, and promote their differentiation into myofibroblasts. The third stage is a maturity stage, i.e. tissue remodeling or fibrosis. The normal condition is final angiogenesis, wound contraction, tissue regeneration. But when harmful stimuli persist, the inflammatory response and chronic healing reaction are intensified, and the tissue damage-repair-regeneration reaction is repeated, and the myofibroblasts are continuously activated, more extracellular matrix are secreted and deposition occurs, which eventually leads to tissue thickening, remodeling disorder, and fibrosis formation.

The mechanism of fibrosis occurrence is complicated, which involves inflammatory response, oxidative stress, immune responses, and fibrosis occurrence-related varieties of cytokines and signaling pathway mediated by them. Cytokines that play a major role include IL-1β, TNF-α, IL-13, PDGF and TGF-β. Wherein IL-1β can indirectly promote or directly regulate extracellular collagen synthesis by binding to the extracellular matrix to activate TGF-β precursor, and promote fibroblast differentiation into myofibroblast, and also can regulate extracellular matrix synthesis in fibroblasts via FAK/rac1/NOX/ROS signaling pathway, and promote fibrosis occurrence by binding to connective tissue growth factor CCN2. Both TNF-α and IL-1β are inflammation promoting regulators, which can aggravate parenchymal cell damages and induce epithelial-mesenchymal transition and myofibroblast activation via TGF-β signaling pathway. TNF-α and IL-1β can also promote the activity of the autocrine growth factor IL-6 in fibroblasts. IL-13 is a cytokine secreted by type 2 helper T cells (Th2 cell), which can promote fibroblast proliferation through integrin β1, IL-6 and chemokine MCP-1. The Th2 cell expressing IL-β can also stimulate secretion of TGF-β precursor by macrophages, and then IL-β activates TGF-β via a related proteolytic pathway such as metalloproteinase and cathepsin. PDGF is a fibroblast mitogen that produces more myofibroblasts by stimulating fibroblast proliferation, migration, and transformation, and at the same time stimulate collagen synthesis. TGF-β can directly induce fibroblast differentiation into myofibroblasts, promote collagen expression and deposition, while myofibroblasts secreting extracellular matrix are the final result of all fibrosis diseases.

The above-mentioned cytokines can be secreted by various types of cells, or can indirectly regulate through inflammatory responses and immune responses, or directly activate the TGF-β signaling pathway to promote fibrosis occurrence. Therefore, TGF-β is believed to be the most critical cytokine in the regulation of fibrosis. A large number of reports have confirmed that fibrosis diseases are closely related to the abnormal regulation of the cytokine TGF-β and its downstream signaling pathway. Publicly reported fibrosis diseases associated with the TGF-β signaling pathway include rheumatoid arthritis, pulmonary fibrosis, hepatic fibrosis, cirrhosis, renal fibrosis, myelofibrosis, cystic fibrosis, myocardial fibrosis, scleroderma, sarcoidosis, keloids, burn-induced hypertrophic scars, proliferative retinopathy, glaucoma, cataract, posterior capsule opacification, vascular restenosis after angioplasty, vascular surgery or vascular injury, Marfan syndrome, etc. Studies have shown that inhibition of TGF-β signaling pathway can delay the progression of fibrosis in animal models of multiple diseases.

With in-depth study of the mechanisms related to fibrosis diseases in the past 30 years, based on the molecular mechanisms of multiple cytokines and their activated intracellular signaling pathways involved in fibrosis occurrence, the main nodes in these pathways have become the main target for the drugs for prevention and treatment of fibrosis on a global scale. Since fibrosis involves many cytokines, finding the most effective target factor is the key to the treatment of fibrosis diseases. In view of the important role of TGF-β signaling pathway in fibrosis diseases, using TGF-β signaling pathway as a drug target is expected to be an ideal drug for blocking fibrosis diseases.

Mammalian TGF-β includes three subtypes, TGF-β1, TGF-β2 and TGF-β3, respectively. Wherein TGF-α1 is the most abundant and widely distributed subtype in tissues, and is also the most important factor promoting tissue fibrosis. TGF-β1 is produced in vivo as an inactive precursor protein (Pre-pro-TGF-β1), and it can only release biologically active TGF-β1 after a series of enzymatic and conformational changes, and promote fibrosis occurrence mainly by activating downstream signaling pathways of Smad family proteins. Based on its signal activation and transduction mechanism, using peptide synthesis technology to prepare or mimic the key sequences required for TGF-β1 to function to block TGF-β1 secretion, activation and signal transduction can suppress the most critical fibrosis regulatory signaling pathway from key nodes, and thereby effectively inhibiting the occurrence and development of fibrotic pathological processes.

Studies have shown that under experimental conditions, the peptides KRFK, CSVTCG, YRVRFLAKENVTQ-DAEDN and CNLAVAAASHIYQNQFVQ can inhibit the transduction of TGF-β signaling pathway, thereby delaying the progression of fibrosis. However, in the actual application process, the polypeptide has the problems of low solubility and poor stability, which greatly affects the druggability of the polypeptide, and there is still a need for a higher improvement in its physicochemical properties in the preparation of drugs for prevention and treatment of fibrosis diseases. The present disclosure is based on the above, performing amino acid deletion, substitution and addition based on one of the polypeptide sequences to discover the most effective active fragment, and performing chemical modification based on the above to improve the solubility of the polypeptide, increase the stability of the polypeptide and extending its half-life, improve biological activity, reduce toxic side effects, to enhance the druggability the polypeptide, and ultimately apply to the preparation of clinically safe and effective drugs for prevention and treatment of fibrosis diseases.

SUMMARY

In view of the current lack of clinically effective and safe drugs for prevention and treatment of fibrosis diseases, the present disclosure provides a polypeptide, a polypeptide fragment, a polypeptide fragment derivative, a polypeptide derivative, and a use of a polypeptide derivative having a chemical modification in the above-mentioned polypeptide, polypeptide fragment and its derivative for the manufacture of a medicament in prevention or treatment of a fibrosis disease.

The polypeptide of the present disclosure is a compound composed of amino acids linked by a peptide bond, which is a product wherein the number of amino acids is not limited.

The polypeptide SEQ ID NO: 1 of the present disclosure can inhibit the transduction of TGF-β signaling pathway, reduce the infiltration of inflammatory cells and reduce the synthesis of extracellular matrix proteins, thereby inhibiting inflammation and fibrosis reactions to achieve the purpose of preventing and treating fibrosis diseases.

Performing amino acid deletion, addition, substitution or modification in the polypeptide SEQ ID NO: 1 of the present disclosure is to make it suitable for use for the manufacture of a medicament in prevention or treatment of fibrosis diseases.

The polypeptide provided by the present disclosure is a polypeptide having an amino acid deletion, substitution, addition and/or modification in the polypeptide sequence set forth in SEQ ID NO: 1. It may be a polypeptide which has an amino acid deletion, substitution, addition or modification in the polypeptide sequence set forth in SEQ ID NO: 1. It may also be a polypeptide simultaneously having at least two of deletion, substitution, addition or modification in the polypeptide sequence set forth in SEQ ID NO: 1, such as simultaneously having a deletion and a substitution, simultaneously having a deletion and an addition, simultaneously having a deletion and a modification, simultaneously having a substitution and an addition, simultaneously having a substitution and a modification, simultaneously having an addition and a modification, simultaneously having a deletion, a substitution and a modification, simultaneously having a deletion, an addition and a modification, simultaneously having a substitution, an addition and a modification. It may also be a polypeptide simultaneously having a deletion, a substitution, an addition and a modification.

In some embodiments, the polypeptide respectively has a deletion, substitution or addition of one or more amino acids in the polypeptide sequence set forth in SEQ ID NO: 1.

In some embodiments, the polypeptide simultaneously has a deletion, substitution or addition of one or more amino acids in the polypeptide sequence set forth in SEQ ID NO: 1.

The number of the amino acid of the deletion of the present disclosure is within 7, including 7. That is, the number of the amino acid of the deletion is 1, 2, 3, 4, 5, 6 or 7.

The number of the amino acid of the substitution of the present disclosure is no more than 11, including 11. That is, the number of the amino acid of the substitution is 1, 2, 3, 4, 5, 6, 7, 8, 9, 10 or 11.

The number of the amino acid of the addition of the present disclosure is no more than 8, including 8. That is, the number of the amino acid of the deletion is 1, 2, 3, 4, 5, 6, 7 or 8.

In some embodiments, the polypeptide is selected from the group consisting of polypeptides set forth in SEQ ID NO: 4, SEQ ID NO: 5, SEQ ID NO: 6, SEQ ID NO: 7 and SEQ ID NO: 8.

In some embodiments, the polypeptide has a modification in the polypeptide sequence set forth in SEQ ID NO: 1.

Wherein the modification includes polyethylene glycol modification, fatty acid modification, glycosylation modification, acetylation modifications, amidation modification, phosphorylation modification and other known polypeptide modifications.

In some embodiments, the polypeptide has a polyethylene glycol modification at the carboxyl terminus, and the sequence thereof is set forth in SEQ ID NO: 9, SEQ ID NO: 10, SEQ ID NO: 11 or SEQ ID NO: 27.

The polypeptide fragment provided by the present disclosure has an amino acid deletion in the polypeptide sequence set forth in SEQ ID NO: 1. It may respectively have an amino acid deletion at the amino terminus, the carboxyl terminus or inside of the amino acid sequence set forth in SEQ ID NO: 1; it may also simultaneously have amino acid deletions at the amino terminus and carboxyl terminus of the amino acid sequence set forth in SEQ ID NO: 1; it may also simultaneously have amino acid deletions at the amino terminus and inside of the amino acid sequence set forth in SEQ ID NO: 1; it may also simultaneously have amino acid deletions at the carboxyl terminus and inside of the amino acid sequence set forth in SEQ ID NO: 1; it may also simultaneously have amino acid deletions at the amino terminus, the carboxyl terminus and inside of the amino acid sequence set forth in SEQ ID NO: 1.

The number of the amino acid of the deletion of the present disclosure is no more than 12, including 12, such as deleting 1, 2, 3, 4, 5, 6, 7, 8, 9, 10, 11 or 12.

In some embodiments, the number of the amino acid of the deletion of the present disclosure is no more than 7, including 7, such as deleting 1, 2, 3, 4, 5, 6, or 7.

The number of the amino acid of the polypeptide fragment of the present disclosure may be any one of 6 to 17, including 6 and 17.

In a specific embodiment, the polypeptide fragment has a deletion of 2 amino acids at the carboxyl terminus of the amino acid sequence set forth in SEQ ID NO: 1, and the sequence of which is set forth in SEQ ID NO: 2.

In a specific embodiment, the polypeptide fragment simultaneously has amino acid deletions at the amino terminus and carboxyl terminus of the amino acid sequence set forth in SEQ ID NO: 1, wherein there is a deletion of 3 amino acids at the amino terminus and carboxyl terminus respectively, the sequence of which is set forth in SEQ ID NO: 4.

In a specific embodiment, the polypeptide fragment has a deletion of 3 amino acids at the amino terminus of the amino acid sequence set forth in SEQ ID NO: 1, the sequence of which is set forth in SEQ ID NO: 5.

In a specific embodiment, the polypeptide fragment has a deletion of 5 amino acids at the carboxyl terminus of the amino acid sequence set forth in SEQ ID NO: 1, the sequence of which is set forth in SEQ ID NO: 6.

In a specific embodiment, the polypeptide fragment simultaneously has amino acid deletions inside and carboxyl terminus of the amino acid sequence set forth in SEQ ID NO: 1, wherein there is a deletion of 3 amino acids inside of the amino acid sequence, and a deletion of 5 amino acids at the carboxyl terminus of the amino acid sequence, the sequence of which is set forth in SEQ ID NO: 8.

In a specific embodiment, the polypeptide fragment simultaneously has amino acid deletions at the amino terminus and carboxyl terminus of the amino acid sequence set forth in SEQ ID NO: 1, wherein there is a deletion of 2 amino acids at the amino terminus and carboxyl terminus respectively, the sequence of which is set forth in SEQ ID NO: 12.

In a specific embodiment, the polypeptide fragment simultaneously has amino acid deletions at the amino terminus and carboxyl terminus of the amino acid sequence set forth in SEQ ID NO: 1, wherein there is a deletion of 5 amino acids at the amino terminus and carboxyl terminus respectively, the sequence of which is set forth in SEQ ID NO: 13.

In a specific embodiment, the polypeptide fragment has a deletion of 5 amino acids at the amino terminus of the amino acid sequence set forth in SEQ ID NO: 1, the sequence of which is set forth in SEQ ID NO: 14.

The polypeptide fragment derivative of the present disclosure is a derivative having an amino acid substitution or/and addition to the amino acid sequence of the polypeptide set forth in SEQ ID NO: 1, i.e. the derivative having an amino acid substitution or/and addition to the amino acid sequence of the polypeptide fragment having an amino acid deletion in the amino acid sequence set forth in SEQ ID NO: 1.

In some embodiments, the polypeptide fragment derivative of the present disclosure is a derivative having an amino acid addition to the polypeptide fragment having an amino acid deletion in the amino acid sequence set forth in SEQ ID NO: 1.

In some embodiments, the polypeptide fragment derivative of the present disclosure is a derivative having an amino acid substitution to the polypeptide fragment having an amino acid deletion in the amino acid sequence set forth in SEQ ID NO: 1.

In some embodiments, the polypeptide fragment derivative of the present disclosure is a derivative simultaneously having an amino acid addition and substitution to the polypeptide fragment having an amino acid deletion in the amino acid sequence set forth in SEQ ID NO: 1.

For the polypeptide fragment derivative, the amino acid addition is an addition of amino acid at the amino terminus, the carboxyl terminus and any position inside of the amino acid sequence of the polypeptide fragment.

For polypeptide fragment derivative, the amino acid substitution is a substitution of amino acid at the amino terminus, the carboxyl terminus and any position inside of the amino acid sequence of the polypeptide fragment.

For polypeptide fragment derivative, the simultaneous addition and substitution is addition and substitution of amino acids at the carboxyl terminus, the amino terminus and any position inside of the amino acid sequence of the polypeptide fragment.

In the polypeptide fragment derivative, for the derivative having an amino acid substitution, the number of the amino acid of the substitution is within 6, including 6; for the derivative having an amino acid addition, the number of the amino acid of the addition is within 6, including 6.

In a specific embodiment, the polypeptide fragment derivative has an addition of 2 amino acids at the carboxyl terminus of the polypeptide fragment obtained by respectively having a deletion of 5 amino acids at the amino terminus and carboxyl terminus of the polypeptide sequence set forth in SEQ ID NO: 1, the sequence of the polypeptide fragment derivative is set forth in SEQ ID NO: 19.

In a specific embodiment, the polypeptide fragment derivative has an addition of 1 amino acid at the amino terminus of the polypeptide fragment obtained by having a deletion of 2 amino acids at the carboxyl terminus of the polypeptide sequence set forth in SEQ ID NO: 1, the sequence of which is set forth in SEQ ID NO: 20.

In a specific embodiment, the polypeptide fragment derivative has an addition of 1 amino acid at the amino terminus of the polypeptide fragment obtained by respectively having a deletion of 5 amino acids at the amino terminus and carboxyl terminus of the polypeptide sequence set forth in SEQ ID NO: 1, the sequence of which is set forth in SEQ ID NO: 21.

In a specific embodiment, the polypeptide fragment derivative has a substitution of 1 amino acid inside of the polypeptide fragment obtained by having a deletion of 3 amino acids at the amino terminus and a deletion of 5 amino acids at the carboxyl terminus of the polypeptide sequence set forth in SEQ ID NO: 1, the sequence of which is set forth in SEQ ID NO: 22.

In a specific embodiment, the polypeptide fragment derivative has a substitution of 1 amino acid inside of the polypeptide fragment obtained by having a deletion of 1 amino acid inside and a deletion of 2 amino acids at the carboxyl terminus of the polypeptide sequence set forth in SEQ ID NO: 1, the sequence of which is set forth in SEQ ID NO: 23.

In a specific embodiment, the polypeptide fragment derivative has a substitution of 1 amino acid inside of the polypeptide fragment obtained by respectively having a deletion of 2 amino acids at the amino terminus and carboxyl terminus of the polypeptide sequence set forth in SEQ ID NO: 1, the sequence of which is set forth in SEQ ID NO: 24.

The polypeptide derivative of the present disclosure is a polypeptide derivative having an amino acid substitution or/and addition to the amino acid sequence set forth in SEQ ID NO: 1.

In some embodiments, the polypeptide derivative is a derivative having an amino acid addition to the amino acid sequence set forth in SEQ ID NO: 1.

Further, in some embodiments, the polypeptide derivative is a derivative having an addition of 1 to 3 amino acids to the amino acid sequence set forth in SEQ ID NO: 1.

In some embodiments, the polypeptide derivative is a derivative having an amino acid substitution to the amino acid sequence set forth in SEQ ID NO: 1.

Further, in some embodiments, the polypeptide derivative is a derivative having a substitution of 1 to 3 amino acids to the amino acid sequence set forth in SEQ ID NO: 1.

In some embodiments, the polypeptide derivative is a derivative simultaneously having an amino acid addition and substitution to the amino acid sequence set forth in SEQ ID NO: 1.

Further, in some embodiments, the polypeptide derivative is a derivative simultaneously having an addition of 1 to 3 amino acids and a substitution of 1 to 3 amino acids to the amino acid sequence set forth in SEQ ID NO: 1.

For the polypeptide derivative of the present disclosure, the addition is an amino acid addition to the amino terminus, the carboxyl terminus and any position inside of the amino acid sequence set forth in SEQ ID NO: 1.

For the polypeptide derivative of the present disclosure, the substitution is an amino acid substitution to the amino terminus, the carboxyl terminus and any position inside of the amino acid sequence set forth in SEQ ID NO: 1.

For the polypeptide derivative of the present disclosure, the simultaneous addition and substitution is simultaneous addition and substitution of amino acids at the amino terminus, the carboxyl terminus and any position inside of the amino acid sequence of the amino acid sequence set forth in SEQ ID NO: 1.

In polypeptide derivative of the present disclosure, for the derivative having amino acid substitution, the number of the amino acid of the substitution is within 11, including 11. Further, the number is within 6, including 6, for the derivative having amino acid addition, the number of the amino acid of the addition is within 6, including 6.

In polypeptide derivative of the present disclosure, for the derivative having amino acid addition, the number of the amino acid of the addition is within 8, including 8. Further, the number is within 6, including 6.

In a specific embodiment, the polypeptide derivative having a substitution of 1 amino acid at position 15 inside of the polypeptide sequence set forth in SEQ ID NO: 1, the sequence of which is set forth in SEQ ID NO: 7.

In a specific embodiment, the polypeptide derivative having a substitution of 1 amino acid at position 18 inside of the polypeptide sequence set forth in SEQ ID NO: 1, the sequence of which is set forth in SEQ ID NO: 15.

In a specific embodiment, the polypeptide derivative having a substitution of 1 amino acid at position 7 inside of the polypeptide sequence set forth in SEQ ID NO: 1, the sequence of which is set forth in SEQ ID NO: 16.

In a specific embodiment, the polypeptide derivative having an addition of 1 amino acid at the carboxyl terminus of the polypeptide sequence set forth in SEQ ID NO: 1, the sequence of which is set forth in SEQ ID NO: 17.

In a specific embodiment, the polypeptide derivative having an addition of 1 amino acid at the amino terminus of the polypeptide sequence set forth in SEQ ID NO: 1, the sequence of which is set forth in SEQ ID NO: 18.

In a specific embodiment, the polypeptide derivative having a substitution of 1 amino acid at position 18 inside and simultaneously having an addition of 1 amino acid at the carboxyl terminus of the polypeptide sequence set forth in SEQ ID NO: 1, the sequence of which is set forth in SEQ ID NO: 25.

In a specific embodiment, the polypeptide derivative having an addition of 1 amino acid at the amino terminus and simultaneously having a substitution of 1 amino acid inside of the polypeptide sequence set forth in SEQ ID NO: 1, the sequence of which is set forth in SEQ ID NO: 26.

The amino acid substitution of the present disclosure is a replacement of a polypeptide fragment set forth in SEQ ID NO: 1 or an amino acid of the amino acid sequence set forth in SEQ ID NO: 1 using another conformation or other type of amino acid.

The amino acid addition of the present disclosure is an addition of amino acid to any position of the polypeptide fragment of the amino acid sequence set forth in SEQ ID NO: 1 or the amino acid sequence set forth in SEQ ID NO: 1.

The amino acid substitution and amino acid addition of the present disclosure may be performed simultaneously or respectively. It may be performed at the same amino acid position or at different amino acid positions.

The amino acid position of the present disclosure is the number of position of the amino acids arranged in order from the amino terminus to the carboxyl terminus in the amino acid sequence of the polypeptide. However, the amino acid position is relative. When amino acid deletion or addition is preformed, the position of the amino acid may change, and the change can be determined by those having ordinary skill in the art.

The amino acids for substitution or/and addition of the present disclosure include natural amino acids and unnatural amino acids, wherein the natural amino acids are amino acids existing in nature, and the unnatural amino acids include D-type amino acids and other artificially synthesized amino acids.

The derivative provided by the present disclosure is a variant of polypeptide. In the present disclosure, it may be a product having an amino acid substitution or addition to the polypeptide sequence, or a product having a chemical modification at a modification site such as an amino group, carboxyl group, sulfhydryl group, phenolic hydroxyl group, imidazolyl group, guanidine group, indolyl group, methylthio group at the end of the main chain or side chain.

The chemical modification of the present disclosure is a chemical modification using a suitable modification method and modifier at the level of polypeptide to make the modified polypeptide drug have improved solubility, increased stability and extended half-life, and the details can be determined by those having ordinary skill in the art.

The polypeptide derivative of the present disclosure may be a derivative having a chemical modification in the polypeptide fragment of the present disclosure or the polypeptide fragment derivative of the present disclosure.

Further, the polypeptide derivative may also be a derivative having a chemical modification in the polypeptide derivative of the present disclosure, i.e. a derivative having a chemical modification in the derivative having an amino acid addition to the amino acid sequence set forth in SEQ ID NO: 1, or the derivative having an amino acid substitution to the amino acid sequence set forth in SEQ ID NO: 1, or the derivative simultaneously having an amino acid addition and substitution to the amino acid sequence set forth in SEQ ID NO: 1.

The chemical modification can change the main chain structure or the side chain group of the peptide chain, including acetylation, amidation, glycosylation, polyethylene glycol (PEG) modification, fatty acid modification, and other known polypeptide modifications techniques in the art.

The acetylation and amidation of the present disclosure are commonly used methods for modifying the termins of a main chain of a polypeptide, usually acetylating the N-terminus of the main chain of a polypeptide, amidating the C-terminus of the main chain of the polypeptide.

The glycosylation modification of the present disclosure is binding a saccharide structure to certain special functional group in a protein polypeptide molecule using a covalent bond, including N-glycosylation, O-glycosylation, S-glycosylation, C-glycosylation, glycosylphosphatidylinositol modification, etc. The N-glycosylation is a binding to the amide nitrogen of the side chain by asparagine; the O-glycosylation is a binding to the oxygen on serine or threonine residues. The saccharide structure includes various monosaccharides, oligosaccharides and polysaccharides.

The PEG modification of the present disclosure is a modification using corresponding type of PEG at a site such as the functional group of polypeptide main chain amino group, side chain amino group, main chain carboxyl group, side chain carboxyl group, imidazolyl group, sulfhydryl group and hydroxyl group, etc. The PEG is a macromolecular polymer polymerized by ethylene oxide, and the structure or molecular weight is not limited. The PEG modification types include linear PEG, branched PEG, homobifunctional PEG derivatives, heterofunctional disubstituted PEG derivatives, and multi-arm functional PEG derivatives.

The fatty acid modification of the present disclosure is a modification binding a fatty acid structure to certain specific functional groups in a protein polypeptide molecule using a covalent bond, including amino group, carboxyl group, sulfhydryl group, hydroxyl group, etc. Fatty acid modification can be divided into unsaturated fatty acid and saturated fatty acid modification. Saturated fatty acid is a modification mainly using myristic acid and palmitic acid; unsaturated fatty acid modification is a modification mainly using oleic acid, linoleic acid, etc.

The polypeptide modification of the present disclosure can be carried out using methods well known to those having ordinary skill in the art. The purpose of the modification of the present disclosure is to change the physicochemical properties of the polypeptide sequence and improve the druggability, but the modified polypeptide can still inhibit TGF-β signal transduction.

The inhibition of TGF-β signaling pathway transduction of the present disclosure means using the polypeptide fragment, polypeptide fragment derivative, polypeptide derivative, and a polypeptide derivative via chemical modification of the above fragment or its derivative of the present disclosure in the condition that the TGF-β signaling pathway is activated to inhibit TGF-β activation, receptor phosphorylation, protein activation in an unlimited form in the TGF-β signaling pathway, and transcription and expression of downstream regulatory genes, which can be determined in a conventional method by those skilled in the art.

In some embodiments, the polypeptide derivative is a derivative having a chemical modification on the polypeptide fragment of the present disclosure.

Further, in some embodiments, the polypeptide derivative is a derivative having a PEG modification in the polypeptide fragment having a deletion of 1 to 10 amino acids in the polypeptide sequence set forth in SEQ ID NO: 1.

In a specific embodiment, the polypeptide derivative is a derivative having a PEG modification at the amino terminus of the polypeptide fragment having a deletion of 2 amino acids at the carboxyl terminus of the polypeptide sequence set forth in SEQ ID NO: 1, the sequence of which is set forth in SEQ ID NO: 3.

In a specific embodiment, the polypeptide derivative is a derivative having a PEG modification at the amino terminus of the polypeptide fragment having a deletion of 5 amino acids at the carboxyl terminus of the polypeptide sequence set forth in SEQ ID NO: 1, the sequence of which is set forth in SEQ ID NO: 9.

In a specific embodiment, the polypeptide derivative is a derivative having a PEG modification at the carboxyl terminus of the polypeptide fragment respectively having a deletion of 3 amino acids at the amino terminus and carboxyl terminus of the polypeptide sequence set forth in SEQ ID NO: 1, the sequence of which is set forth in SEQ ID NO: 10.

In a specific embodiment, the polypeptide derivative is a derivative having a PEG modification at the amino terminus of the polypeptide fragment respectively having a deletion of 3 amino acids at the amino terminus and carboxyl terminus of the polypeptide sequence set forth in SEQ ID NO: 1, the sequence of which is set forth in SEQ ID NO: 11.

In a specific embodiment, the polypeptide derivative is a derivative having a PEG modification at the amino terminus of the polypeptide fragment respectively having a deletion of 2 amino acids at the amino terminus and carboxyl terminus of the polypeptide sequence set forth in SEQ ID NO: 1, the sequence of which is set forth in SEQ ID NO: 28.

In a specific embodiment, the polypeptide derivative is a derivative having a PEG modification at the amino terminus of the polypeptide fragment respectively having a deletion of 5 amino acids at the amino terminus and carboxyl terminus of the polypeptide sequence set forth in SEQ ID NO: 1, the sequence of which is set forth in SEQ ID NO: 29.

In a specific embodiment, the polypeptide derivative is a derivative having a PEG modification at the carboxyl terminus of the polypeptide fragment respectively having a deletion of 5 amino acids at the amino terminus and carboxyl terminus of the polypeptide sequence set forth in SEQ ID NO: 1, the sequence of which is set forth in SEQ ID NO: 30.

In a specific embodiment, the polypeptide derivative is a derivative having a PEG modification at the amino terminus of the polypeptide fragment respectively having a deletion of 3 amino acids inside and a deletion of 5 amino acids at the carboxyl terminus of the polypeptide sequence set forth in SEQ ID NO: 1, the sequence of which is set forth in SEQ ID NO: 31.

In a specific embodiment, the polypeptide derivative is a derivative having a PEG modification at the carboxyl terminus of the polypeptide fragment having a deletion of 3 amino acids at the amino terminus of the polypeptide sequence set forth in SEQ ID NO: 1, the sequence of which is set forth in SEQ ID NO: 32.

In a specific embodiment, the polypeptide derivative is a derivative having a PEG modification at the carboxyl terminus of the polypeptide fragment respectively having a deletion of 5 amino acids at the amino terminus and carboxyl terminus of the polypeptide sequence set forth in SEQ ID NO: 1, the sequence of which is set forth in SEQ ID NO: 33.

In some embodiments, the polypeptide derivative is a derivative having a chemical modification in the polypeptide fragment derivate of the present disclosure.

Further, in some embodiments, the polypeptide derivative is a derivative having a PEG modification in the polypeptide fragment derivative having a deletion of 1 to 10 amino acids, an addition of 1 to 3 amino acids or a substitution of 1 to 3 amino acids in the polypeptide sequence set forth in SEQ ID NO: 1.

In a specific embodiment, the polypeptide derivative is a derivative having a PEG modification at the amino terminus of the polypeptide fragment derivative respectively having a deletion of 5 amino acids at the amino terminus and carboxyl terminus, and an addition of 2 amino acids at the carboxyl terminus of the polypeptide sequence set forth in SEQ ID NO: 1, the sequence of which is set forth in SEQ ID NO: 40.

In a specific embodiment, the polypeptide derivative is a derivative having a PEG modification at the carboxyl terminus of the polypeptide fragment derivative having a deletion of 2 amino acids at the carboxyl terminus, and an addition of 2 amino acids at the amino terminus of the polypeptide sequence set forth in SEQ ID NO: 1, the sequence of which is set forth in SEQ ID NO: 41.

In a specific embodiment, the polypeptide derivative is a derivative having a PEG modification at the amino terminus of the polypeptide fragment derivative respectively having a deletion of 5 amino acids at the amino terminus and carboxyl terminus, and an addition of 1 amino acid at the carboxyl terminus of the polypeptide sequence set forth in SEQ ID NO: 1, the sequence of which is set forth in SEQ ID NO: 42.

In a specific embodiment, the polypeptide derivative is a derivative having a PEG modification at the carboxyl terminus of the polypeptide fragment derivative having a deletion of 2 amino acids at the carboxyl terminus, and an addition of 1 amino acid at the amino terminus of the polypeptide sequence set forth in SEQ ID NO: 1, the sequence of which is set forth in SEQ ID NO: 43.

In a specific embodiment, the polypeptide derivative is a derivative having a PEG modification at the carboxyl terminus of the polypeptide fragment derivative having a deletion of 2 amino acids at the carboxyl terminus, and an addition of 1 amino acid inside of the polypeptide sequence set forth in SEQ ID NO: 1, the sequence of which is set forth in SEQ ID NO: 44.

In a specific embodiment, the polypeptide derivative is a derivative having a PEG modification at the carboxyl terminus of the polypeptide fragment derivative respectively having a deletion of 5 amino acids at the amino terminus and carboxyl terminus, and a substitution of 1 amino acid inside of the polypeptide sequence set forth in SEQ ID NO: 1, the sequence of which is set forth in SEQ ID NO: 45.

In a specific embodiment, the polypeptide derivative is a derivative having a PEG modification at the amino terminus of the polypeptide fragment derivative having a deletion of 1 amino acid inside, a deletion of 2 amino acids at the carboxyl terminus, and a substitution of 1 amino acid inside of the polypeptide sequence set forth in SEQ ID NO: 1, the sequence of which is set forth in SEQ ID NO: 46.

In a specific embodiment, the polypeptide derivative is a derivative having a PEG modification at the carboxyl terminus of the polypeptide fragment derivative having a deletion of 2 amino acids at the amino terminus, and a substitution of 1 amino acid inside of the polypeptide sequence set forth in SEQ ID NO: 1, the sequence of which is set forth in SEQ ID NO: 47.

In a specific embodiment, the polypeptide derivative is a derivative having a PEG modification at the carboxyl terminus of the polypeptide fragment derivative having a deletion of 1 amino acid inside, a deletion of 2 amino acids at the carboxyl terminus, and a substitution of 1 amino acid inside of the polypeptide sequence set forth in SEQ ID NO: 1, the sequence of which is set forth in SEQ ID NO: 48.

In a specific embodiment, the polypeptide derivative is a derivative having a PEG modification at the carboxyl terminus of the polypeptide fragment derivative respectively having a deletion of 2 amino acids at the amino terminus and carboxyl terminus, and a substitution of 1 amino acid inside of the polypeptide sequence set forth in SEQ ID NO: 1, the sequence of which is set forth in SEQ ID NO: 49.

In some embodiments, the polypeptide derivative is a derivative having a PEG modification in the polypeptide derivate, i.e. the derivate having an addition of 1 to 2 amino acids to the amino acid sequence set forth in SEQ ID NO: 1, of the present disclosure.

In a specific embodiment, the polypeptide derivative is a derivative having a PEG modification at the amino terminus of the polypeptide derivative having an addition of 1 amino acid at the carboxyl terminus of the polypeptide sequence set forth in SEQ ID NO: 1, the sequence of which is set forth in SEQ ID NO: 37.

In a specific embodiment, the polypeptide derivative is a derivative having a PEG modification at the carboxyl terminus of the polypeptide derivative having an addition of 1 amino acid at the amino terminus of the polypeptide sequence set forth in SEQ ID NO: 1, the sequence of which is set forth in SEQ ID NO: 38.

In a specific embodiment, the polypeptide derivative is a derivative having a PEG modification at the carboxyl terminus of the polypeptide derivative having an addition of 1 amino acid inside of the polypeptide sequence set forth in SEQ ID NO: 1, the sequence of which is set forth in SEQ ID NO: 39.

In some embodiments, the polypeptide derivative is a derivative having a PEG modification in the polypeptide derivate, i.e. the derivate having a substitution of 1 to 2 amino acids to the amino acid sequence set forth in SEQ ID NO: 1, of the present disclosure.

In a specific embodiment, the polypeptide derivative is a derivative having a PEG modification at the amino terminus of the polypeptide derivate having a substitution of 1 amino acid at position 15 inside of the polypeptide sequence set forth in SEQ ID NO: 1, the sequence of which is set forth in SEQ ID NO: 34.

In a specific embodiment, the polypeptide derivative is a derivative having a PEG modification at the carboxyl terminus of the polypeptide derivate having a substitution of 1 amino acid at position 15 inside of the polypeptide sequence set forth in SEQ ID NO: 1, the sequence of which is set forth in SEQ ID NO: 35.

In a specific embodiment, the polypeptide derivative is a derivative having a PEG modification at the carboxyl terminus of the polypeptide derivate having a substitution of 1 amino acid at position 7 inside of the polypeptide sequence set forth in SEQ ID NO: 1, the sequence of which is set forth in SEQ ID NO: 36.

In some embodiments, the polypeptide derivative is a derivative having a PEG modification in the polypeptide derivate, i.e. the derivate simultaneously having an addition of 1 to 3 amino acids and a substitution of 1 to 3 amino acids to the amino acid sequence set forth in SEQ ID NO: 1, of the present disclosure.

Further, the polypeptide derivative is a derivative having a PEG modification in the polypeptide derivate, i.e. the derivate simultaneously having an addition of 1 amino acids and a substitution of 1 amino acids to the amino acid sequence set forth in SEQ ID NO: 1, of the present disclosure.

In a specific embodiment, the polypeptide derivative is a derivative having a PEG modification at the amino terminus of the polypeptide derivate having a substitution of 1 amino acid at position 18 inside and an addition of 1 amino acid at the carboxyl terminus of the polypeptide sequence set forth in SEQ ID NO: 1, the sequence of which is set forth in SEQ ID NO: 50.

In a specific embodiment, the polypeptide derivative is a derivative having a PEG modification at the amino terminus of the polypeptide derivate having a substitution of 1 amino acid at position 15 inside and an addition of 1 amino acid at the amino terminus of the polypeptide sequence set forth in SEQ ID NO: 1, the sequence of which is set forth in SEQ ID NO: 51.

In a specific embodiment, the polypeptide derivative is a derivative having a PEG modification at the carboxyl terminus of the polypeptide derivate having a substitution of 1 amino acid at position 18 inside and an addition of 1 amino acid at the carboxyl terminus of the polypeptide sequence set forth in SEQ ID NO: 1, the sequence of which is set forth in SEQ ID NO: 52.

In a specific embodiment, the polypeptide derivative is a derivative having a PEG modification at the carboxyl terminus of the polypeptide derivate having a substitution of 1 amino acid at position 15 inside and an addition of 1 amino acid at the amino terminus of the polypeptide sequence set forth in SEQ ID NO: 1, the sequence of which is set forth in SEQ ID NO: 53.

In a specific embodiment, the polypeptide derivative is a derivative having a PEG modification at the carboxyl terminus of the polypeptide derivate having a substitution of 1 amino acid at position 7 inside and an addition of 1 amino acid inside of the polypeptide sequence set forth in SEQ ID NO: 1, the sequence of which is set forth in SEQ ID NO: 54.

The method for preparing the polypeptide, polypeptide fragment, polypeptide fragment derivative, polypeptide derivative, and the above-mentioned fragment and its derivative of the present disclosure includes extraction, enzymatic hydrolysis, fermentation, recombinant gene expression, and chemical synthesis.

The polypeptide, polypeptide fragment, polypeptide fragment derivative, polypeptide derivative, and a polypeptide derivative of the above-mentioned fragment and its derivative via chemical modification of the present disclosure can be used as an active ingredient for the manufacture of a medicament for prevention or treatment of a fibrosis disease, wherein the medicament for prevention or treatment of a fibrosis disease comprises a safe and effective dosage of one or more of the polypeptide, polypeptide fragment, polypeptide fragment derivative, polypeptide derivative, and a polypeptide derivative of the above-mentioned fragment and its derivative via chemical modification of the present disclosure for prevention or treatment.

The safe and effective amount for prevention or treatment is the amount of active ingredient administrated to a subject in need that is effective enough but can avoid serious side effects, within the scope of sound medical judgment. The safe and effective amount can be determined in a conventional method by those having ordinary skill in the art, although it varies depending on the following factors: the selected polypeptide (e.g., considering the structure, stability, and half-life of the polypeptide); the selected route of administration; the condition and severity of the condition to be treated; the age, body shape, body weight and physical condition of the subject to be treated; the history of the subject to be treated; the duration of the treatment; the expected treatment outcome and similar factors.

The prevention of the present disclosure is preventing or reducing the development of fibrosis when a possible pro-fibrogenic factor presenting. The treatment of the present disclosure is reducing the degree of fibrosis, or curing to normalize it, or slowing down the progression of fibrosis.

The fibrosis disease disclosed in the present disclosure is caused by of TGF-β cytokine and its signaling pathway excessive activation. The recognized fibrosis diseases in the field include, but are not limited to, rheumatoid arthritis, pulmonary fibrosis, hepatic fibrosis, cirrhosis, renal fibrosis, myelofibrosis, cystic fibrosis, myocardial fibrosis, scleroderma, sarcoidosis, keloids, burn-induced hypertrophic scars, proliferative retinopathy, glaucoma, cataract, posterior capsule opacification, vascular restenosis after angioplasty, vascular surgery or vascular injury, and Marfan syndrome.

The pulmonary fibrosis of the present disclosure is an end-stage change of a broad class of lung diseases characterized by fibroblast proliferation and a large amount of extracellular matrix aggregation accompanied by inflammatory damage and destruction of tissue structure. Alveolar macrophages, neutrophils, alveolar epithelial cells and fibroblasts in lung tissue extensively express TGF-β precursors. After epithelial cell damage, TGF-β activation promotes the proliferation of alveolar macrophages and fibroblasts and transforms into myofibroblasts, at the same time induces epithelial-mesenchymal transition, and eventually causes abnormal increased extracellular matrix and deposit. Pulmonary fibrosis is the formation of scars caused by abnormal repair after normal alveolar tissue is damaged. The pulmonary fibrosis of the present disclosure may be idiopathic pulmonary fibrosis, i.e. unexplained pulmonary fibrosis; or may be secondary pulmonary fibrosis, i.e. the pulmonary fibrosis caused by a plurality of causes. The cause may be occupational dust ($SiO_2$, etc.), radiation damage, autoimmune disease, drug side effects (bleomycin, etc.), chronic lung infection (tuberculosis), acute lung injury, etc. The pulmonary fibrosis of the present disclosure includes hypersensitivity pneumonitis, radiation-induced pulmonary fibrosis, bleomycin-induced pulmonary fibrosis, idiopathic pulmonary fibrosis, silicosis, asbestosis and pulmonary tuberculosis. The pulmonary fibrosis can be manifested as pulmonary inflammation, particularly one or more of interstitial pneumonia, degeneration of lung function and pulmonary consolidation (such as formation of a large amount of fibrosis connective tissue in pulmonary interstitium and lung structural disorders).

The rheumatoid arthritis of the present disclosure is a chronic inflammatory disease mainly manifested as synovitis, often accompanied by involvement of extra-articular organs, which may lead to joint deformity and loss of function. There are a large number of over-expressed and activated cytokines in synovial tissue. Wherein, TGF-β is abnormally activated before rheumatoid arthritis occurs, recruiting mesenchymal stem cells to the subchondral bone marrow, leading to osteoclastic bone resorption as well as bone resorption and bone formation of unconjugated bone, which result in degradation of the overlying articular cartilage, joint damage and destruction.

The myelofibrosis of the present disclosure is a myeloproliferative disorder caused by seriously affected hematopoietic function, which is caused by collagen proliferation in the bone marrow hematopoietic tissue. TGF-β is widely expressed in platelets, megakaryocytes and bone marrow cells in the bone marrow, promotes the synthesis of collagen and fibronectin, inhibits matrix metalloproteinases that decompose collagen, promotes the synthesis of metalloproteinase inhibitors, and eventually leads to collagen deposition. TGF-β may also cause vascular endothelial cell proliferation and bone marrow microvascular growth.

The systemic sclerosis of the present disclosure is a connective tissue disease characterized by clinically limited or diffuse skin thickening and fibrosis, and involves the internal organs such as the heart, lung, kidney, digestive tract. TGF-β promotes excessive deposition of extracellular matrix of skin fibroblasts while promoting the transformation of fibroblasts into myofibroblasts.

The burn-induced hypertrophic scar of the present disclosure is a serious sequela after wound healing in burn patients. It is an abnormal and unsound tissue lacking the vitality of normal tissues without normal skin tissue structure or physiological functions. The involved mechanism is complicated. Studies found that the expression of TGF-β in keratinocytes in burn scars is relatively high. In addition, TGF-β and its downstream regulatory factor connective tissue growth factor, decorin and binding protein P311 play an important role in wound healing and scar formation.

The cystic fibrosis of the present disclosure is a hereditary exocrine gland disease that primarily affects the gastrointestinal tract and respiratory system. Compared with the general population, TGF-β1 is significantly increased in patients with cystic fibrosis, and myofibroblast activation is obvious. The mechanism involves the TGF-β activated by mechanical stimulation promotes epithelial-mesenchymal transition, and transformation of fibroblasts into myofibroblasts, which ultimately leads to increased secretion of extracellular matrix, collagen deposition and tissue contracture.

The sarcoidosis of the present disclosure is a non-caseous necrotizing epithelial cell granulomatous inflammatory disease. It is mainly manifested as invasion of the lung parenchyma, and it involves many organs, such as the lymph nodes, skin, joints, liver, kidney and heart. The cause is not completely clear, but mainly involves the release of a large number of cytokines and growth factors such as TGF-β in inflammatory cells in or around granuloma tumors.

The myocardial fibrosis of the present disclosure is a result of myocardial fiber persistent and/or recurrent aggravation of myocardial ischemia and hypoxia caused by moderate to severe coronary atherosclerotic stenosis, and leads to chronic ischemic heart disease that gradually develops into heart failure. TGF-β can promote the transformation of cardiac fibroblasts and fibroblasts into myofibroblasts, epithelial-mesenchymal transition and endothelial-mesenchymal transition, increase extracellular matrix synthesis and promote the expression of connective tissue growth factor to promote the development of fibrosis.

The hepatic fibrosis of the present disclosure is a pathological process, which refers to abnormal proliferation of connective tissue in the liver caused by various pathogenic factors, and the lasting of the process of fibrosis will develop into cirrhosis. Cirrhosis is a chronic progressive liver disease, and is a diffuse liver damage caused by long-term or repeated action of one or more causes. The TGF-β signaling pathway is involved in the whole pathological process of hepatitis, hepatic fibrosis, cirrhosis and liver cancer. Normally, in hepatocytes, TGF-β can inhibit cell growth and promote apoptosis. Excessive activation of TGF-β after chronic liver injury leads to the transformation of hepatic stellate cells into myofibroblasts, excessive deposition of extracellular matrix, and the death of a large number of hepatocytes to produce inflammation and oxidative stress to produce fibrosis until cirrhosis.

The renal fibrosis of the present disclosure is a key and irreversible process in chronic kidney disease, which leads to irreversible kidney damages. TGF-β stimulates collagen synthesis in renal tubular epithelial cells and induces renal tubular epithelial cells to transform into myofibroblasts through epithelial-mesenchymal transition, and thereby resulting in renal fibrosis. The renal fibrosis of the present disclosure may be caused by pathogenic factors such as drug poisoning, hypertension, diabetes, persistence of cold, and infection.

The glaucoma of the present disclosure is a serious eye disease caused by an increase in intraocular pressure, which causes a disc depression and a visual field defect, and it may eventually lead to blindness. The increase of intraocular pressure is caused by an increase in the outflow resistance of the aqueous humor and lesions in the system of effusion outflow from the trabecular meshwork pathway caused by extracellular matrix deposition. TGF-β derived from aqueous humor can locally induce trabecular meshwork cells to express various extracellular matrices such as fibronectin, and break the extracellular matrix synthesis and decomposition equilibrium, which leads to extracellular matrix deposition.

The cataract of the present disclosure is the lens opacity caused by protein denaturation due to disorder of lens metabolism, which is caused by various factors such as aging, heredity, local nutritional disorders, immune and metabolic abnormalities, trauma, poisoning, radiation, etc. Posterior capsule opacification is the most common complication of extracapsular cataract extraction. Posterior capsule opacification after cataract surgery is caused by abnormal growth and degeneration fibrosis of lens epithelial cells left in the surgery. TGF-β-induced lens epithelial-mesenchymal transition is the major cause of posterior capsule opacification and fibrotic cataract.

The proliferative retinopathy of the present disclosure is a recurrent retinal detachment caused by contraction and stretching of the extensive fibrous proliferative membrane on the retinal surface and behind the vitreous body after rhegmatogenous retinal detachment surgery. The fibrous proliferative membrane is composed of retinal pigment epithelial cells, fibroblasts, glial cells and macrophages. TGF-β is overexpressed in the vitreous body, subretinal fluid and proliferative membrane, which induces migration and proliferation of retinal pigment epithelial cells and the transformation into myofibroblasts, and proliferation and contraction of glial cells.

The keloid of the present disclosure is result of excessive proliferation of collagen fibers caused by the lacking of normal constraint control in collagen synthesis and metabolism mechanism which continues to be hyperactive during the healing process of skin damages, and it is also known as connective tissue hyperplasia. TGF-β stimulates fibroblast proliferation, increases the synthesis and activity of matrix protease inhibitors, and activates connective tissue growth factor to promote collagen deposition and connective proliferation.

The vascular restenosis of the present disclosure is the restenosis of local vascular lumen caused by smooth muscle hyperplasia, collagen and scar tissue hyperplasia due to vascular healing response after angioplasty, vascular surgery or vascular injury. TGF-β can regulate downstream Smad and ERK/MAPK signaling pathways to promote vascular smooth muscle cell proliferation and neointimal formation, and promote extracellular matrix protein secretion and enhance intimal hyperplasia.

The Marfan syndrome of the present disclosure is a hereditary connective tissue disease characterized by slender and uneven limbs, fingers and toes, and the height is obviously higher than general people, accompanied by abnormal cardiovascular system, and it may also affect other organs including the lung, eye, dura mater, hard palate. Marfan syndrome is caused by a mutation in the microfibrin-1 (FBN1) gene encoding glycoprotein microfibrilla on chromosome 15, which blocks the formation of microfibrils. Since the interaction of microfibrin with potential TGF-β binding proteins can be used to stabilize the inactive TGF-β potential complex, TGF-β is overactivated when microfibrin is abnormal. The involved extracellular matrix composition and abnormal signal transduction together determine the phenotype of Marfan syndrome.

The subject to be treated of the present disclosure is a human or animal who have or may have the above disease and condition.

The use in prevention and treatment of the fibrosis disease of the present disclosure is that the polypeptide, polypeptide fragment, polypeptide fragment derivative, polypeptide derivative, and a polypeptide derivative of the above-mentioned fragment and its derivative via chemical modification of the present disclosure can be used as a single active ingredient, in combination with each other, or in combination with other traditional Chinese medicines, compounds or biological agents having activity to prevent or treat fibrosis as an active ingredient.

The polypeptide, polypeptide fragment, polypeptide fragment derivative, polypeptide derivative, and a polypeptide derivative of the above-mentioned fragment and its derivative via chemical modification of the present disclosure may be directly used as a drug substance, and may also be used via a pharmaceutically acceptable carrier to prepare a drug for prevention or treatment of the fibrosis disease. Wherein, the pharmaceutically acceptable carrier can be selected conventionally according to a pharmaceutical dosage form, such as diluent, filler, excipient, binder, wetting agent, disintegrant, effervescent agent, surfactant, absorption enhancer, lubricant, adsorption carrier, sustained release microsphere, implant agent, in situ forming microparticle, liposome, micro-emulsion, in situ hydrogel, nanometer grain, protease inhibitor, biological adhesive, fusion protein, antibody, and polypeptide.

The dosage form of the polypeptide, polypeptide fragment, polypeptide fragment derivative, polypeptide derivative, and a polypeptide derivative of the above-mentioned fragment and its derivative via chemical modification of the present disclosure is not specifically limited. It is a conventional dosage form in the art, preferably a solid, semi-solid or liquid, and may also be an aqueous solution, a non-aqueous solution or a suspension, and may also be a tablet, injection, capsule, granule, ophthalmic preparation, inhalation preparation, ointment, cream, spray, aerosol, gel, powder, paint, implant, lotion, etc.

The polypeptide, polypeptide fragment, polypeptide fragment derivative, polypeptide derivative, and a polypeptide derivative of the above-mentioned fragment and its derivative via chemical modification of the present disclosure may be administered by any suitable route of administration, preferably by injection, or by oral administration, pulmonary administration, nasal administration, transdermal administration, and ocular administration. Wherein the method of administration by injection preferably includes: intravenous injection or intravenous drip, intraperitoneal injection, subcutaneous injection, and intramuscular injection.

In one embodiment of the present disclosure, the selected polypeptide is a fragment of SEQ ID NO: 1, which is SEQ ID NO: 2 (abbreviated as N2) in the Sequence Listing. The selected polypeptide derivative SEQ ID NO: 3 (abbreviated as N3) is a product having a chemical modification in N2 by binding PEG2 to the N-terminus of the polypeptide via an amide bond. The dosage form of the selected polypeptide is an aqueous solution and the solvent is sterile 0.01 M PBS buffer. The selected subject to be treated is a rat with pulmonary fibrosis induced by bleomycin (BLM; the dose is 3 mg/kg). The selected rat is specific pathogen free (SPF) Sprague-Dawley (SD) rat. The weight of the rat is 200 to 250 g. The administration route of the selected N2 and N3 is minimally invasive intratracheal instillation, and the preferable doses of the polypeptide N2 and N3 are both 2.5 mg/kg. Compared with intratracheal instillation of bleomycin alone, after an intratracheal instillation of bleomycin and the polypeptide N2 or N3 to the rats, inflammatory cell infiltration was reduced, extracellular matrix protein synthesis was reduced, and collagen deposition was reduced, thereby pulmonary inflammation and fibrosis induced by bleomycin in rats were inhibited.

Further, in one embodiment of the present disclosure, the selected polypeptide, polypeptide fragments and derivatives thereof are set forth in SEQ ID NO: 4 to 11, respectively. The dosage form of the selected polypeptide, polypeptide fragments and derivatives is an aqueous solution and the solvent is sterile saline (pH 5 to 7). The selected subject to be treated is a rat with pulmonary fibrosis induced by bleomycin (BLM; the dose is 3 mg/kg). The selected rat is specific pathogen free (SPF) Sprague-Dawley (SD) rat. The weight of the rat is 200 to 250 g. The route of administration of the selected polypeptide, polypeptide fragments and derivatives is minimally invasive intratracheal instillation, and the doses of administration are all 6 mg/kg. Compared with intratracheal instillation of bleomycin alone, after an intratracheal instillation of bleomycin and the polypeptide, polypeptide fragment or derivative thereof set forth in SEQ ID NO: 4 to 11 to the rats, inflammatory cell infiltration was reduced, the deposition of extracellular matrix collagen was reduced, thereby pulmonary inflammation and fibrosis induced by bleomycin in rats were inhibited.

Further, in one embodiment of the present disclosure, the selected polypeptide, polypeptide fragments and derivatives thereof are set forth in SEQ ID NO: 2 to 54, respectively. The dosage form of the selected polypeptide, polypeptide fragments and derivatives is an aqueous solution and the solvent is sterile saline (pH 5 to 7). The selected subject to be treated is a rat with pulmonary fibrosis induced by bleomycin (the dose is 4 mg/kg). The selected rat is specific pathogen free (SPF) Sprague-Dawley (SD) rat. The weight of the rat is 200 to 250 g. The route of administration of the selected polypeptide, polypeptide fragments and derivatives is minimally invasive intratracheal instillation, and the doses of administration are all 8 mg/kg. Compared with intratracheal instillation of bleomycin alone, after an intratracheal instillation of bleomycin and the polypeptide, polypeptide fragment or derivative thereof set forth in SEQ ID NO: 2 to 54 to the rat, the decline of quality of life in rat caused by pulmonary fibrosis was significantly improved, inflammatory cell infiltration in lung tissue was reduced, the deposition of extracellular matrix collagen was reduced, the protein activation and gene expression of TGF-β significantly decreased during fibrosis, indicating that intratracheal instillation of the polypeptide, polypeptide fragment or derivative thereof set forth in SEQ ID NO: 2 to 54 can inhibit pulmonary inflammation and fibrosis induced by bleomycin in rats, and improve the decline of quality of life caused by fibrosis.

Further, in one embodiment of the present disclosure, the selected polypeptide, polypeptide fragments and derivatives thereof are set forth in SEQ ID NO: 2 to 54, respectively. The dosage form of the selected polypeptide, polypeptide fragments and derivatives is an aqueous solution and the solvent is sterile saline (pH 5 to 7). The selected subject to be treated is rat with pulmonary fibrosis induced by bleomycin (the dose is 4 mg/kg). The selected rat is specific pathogen free (SPF) Sprague-Dawley (SD) rat. The weight of the rat is 200 to 250 g. The route of administration of the selected polypeptide, polypeptide fragments and derivatives is intravenous injection, and the doses of administration are all 10 mg/kg. On the 4th day after the induction of bleomycin, sterile saline or the polypeptide, polypeptide fragment or derivative set forth in SEQ ID NO: 1 to 54 is started to be injected, once a day until the 13$^{th}$ day. Compared with the rat intravenously injected with saline, for the rat after an intravenous injection of the polypeptide, polypeptide fragment or derivative thereof set forth in SEQ ID NO: 2 to 54, the decline of quality of life in rats caused by pulmonary fibrosis was significantly improved, inflammatory cell infiltration in lung tissue was reduced, the deposition of extracellular matrix collagen was reduced, the gene expression and protein activation of TGF-β significantly decreased during fibrosis, indicating that intravenous injection of the polypeptide, polypeptide fragment or derivative thereof set forth in SEQ ID NO: 2 to 54 can inhibit pulmonary inflammation and fibrosis induced by bleomycin in rats, and improve the decline of quality of life caused by fibrosis.

Further, in one embodiment of the present disclosure, the selected polypeptide, polypeptide fragments and derivatives thereof are set forth in SEQ ID NO: 2 to 54, respectively. The dosage form of the selected polypeptide, polypeptide fragments and derivatives is an aqueous solution and the solvent is sterile saline (pH 5 to 7). The selected subject is specific pathogen free C57BL/6J mouse. The weight of the mouse is 16 to 17 g. The route of administration of the selected polypeptide, polypeptide fragments and derivatives thereof is intravenous injection, and the doses of administration are all 20 mg/kg. The mouse in the control group is injected with sterile saline once a day until the 13$^{th}$ day, and the brain, heart, liver, lung, kidney and spleen were stripped for pathological examination. Compared with the mouse intravenously injected with saline, after an intravenous injection of the polypeptide, polypeptide fragment or derivative thereof set forth in SEQ ID NO: 2 to 54, no associated organ toxicity in mouse was produced, and so it is safe. The beneficial effect of the present disclosure is: the present disclosure provides a polypeptide, a polypeptide fragment, a polypeptide fragment derivative and a polypeptide derivate, and a preparation method thereof, and a use thereof for the manufacture of a medicament in prevention and treatment of fibrosis diseases.

BRIEF DESCRIPTION OF DRAWINGS

In order to more clearly illustrate the embodiments of the present disclosure or the technical solutions in the conventional art, the drawings used in the embodiments or the conventional art description will be briefly described below.

DETAILED DESCRIPTION

Figure 1:
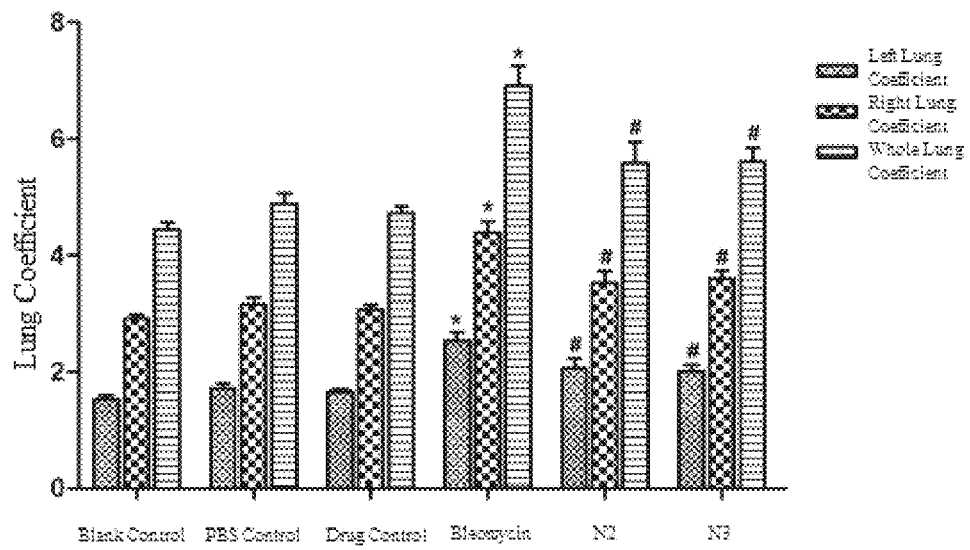
FIG. 1 shows the lung coefficient of the experimental animals.

The present disclosure will be further illustrated in details by the following examples, but the present invention is not limited to the scope of the examples. For the unspecified condition of the experimental method in the following examples, the experiments were carried out according to the conventional methods and conditions or the instruction of the products.

Example 1 Main Experimental Material, Animal and Peptide Synthesis

1. Main Experimental Material and Animal

Bleomycin hydrochloride was purchased from Hisun Pfizer Pharmaceuticals Co., LTD. (batch No. 16033811); Zoletil was purchased from French Virbac Co., Ltd. (batch number 6ALU); 0.9% sodium chloride injection solution was purchased from Sichuan Kelun Pharmaceutical Co., Ltd. (batch number: M16110319).

SPF grade SD rats were purchased from Chengdu Dashuo Experimental Animal Co., Ltd., male, weighing 200 to 250 g.

2. The sequences of the polypeptides N1 to N54 are set forth in SEQ ID NO: 1 to SEQ ID NO: 54 in Table 1, and the synthesis methods are as follows:

Fmoc-protected resin was used as a starting material, each amino acid was coupled one by one using the Fmoc solid phase synthesis method with a solid-phase peptide synthesizer to synthesize a fully protected peptide chain resin. The used amino acids were all natural L-form amino acids. The side chain fully protected peptide chain resin was cleaved by a cleavage reagent. The deprotected peptide was cleaved from the resin and the side chain protecting group was removed. A crude polypeptide was obtained by centrifugation and drying. Finally, the crude peptide was purified using preparative HPLC, specific components were collected, and lyophilized to obtain a purified polypeptide product. Purity detection conditions were: chromatography column: SepaxGP-C18 5μ 120 Å 4.6*150 mm, mobile phase composition: phase A 0.1% TFA in $H_2O$; phase B 0.09% TFA in (80% CAN+20% $H_2O$), flow rate 1.0 ml/min, phase B increased from 28.0-30.0% to 38.0-40.0% in 20-30, and a single injection was 30 μl.

PEG modification method: first, mPEG-SC and polypeptide (mole ratio (1.5 to 2.0):1) were weighed and placed in 40 ml to 100 ml of PBS buffer solution (pH 5 to 8.5), and reacted overnight at 4° C. The sample after reaction was purified using a semi-preparative high-performance liquid phase. The purification condition was: semi-preparative column: YMC, 250 mm×10 mm (5 μm filler); mobile phase: CAN (+0.1% TFA), $H_2O$ (+0.1% TFA); ACN linear gradient: 30%-35%; flow rate: 2 mL/min; running time: 15 min; loading volume: 1.0 ml; detection wavelength: 220 nm. When target peak rising, the product was collected by a centrifuge tube, pre-frozen in a −70° C. low temperature refrigerator overnight and then lyophilized using a freeze dryer until a whole white powder was visually observed (about 30 hours). Finally, the lyophilized product was obtained, weighed and recorded, and stored in a refrigerator at −20° C. for identification.

TABLE 1

Peptide Sequence

| Peptide Sequence | SEQ ID NO: | Sequence |
|---|---|---|
| N1 | 1 | TyrArgValArgPheLeuAlaLysGluAsnValThrGlnAspAlaGluAspAsn |
| N2 | 2 | TyrArgValArgPheLeuAlaLysGluAsnValThrGlnAspAlaGluAsp |
| N3 | 3 | (PEG2)TyrArgValArgPheLeuAlaLysGluAsnValThrGlnAspAlaGluAsp |
| N4 | 4 | ArgPheLeuAlaLysGluAsnValThrGlnAsp |
| N5 | 5 | ArgPheLeuAlaLysGluAsnValThrGlnAspAlaGluAspAsnCys |
| N6 | 6 | TyrArgValArgPheLeuAlaLysGluAsnValThrGlnAsp |
| N7 | 7 | TyrArgValArgPheLeuAlaLysGluAsnValThrGlnAspArgGluAspAsnCys |
| N8 | 8 | TyrArgPheLeuAlaLysGluAsnThrGlnAsp |
| N9 | 9 | (PEG2)TyrArgValArgPheLeuAlaLysGluAsnValThrGlnAsp |
| N10 | 10 | ArgPheLeuAlaLysGluAsnValThrGlnAsp(PEG2) |
| N11 | 11 | (PEG2)ArgPheLeuAlaLysGluAsnValThrGlnAsp |
| N12 | 12 | ValArgPheLeuAlaLysGluAsnValThrGlnAspAlaGluAsp |
| N13 | 13 | LeuAlaLysGluAsnValThrGlnAsp |
| N14 | 14 | LeuAlaLysGluAsnValThrGlnAspAlaGluAspAsnCys |
| N15 | 15 | TyrArgValArgPheLeuAlaLysGluAsnValThrGlnAspAlaGluAspArgCys |
| N16 | 16 | TyrArgValArgPheLeuArgLysGluAsnValThrGlnAspAlaGluAspAsnCys |
| N17 | 17 | TyrArgValArgPheLeuAlaLysGluAsnValThrGlnAspAlaGluAspAsnCysThr |
| N18 | 18 | PheTyrArgValArgPheLeuAlaLysGluAsnValThrGlnAspAlaGluAspAsnCys |

TABLE 1-continued

Peptide Sequence

| Peptide Sequence | SEQ ID NO: | Sequence |
|---|---|---|
| N19 | 19 | LeuAlaLysGluAsnValThrGlnAspArgCys |
| N20 | 20 | ArgTyrArgValArgPheLeuAlaLysGluAsnValThrGlnAspAlaGluAsp |
| N21 | 21 | SerLeuAlaLysGluAsnValThrGlnAsp |
| N22 | 22 | ArgPheLeuArgLysGluAsnValThrGlnAsp |
| N23 | 23 | TyrArgValArgPheLeuArgLysGluAsnThrGlnAspAlaGluAsp |
| N24 | 24 | ValArgPheLeuArgLysGluAsnValThrGlnAspAlaGluAsp |
| N25 | 25 | TyrArgValArgPheLeuAlaLysGluAsnValThrGlnAspAlaGluAspArgCysThr |
| N26 | 26 | PheTyrArgValArgPheLeuAlaLysGluAsnValThrGlnAspArgGluAspAsnCys |
| N27 | 27 | TyrArgValArgPheLeuAlaLysGluAsnValThrGlnAspAlaGluAspAsnCys(PEG2) |
| N28 | 28 | (PEG2)ValArgPheLeuAlaLysGluAsnValThrGlnAspAlaGluAsp |
| N29 | 29 | (PEG2)LeuAlaLysGluAsnValThrGlnAsp |
| N30 | 30 | LeuAlaLysGluAsnValThrGlnAsp(PEG2) |
| N31 | 31 | (PEG2)TyrArgPheLeuAlaLysGluAsnThrGlnAsp |
| N32 | 32 | ArgPheLeuAlaLysGluAsnValThrGlnAspAlaGluAspAsnCys(PEG2) |
| N33 | 33 | LeuAlaLysGluAsnValThrGlnAspAlaGluAspAsnCys(PEG2) |
| N34 | 34 | (PEG2)TyrArgValArgPheLeuAlaLysGluAsnValThrGlnAspArgGluAspAsnCys |
| N35 | 35 | TyrArgValArgPheLeuAlaLysGluAsnValThrGlnAspArgGluAspAsnCys(PEG2) |
| N36 | 36 | TyrArgValArgPheLeuAlaLysGluAsnValThrGlnAspAlaGluAspAsnCys(PEG2) |
| N37 | 37 | (PEG2)TyrArgValArgPheLeuAlaLysGluAsnValThrGlnAspAlaGluAspAsnCysThr |
| N38 | 38 | PheTyrArgValArgPheLeuAlaLysGluAsnValThrGlnAspAlaGluAspAsnCys(PEG2) |
| N39 | 39 | TyrArgValArgPheLeuAlaLysGluAsnValThrGlnAspAlaGluAspAsnThrCys(PEG2) |
| N40 | 40 | (PEG2)LeuAlaLysGluAsnValThrGlnAspArgCys |
| N41 | 41 | ArgTyrArgValArgPheLeuAlaLysGluAsnValThrGlnAspAlaGluAsp(PEG2) |
| N42 | 42 | (PEG2)LeuAlaLysGluAsnValThrGlnAspArg |
| N43 | 43 | ArgTyrArgValArgPheLeuAlaLysGluAsnValThrGlnAspAlaGluAsp(PEG2) |
| N44 | 44 | TyrArgSerValArgPheLeuAlaLysGluAsnValThrGlnAspAlaGluAsp(PEG2) |
| N45 | 45 | LeuAlaLysGluAsnArgThrGlnAsp(PEG2) |
| N46 | 46 | (PEG2)TyrArgValArgPheLeuArgLysGluAsnThrGlnAspAlaGluAsp |
| N47 | 47 | ValArgPheLeuAlaLysGluAsnValThrGlnAspAlaGluAspArgCys(PEG2) |
| N48 | 48 | TyrArgValArgPheLeuArgLysGluAsnThrGlnAspAlaGluAsp(PEG2) |
| N49 | 49 | ValArgPheLeuArgLysGluAsnValThrGlnAspAlaGluAsp(PEG2) |
| N50 | 50 | (PEG2)TyrArgValArgPheLeuAlaLysGluAsnValThrGlnAspAlaGluAspArgCysThr |
| N51 | 51 | (PEG2)PheTyrArgValArgPheLeuAlaLysGluAsnValThrGlnAspArgGluAspAsnCys |
| N52 | 52 | TyrArgValArgPheLeuAlaLysGluAsnValThrGlnAspAlaGluAspArgCysThr(PEG2) |
| N53 | 53 | PheTyrArgValArgPheLeuAlaLysGluAsnValThrGlnAspArgGluAspAsnCys(PEG2) |
| N54 | 54 | TyrArgValArgPheLeuArgLysGluAsnValThrGlnAspAlaGluAspAsnThrCys(PEG2) |

Example 2 Polypeptide and Rat Model of Pulmonary Fibrosis

1. Main Experimental Material and Animal

Bleomycin was produced from Nippon Kayaku Co., Ltd. (batch number: 650472); Zoletil 50 anesthetic was produced from French Virbac Co., Ltd.

N2 and N3 were synthesized by Chengdu Kaijie Biomedical Technology Development Co., Ltd. The sequence of N2 was: Tyr-Arg-Val-Arg-Phe-Leu-Ala-Lys-Glu-Asn-Val-Thr-Gln-Asp-Ala-Glu-Asp (the sequence is set forth in SEQ ID NO: 2). The sequence of N3 was: PEG2-Tyr-Arg-Val-Arg-Phe-Leu-Ala-Lys-Glu-Asn-Val-Thr-Gln-Asp-Ala-Glu-Asp (PEG2 was linked to the N-terminus of the polypeptide via an amide bond, the sequence is set forth in SEQ ID NO: 3).

SPF grade SD rats were purchased from Daping Hospital of Chongqing City, male, weighing 200 to 250 g.

2. Rat Model of Pulmonary Fibrosis

The rats were weighed before administration, intramuscularly injected with 65 mg/kg Zoletil anesthetic solution. After the rats entered the stage III anesthesia, the experimental rats were fixed in the lateral decubitus. Gavage needle size 12 was inserted into rat trachea through oral cavity along the glottis to instill with drug. The experimental animals were fed normally from the $1^{st}$ day to the $7^{th}$ day after intratracheal administration, and were weighed every day with feed and water ad libitum.

The rats in blank control group were received no treatment after anesthesia; the rats in model group (bleomycin) were intratracheally instilled with bleomycin (3 mg/kg); the rats in PBS control group were intratracheally instilled with an equal volume of sterile PBS buffer (0.01 M, pH=9.5); the rats in polypeptide control group were intratracheally instilled with 2.5 mg/kg of the polypeptide N2 (the solvent was 0.01 M, pH=9.5 PBS buffer); the rats in N2 treatment group were intratracheally instilled with 2.5 mg/kg of the polypeptide N2 and 3 mg/kg of bleomycin simultaneously, the rats in N3 treatment group were intratracheally instilled with 2.5 mg/kg of the polypeptide N3 and 3 mg/kg of bleomycin simultaneously.

Example 3 Detection of Lung Coefficient in Rat

The rats in Example 2 were weighed and sacrificed by anesthesia overdose. Lung tissue of both sides of the rats was taken, and the connective tissue around the lung tissue was carefully removed. After washing with saline and dried with a filter paper, the wet weight of the whole lung was weighted by an electronic balance. After the wet weight of the whole lung was weighted by the electronic balance, the lung coefficient was calculated according to the formula, lung coefficient=lung mass (mg)/body weight (g) (the result is shown in FIG. 1). The result shows that: compared with the blank control group, the PBS control group and the drug control group, the lung coefficients of the left lung, the right lung and the whole lung of the bleomycin group all increased significantly (*:$p<0.01$), indicating that the rat lung tissue had lesions; compared with the rats in the bleomycin group, the lung coefficients of the left lung, the right lung and the whole lung of the N2 and N3 treatment groups all decreased significantly (#:$p<0.05$), indicating that the lung tissue lesions in the N2 and N3 treatment groups were alleviated.

Example 4 HE Staining of Pathological Section of Rat Lung Tissue

Figure 2:
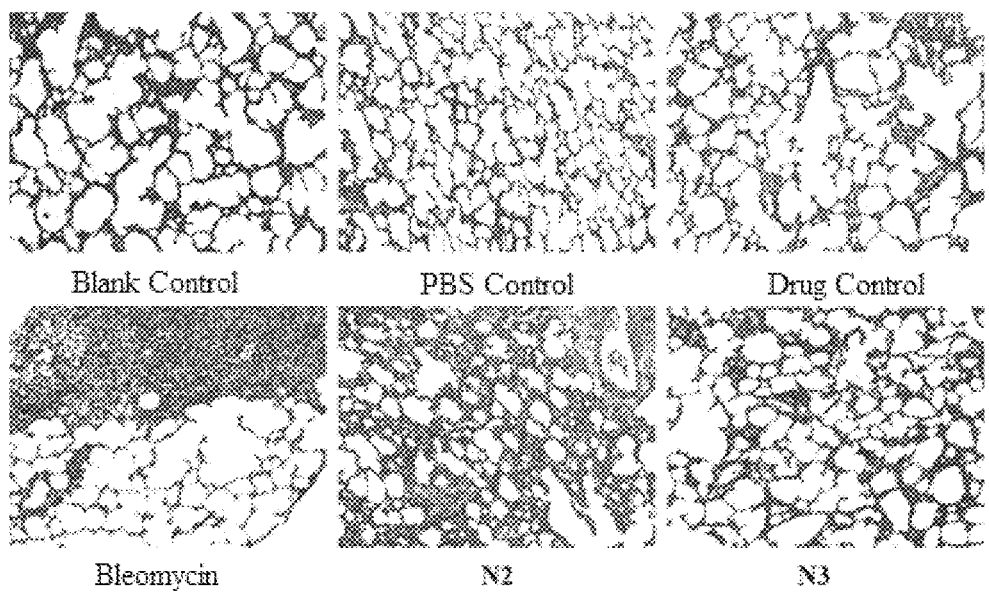
FIG. 2 shows the pathological section of the experimental animals.

The lung tissue of the rats of Example 2 was taken, fixed with 4% paraformaldehyde and embedded in paraffin. The wax block embedded the lung tissue was sectioned along the largest cross section. Pathological changes in lung tissue were observed using hematoxylin-eosin (HE) staining. Pathological changes in lung tissue were observed under a light microscope (low magnification) at a magnification of 100 times (the result is shown in FIG. 2). The result shows that: in the PBS control group and the drug control group, the alveolar morphology was normal, the alveolar wall was slender, and there was a very small amount of inflammatory cell infiltration in the interstitial; in the model group, there were more small areas of pulmonary parenchymal lesion, in which the alveolar wall was thickened, the alveolar septum was ruptured, isolated alveoli fused into pulmonary vesicles, more alveolar structures disappeared, and there was more inflammatory cell infiltration in the interstitial; compared with the model group, the alveolar structures of the lung tissue in the N2 and N3 groups were relatively intact, with a small amount of small areas of pulmonary parenchymal lesion, and there was a small amount of inflammatory cell infiltration in the interstitial.

Figure 3:
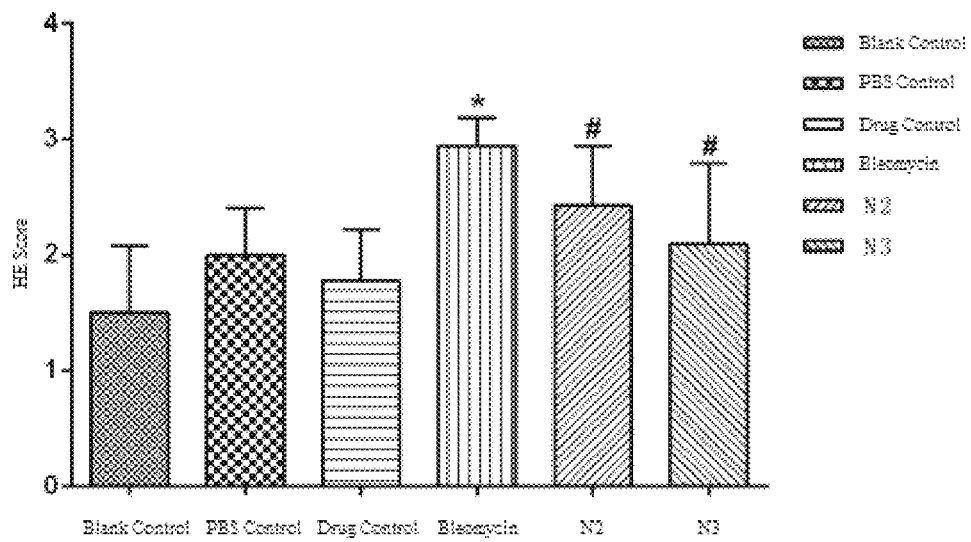
FIG. 3 shows the result of pathological section scores of experimental animals.

According to the method provided by Szapie, et al., the degree of alveolitis was graded according to the range of lesions and could be divided into 0 to 3 grades, corresponding to 0 to 3 points. The evaluation indexes for the degree of alveolitis are as follows: grade 0, no alveolitis; grade 1, mild alveolitis, manifested as a slight increase in alveolar septum, infiltration of monocytes, near the pleura or localized, with a lesion range of less than 20% without alveolar structural damage; grade 2, moderate alveolitis, the lesion ranges from 20% to 50%, relatively severe near the pleura; grade 3, severe alveolitis, diffusely distributed, the lesion range is more than 50%, with pulmonary parenchymal lesion occasionally. The result of the inflammatory pathology score (the result is shown in FIG. 3) shows that: compared with the blank control group, the PBS control group and the drug control group, there were significant inflammatory pathological changes of the rats in the bleomycin group (*:$p<0.01$); compared with the BLM group, there was significant alleviation in the inflammatory lesions in the rat lung tissue in N2 and N3 treatment groups (#:$p<0.01$). The result shows that the polypeptides N2 and N3 could inhibit pulmonary inflammation in rats caused by bleomycin.

Figure 4:
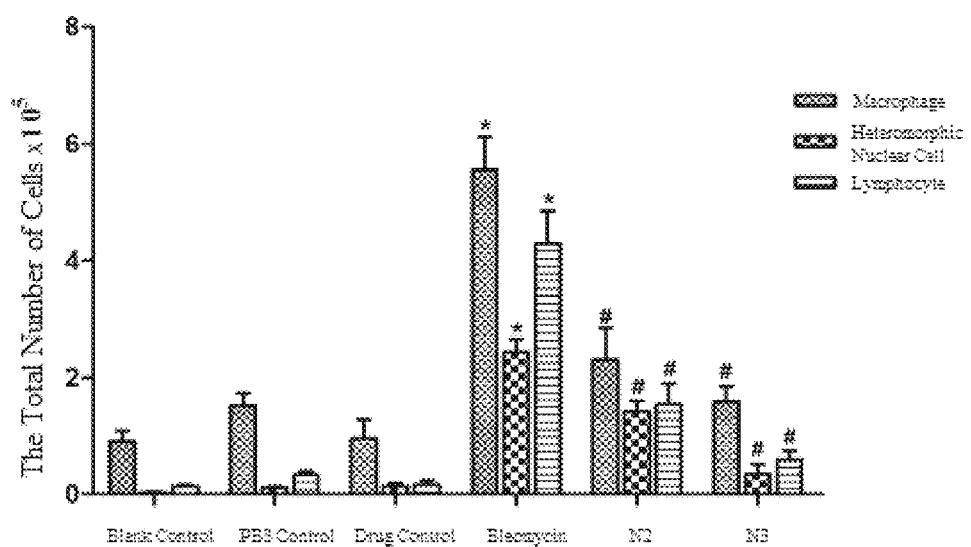
FIG. 4 shows the classification of inflammatory cells in bronchoalveolar lavage fluid of the experimental animals.

Example 5 Detection of the Change of the Number of Inflammatory Cells in Bronchoalveolar Lavage Fluid of Rats by Wright-Giemsa Staining Bronchoalveolar lavage fluid was collected, and resuspended by centrifugation. Another 5 µl of cell resuspension was applied to the microscope slide. After the cell suspension was naturally dried, an appropriate amount of methanol was added for a 30 second reaction, and then stained with Wright-Gemsa, counting and classification of cells were performed under microscope observation. The counting method was: the number of macrophages, lymphocytes, and neutrophils was calculated according to the total number of inflammatory cells based on the respective proportion of macrophages, lymphocytes, and neutrophils in 100 intact cells (the result is shown in FIG. 4). Compared with the rats in the blank control group, the PBS control group and the drug control group, the number of macrophages, heteromorphic nuclear cells and lymphocytes of the rats in the bleomycin group increased significantly (*:$p<0.01$); compared with the rats in the bleomycin group, the number of macrophages, heteromorphic nuclear cells and lymphocytes of the rats in the N2 and N3 treatment groups decreased significantly (#: p<0.05), indicating that the polypeptides N2 and N3 can inhibit pulmonary inflammation in rats caused by bleomycin.

Figure 5:
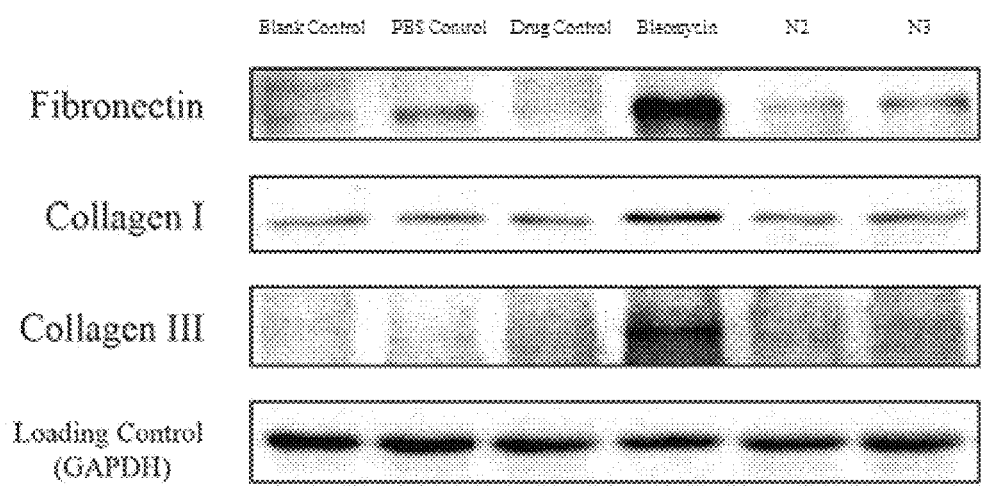
FIG. 5 shows the expression of extracellular matrix protein in lung tissue homogenate of the experimental animals.

Example 6 Detection of the Level of Extracellular Matrix Protein in Lung Tissue Homogenate of Rats by Western Blot The rat lung tissue of Example 2 was taken, and homogenized using RIPA lysate (100 mg of lung tissue corresponding to 1 mL of lysate), centrifuged and the supernatant was taken, and then the protein concentration was determined by BCA method. Equal amounts of protein samples were taken and Western blot experiment was performed using anti-GAPDH, anti-Fibronectin, anti-Collagen I and anti-Collagen III antibodies (the result is shown in FIG. 5).

Using GAPDH as an internal reference, compared with the blank control group, the PBS control group and the drug control group, the intensities of the expression bands of Fibronectin, Collagen I and Collagen III in the rat lung tissue of the BLM group increased significantly, indicating that bleomycin induced extracellular matrix deposition in the rat lung tissue; compared with the bleomycin group, the intensities of the expression bands of Fibronectin, Collagen I and Collagen III in the rat lung tissue of the treatment groups almost returned to the level of the control group, indicating that the polypeptides N2 and N3 could significantly reduce pulmonary fibrosis caused by bleomycin.

Figure 6:
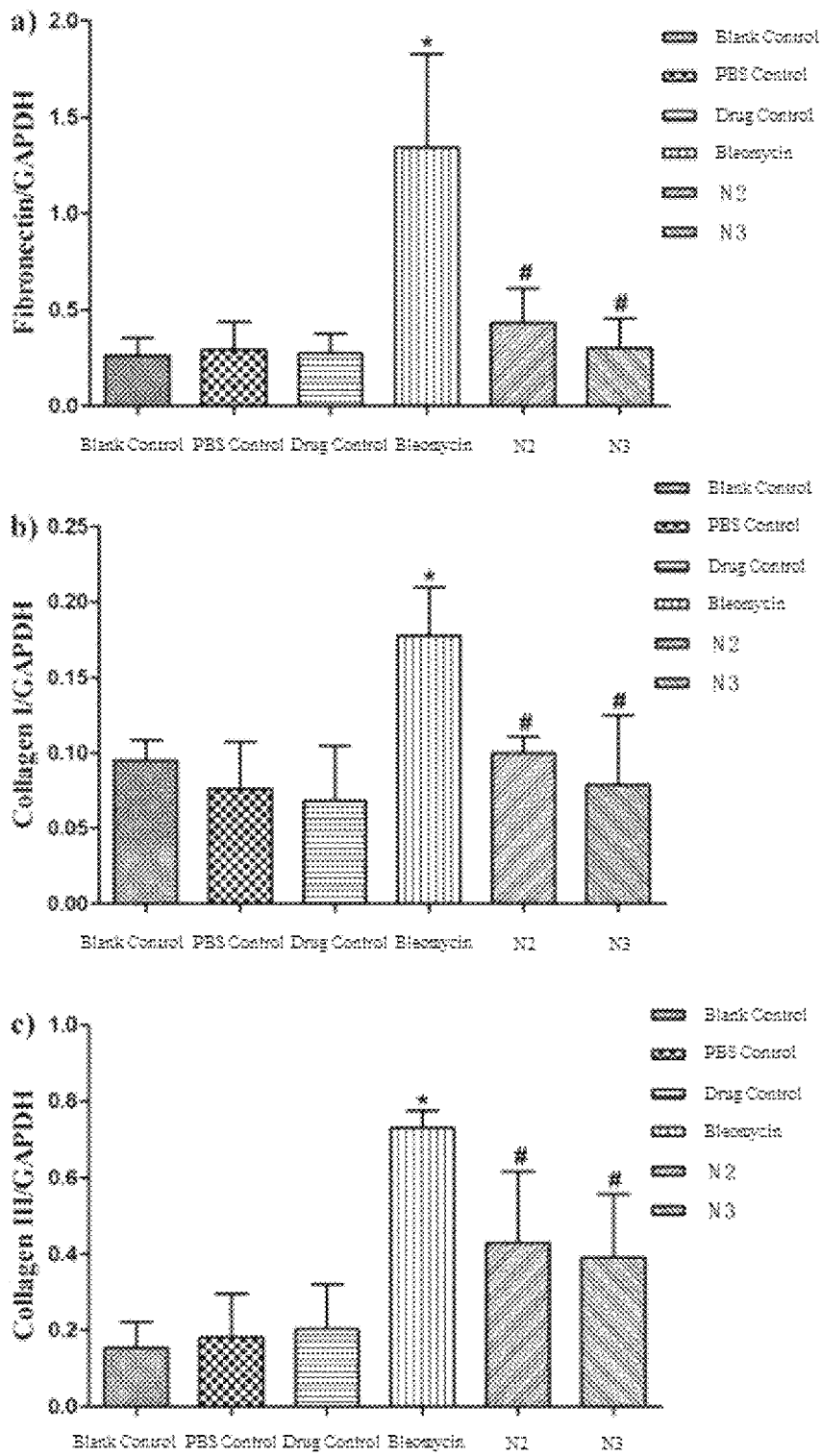
FIG. 6 shows the semi-quantitative analysis of extracellular matrix protein in lung tissue homogenate of the experimental animals.

The grayscale value of each band was detected and analyzed using Image pro plus 6.0 image analysis software (the result is shown in FIG. 6). The result shows that: compared with the rats in the blank control group, the PBS control group and the drug control group, the levels of Fibronectin, Collagen I and Collagen III proteins in the rat lung tissue of the bleomycin group increased significantly (*:p<0.01); compared with the rats in the bleomycin group, the levels of Fibronectin, Collagen I and Collagen III proteins of the rats in the N2 and N3 treatment groups decreased significantly (#:p<0.05). The detection of grayscale value supported the above-mentioned description.

Example 7 Detection of Hydroxyproline Content in Lung Tissue Homogenate of Rats

Figure 7:
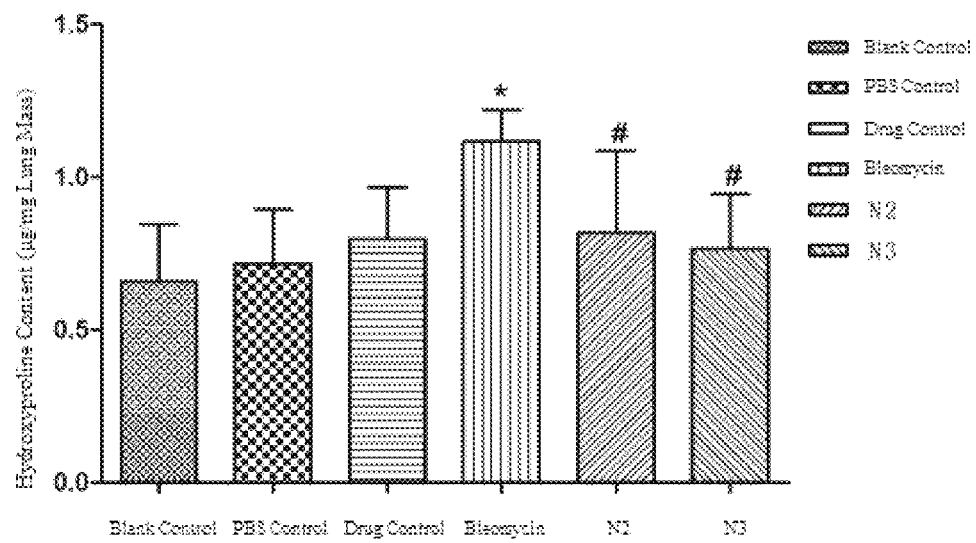
FIG. 7 shows the hydroxyproline content in lung tissue of the experimental animals.

The rats of Example 2 were taken, and the hydroxyproline content in lung tissue homogenate was detected using Boster Hydroxyproline Alkali Hydrolysis Assay Kit (Cat. No. A030) (the result is shown in FIG. 7). The result shows that: compared with the blank control group, the PBS control group and the drug control group, the hydroxyproline content in lung tissue of the bleomycin group increased significantly (*:p<0.01), indicating that BLM induced collagen fiber deposition in lung of the rats; compared with the bleomycin group, the hydroxyproline content in lung tissue of the N2 and N3 treatment groups decreased significantly (#: p<0.05), indicating that the polypeptides N2 and N3 significantly inhibited BLM-induced pulmonary fibrosis.

Figure 8:
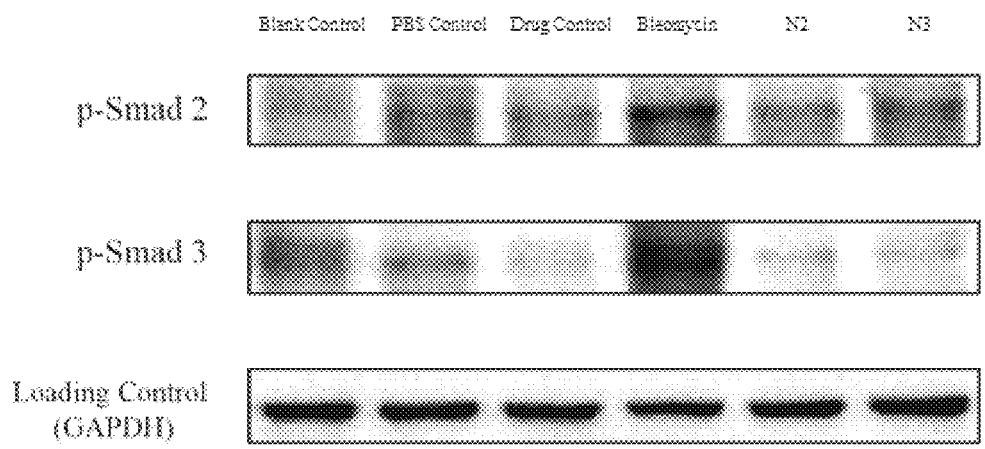
FIG. 8 shows the Smad protein expression in lung tissue homogenate of the experimental animals.

Example 8 Detection of the Level of Smad Protein in Lung Tissue Homogenate of Rats by Western Blot The rat lung tissue of Example 2 was taken, and the tissue was homogenized using RIPA lysate (100 mg of lung tissue corresponding to 1 mL of lysate), centrifuged and the supernatant was taken, and then the protein concentration was determined by BCA method. Equal amounts of protein samples were taken and Western blot experiment was performed using anti-GAPDH, anti-p-Smad2 and anti-p-Smad3 antibodies (the result is shown in FIG. 8).

Using GAPDH as an internal reference, compared with the blank control group, the PBS control group and the drug control group, the intensities of the expression bands of p-Smad2 (phosphorylated Smad2) and p-Smad3 (phosphorylated Smad3) in the rat lung tissue of the BLM group increased significantly, indicating that bleomycin induced transduction of TGF-β/Smad signaling pathway in the rat lung tissue; compared with the bleomycin group, the intensities of the expression bands of p-Smad2 and p-Smad3 in the rat lung tissue of the N2 and N3 treatment groups almost returned to the level of the control group, indicating that the peptides N2 and N3 could significantly inhibit the transduction of TGF-β/Smad signaling pathway in lung tissue induced by bleomycin.

Figure 9:
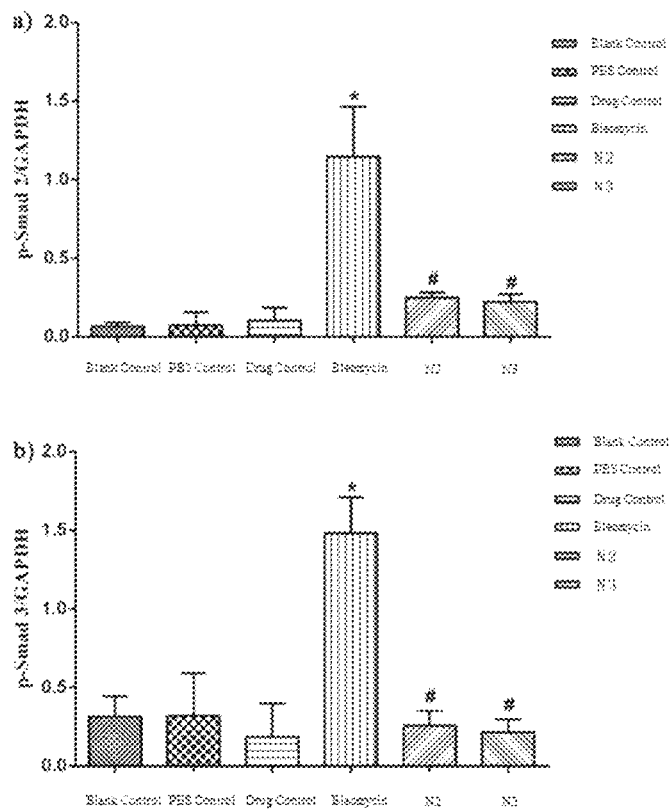
FIG. 9 shows the semi-quantitative analysis of Smad protein in lung tissue homogenate of the experimental animals.

The grayscale value of each band was detected and analyzed using Image pro plus 6.0 image analysis software (the result is shown in FIG. 9). The result shows that: compared with the rats in the blank control group, the PBS control group and the drug control group, the levels of p-Smad2 and p-Smad3 proteins in the rat lung tissue of the bleomycin group increased significantly (*:p<0.01); compared with the rats in the bleomycin group, the levels of p-Smad2 and p-Smad3 proteins of the rats in the N2 and N3 treatment groups decreased significantly (#:p<0.05). The detection of grayscale value supported the above-mentioned description.

Example 9 Polypeptide and Rat Model of Pulmonary Fibrosis

1. Mail Experimental Material and Animal

Bleomycin was purchased from Hisun Pfizer Pharmaceuticals Co., LTD. (batch number 16037911, 16033811); Zoletil 50 anesthetic was produced by French Virbac Co., Ltd.

Polypeptide, polypeptide fragment and derivative thereof SEQ ID NO: 4 (abbreviated as N4), SEQ ID NO: 5 (abbreviated as N5), SEQ ID NO: 6 (abbreviated as N6), SEQ ID NO: 7 (abbreviated as N7), SEQ ID NO: 8 (abbreviated as N8), SEQ ID NO: 9 (abbreviated as N9), SEQ ID NO: 10 (abbreviated as N10) and SEQ ID NO: 11 (abbreviated as N11) were synthesized by Chengdu Kaijie Biomedical Technology Development Co., Ltd. The sequences are set forth in SEQ ID NO: 4 to 11.

SPF grade SD rats were purchased from Chengdu Dashuo Experimental Animal Co., Ltd., male, weighing 200 to 250 g.

2. Rat Model of Pulmonary Fibrosis

The rats were weighed before administration, intramuscular injection of Zoletil anesthetic solution, the dose was 65 mg/kg. After the rats entered the stage III anesthesia, the experimental rats were bond in the incline lateral decubitus. A size 12 gavage needle was inserted into rat trachea through oral cavity along the glottis to infuse the drug. The experimental animals were fed normally from the $1^{st}$ day to the $14^{th}$ day after intratracheal administration, and were weighed regularly every day without restriction of feed or drinking water.

The rats in model group were intratracheally instilled with bleomycin (3 mg/kg); the rats in control group were intratracheally instilled with an equal volume of saline; the rats in treatment groups were intratracheally instilled with bleomycin (3 mg/kg) and corresponding therapeutic drug (6 mg/kg) simultaneously.

Example 10 Detection of Active TGF-β in Lung Tissue of Rats by ELISA

Figure 10:
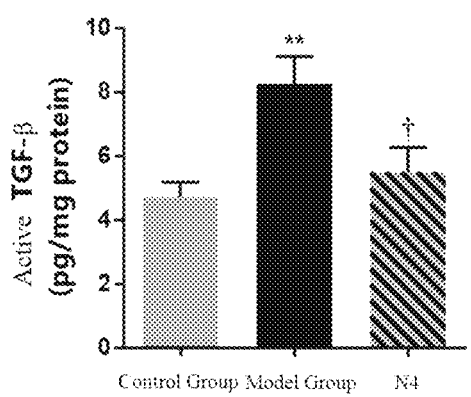
FIG. 10 shows the content of active TGF-β in lung tissue of the experimental animals.

The rat lung tissue in the model group, the control group and the N4 treatment group of Example 9 was taken, and homogenized using RIPA lysate (100 mg of lung tissue corresponding to 1 mL of lysate), centrifuged and the supernatant was taken, and then the protein concentration was determined by BCA method. Equal amounts of protein samples were taken and the active TGF-β content was measured by enzyme-linked immunosorbent assay ELISA (Promega, Cat. No. G7591) (the result is shown in FIG. 10), and one-way ANOVA was used for biostatistical analysis.

Compared with the control group, the active TGF-β content in rat lung tissue in the model group increased significantly (**: $p<0.01$); compared with the model group, the content of active TGF-β in the lung tissue of the N4 treatment group decreased significantly (t: $p<0.05$), indicating that N4 can significantly inhibit the activation of TGF-β induced by bleomycin.

Figure 11:
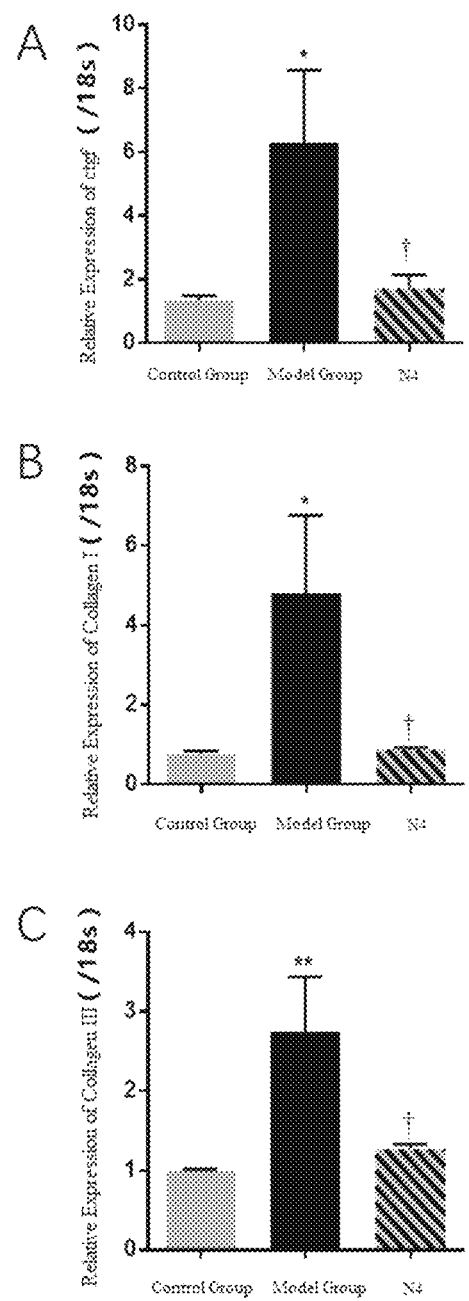
FIG. 11 shows the gene expression of ctgf, collagen I and collagen III in lung tissue of the experimental animals.

Example 11 Detection of the Contents of Ctgf, Collagen I and Collagen III in Lung Tissue of Rats by RT-qPCR The rat lung tissue in the model group, the control group and the N4 treatment group of Example 9 was taken. RNA in lung tissue was extracted using TRIZOL (Invitrogen) method. After obtaining cDNA using reverse transcription, fluorescence quantitative PCR (qPCR) kit (Applied Biosystems, Cat. No. 4319413E) was used to detect the expression levels of connective tissue growth factor ctgf (forward primer: 5'-TGGCCCTGACCCAACTATGA-3', reverse primer: 5'-CTTAGAACAGGCGCTCCACTCT-3') downstream of the TGF-β pathway, Collagen I (forward primer: 5'-TGCCGATGTCGCTATCCA-3', reverse primer: 5'-TCTTGCAGTGATAGGTGATGTTCTG-3') and Collagen III (forward primer: 5'-GGAAAAGATGGAT-CAAGTGGACAT-3', reverse primer: 5'-GAGCCCTCA-GATCCTCTTTCAC-3'). 18S RNA was used as an internal reference (the result is shown in FIG. 11), and one-way ANOVA was used for biostatistical analysis.

Compared with the control group, the expression levels of ctgf, collagen I and collagen III in the lung tissue of the model group increased significantly (*:$p<0.05$, **: $p<0.01$); compared with the model group, the gene expression levels of ctgf, collagen I and collagen III in lung tissue of the N4 treatment group decreased significantly (†:$p<0.05$), indicating that N4 can significantly inhibit bleomycin-induced TGF-β signaling pathway.

Figure 12:
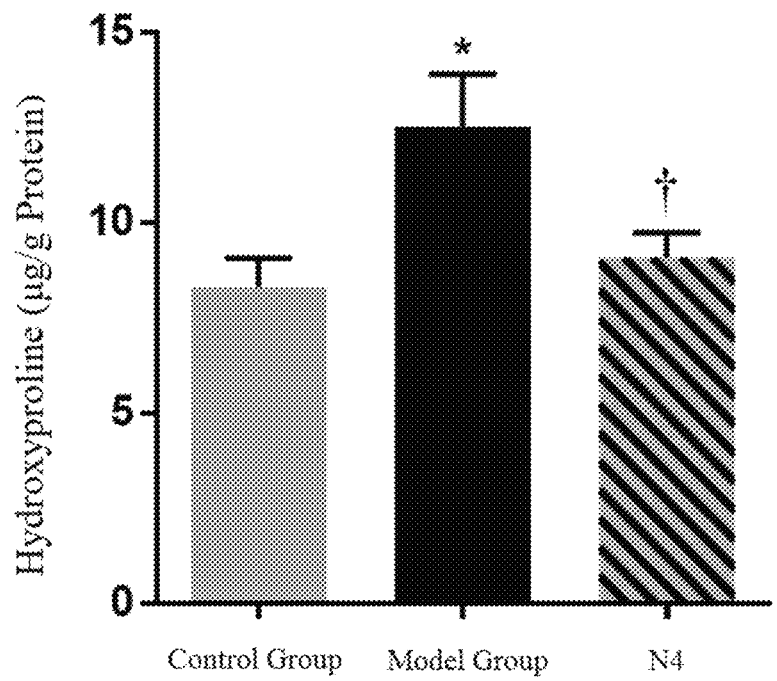
FIG. 12 shows the expression of hydroxyproline content in lung tissue of the experimental animals.

Example 12 Detection of Hydroxyproline Content in Lung Tissue Homogenate of Rats by Acid Hydrolysis Method The lung tissue in the model group, the control group and the N4 treatment group of Example 9 was taken, and the hydroxyproline content in the lung tissue homogenate was detected using BioVision Hydroxyproline Acid Hydrolysis Assay Kit (Cat. No. K555-100) (the result is shown in FIG. 12), and one-way ANOVA was used for biostatistical analysis.

Compared with the control group, the hydroxyproline content in lung tissue of the model group increased significantly (*:$p<0.05$), indicating that BLM induced collagen fiber deposition in the lung of rats; compared with the model group, the hydroxyproline content in lung tissue of the N4 treatment group decreased significantly (†:$p<0.05$), indicating that N4 significantly inhibited BLM-induced pulmonary fibrosis.

Example 13 HE Staining of Pathological Section of Rat Lung Tissue

Figure 13:
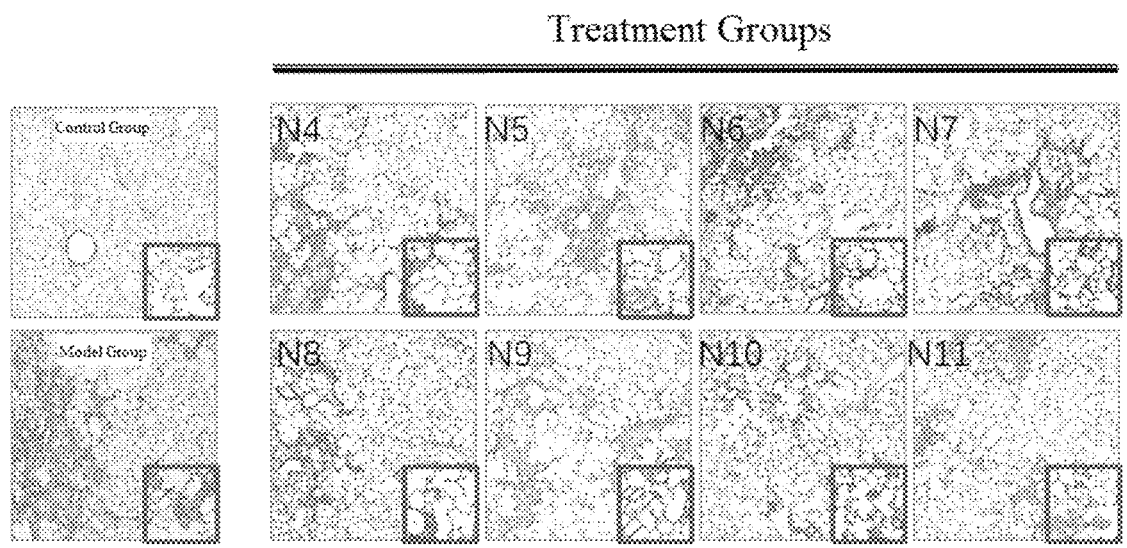
FIG. 13 shows the pathological examination (HE) of lung tissue of the experimental animals.

The lung tissue of the rats of Example 9 was taken, fixed with 4% paraformaldehyde and embedded in paraffin. The wax block embedded the lung tissue was sectioned along the largest cross section. Pathological changes in lung tissue were observed using hematoxylin-eosin (HE) staining. Pathological changes in lung tissue were observed under a light microscope (low magnification) at a magnification of 100 times (the result is shown in FIG. 13). The result shows that: in the control group, the alveolar morphology was normal, the alveolar wall was slender, and there was a very small amount of inflammatory cell infiltration in the interstitial; in the model group, there were more small areas of pulmonary parenchymal lesion, in which the alveolar wall was thickened, the alveolar septum was ruptured, isolated alveoli fused into pulmonary vesicles, more alveolar structures disappeared, and there was more inflammatory cell infiltration in the interstitial; compared with the model group, the alveolar structures of the rat lung tissue in each group were relatively intact, with a small amount of small areas of pulmonary parenchymal lesion, and there was a small amount of inflammatory cell infiltration in the interstitial.

Figure 14:
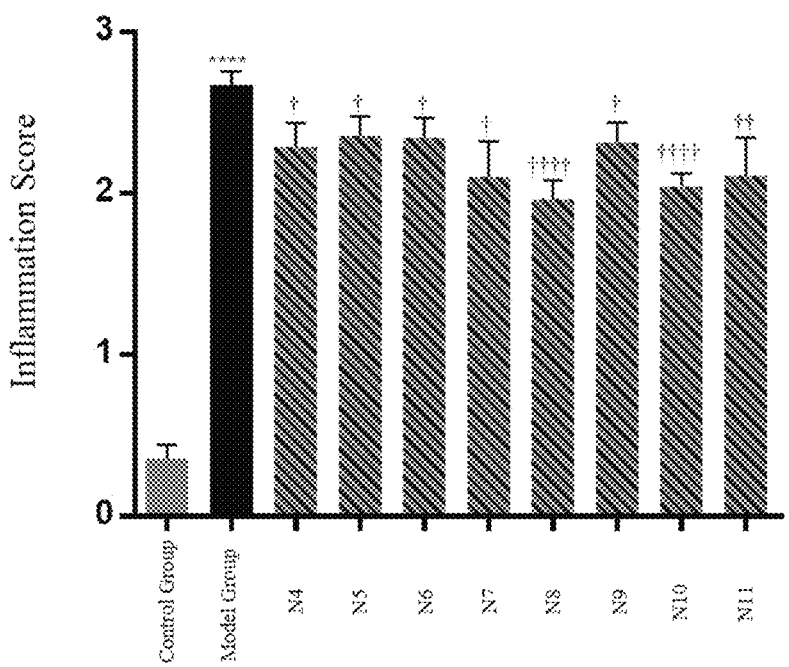
FIG. 14 shows the scoring result of the pathological examination (HE) of lung tissue of the experimental animals.

According to the method provided by Szapie, et al., the degree of alveolitis was graded according to the range of lesions and could be divided into 0 to 3 grades, corresponding to 0 to 3 points. The evaluation indexes for the degree of alveolitis are as follows: grade 0, no alveolitis; grade 1, mild alveolitis, manifested by a slight increase in alveolar septum, infiltration of monocytes, near the pleura or localized, with a lesion range of less than 20% without alveolar structural damage; grade 2, moderate alveolitis, the lesion ranges from 20% to 50%, relatively severe near the pleura; grade 3, severe alveolitis, diffusely distributed, the lesion range is more than 50%, with pulmonary parenchymal lesion occasionally. The result of the inflammatory pathology score (the result is shown in FIG. 14, and one-way ANOVA was used for biostatistical analysis) shows that: compared with the control group, there were significant inflammatory pathological changes in the lung tissue in the model group (****: $p<0.0001$); compared with the rats in the BLM group, there were different degrees of significant improvement in the inflammatory lesions in rat lung tissue in N4 to N11 treatment groups (†:$p<0.05$, ††:$p<0.01$, ††††:$p<0.0001$), indicating that all of the N4 to N11 can inhibit pulmonary inflammation in rats caused by bleomycin.

Example 14 Masson Staining of Pathological Section of Rat Lung Tissue

Figure 15:
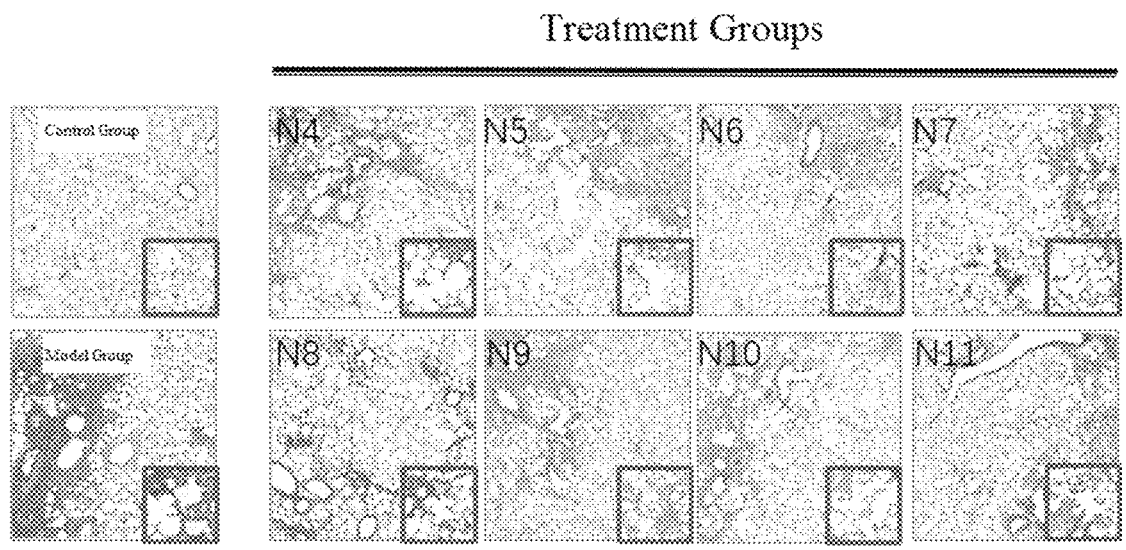
FIG. 15 shows the pathological examination (Masson) of lung tissue of the experimental animals.

The lung tissue of the rats of Example 9 was taken, fixed with 4% paraformaldehyde and embedded in paraffin. The wax block embedded the lung tissue was sectioned along the largest cross section. Pathological changes in lung tissue were observed using staining by Masson's trichrome stain (Masson). Pathological changes in lung tissue were observed under a light microscope (low magnification) at a magnification of 100 times (the result is shown in FIG. 15). The result shows that: the alveolar morphology in the control group was normal, only a very small amount of alveolar septum was ruptured and thicken, no isolated nodules or fibrous mass formed; in the model group, the alveolar septum in the rat lung tissue was ruptured and thicken, some of the alveolar structure enlarged and loose, there were isolated nodules formed, the alveolar septum varied or disappeared, fibrous mass formed and fused even obliterated the alveolar; compared with the model group, in the N4 to N11 treatment groups, the alveolar septum ruptured was less, degree of thickening was weaker, and the alveolar structures were mostly intact with a small number of isolated nodules or fibrous masses.

Figure 16:
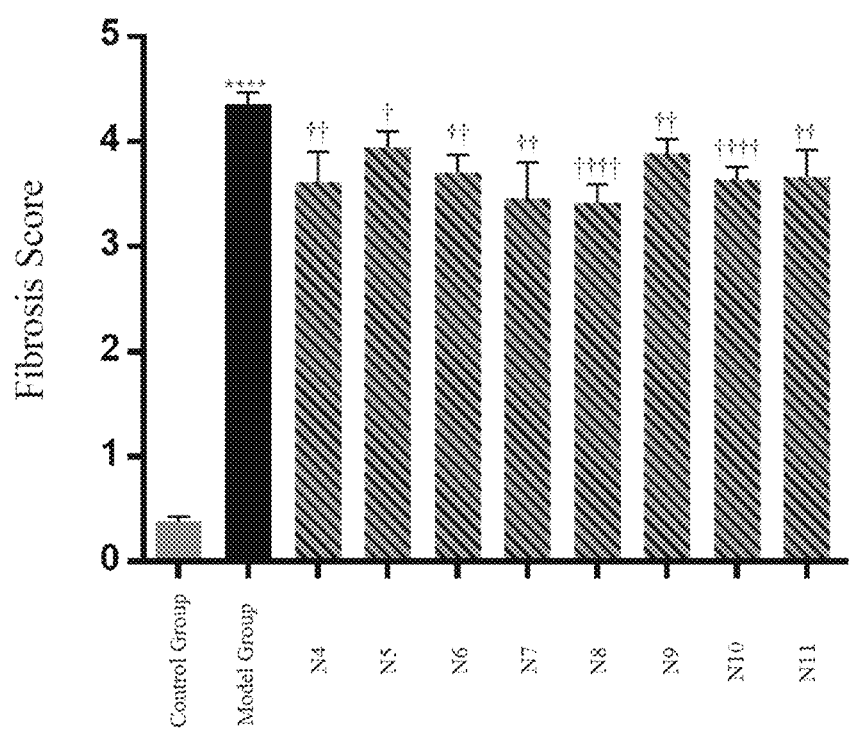
FIG. 16 shows the scoring result of the pathological examination (Masson) of lung tissue of the experimental animals.

According to the Modified Ashcroft scale scoring method, the degree of pulmonary fibrosis was evaluated according to the range of lesions and could be divided into 0 to 8 grades. The evaluation indexes for determining the degree of pulmonary fibrosis are as follows: grade 0: no pulmonary fibrosis occurred; grade 1: mild alveolar septum thickening, and the degree of thickening does not exceed 3 times the standard of grade 0, some alveolar structure become enlarged and loose, and with some alveolar septum rupture; grade 2: the alveolar septum is thickened, and the degree of thickening exceeds 3 times the standard of grade 0, some of alveolar structure become enlarged and loose and with some alveolar septum rupture, isolated nodules are formed but not related to each other; grade 3: the alveolar septum is thickened, and the degree of thickening exceeds 3 times the standard of grade 0, most of alveolar structure become enlarged and loose, isolated nodules are formed and linked to each other; grade 4: alveolar septum varies, single fibrotic masses are formed, and the area of the fibrotic mass is less than 10% of microscopic field; grade 5: alveolar septum varies, fibrotic masses are formed and fused, the area of the fibrotic mass covers from 10% to 50% of microscopic field, the lung structure is severely damaged but sill preserved; grade 6: alveolar septum varies and mostly does not exist, fibrotic masses are formed and fused, and the area of the fibrotic mass is more than 50% of microscopic field, most of the lung structure disappeared; grade 7: alveolar septum disappears, the fibrotic masses are fused and obliterate the alveolar, up to 5 air bubbles can be observed under a microscope; grade 8: alveolar septum does not exist, the fibrotic masses are fused and completely obliterate the alveolar. The result of the scale of pulmonary fibrosis (the result is shown in FIG. 16, and one-way ANOVA was used for biostatistical analysis) shows that: compared with the control group, there was an extremely significant pathological change of pulmonary fibrosis in the lung tissue in the model group (****: $p<0.0001$); compared with the model group, there were different degrees of significant alleviation in the pulmonary fibrosis lesions in rat lung tissue in the N4 to N11 treatment groups (†:$p<0.05$, ††:$p<0.01$, ††††: $p<0.0001$). The result shows that all of the N4 to N11 can inhibit pulmonary fibrosis in rats caused by bleomycin.

Example 15 Rat Model of Pulmonary Fibrosis and Treatment by Intratracheal Instillation Administration Route The rats in model group were intratracheally instilled with bleomycin (4 mg/kg); after anesthesia, the rats in treatment groups were intratracheally instilled with bleomycin (4 mg/kg) and corresponding therapeutic drug (8 mg/kg) simultaneously. The remaining implementation steps were the same as the description of Example 9.

Example 16 Determination of Rat Weight

The model and the administration route were referred to Example 15. The experimental rats in the control group, the model group, and the treatment groups described in Example 15 were weighted every day from the $1^{st}$ day until the $14^{th}$ day. When weighing, the "unstable weighing" of the electronic balance was selected, and an appropriate number of weighing and a degree of tolerable instability during the reading phase were set according to the instructions to weigh and record the readings. The result is shown in the weight ratios in FIG. 2 (Day 14/Day 0).

The result shows that: compared with the control group (abbreviated as C in Table 2), the weight growth rate of the rats in the model group (abbreviated as B in Table 2) decreased significantly; compared with the model group, the weight growth rate of rats in each of N1 to N54 treatment groups had different degrees of recovery, indicating that all of N1 to N54 can improve the decline of quality of life caused by bleomycin, and the therapeutic efficacy of N2 to N54 was better than that of the N1 treatment group.

Example 17 Determination of Lung Coefficient in Rat

The experimental rats of the control group, the model group and the treatment groups of Example 15 were taken to determine the lung coefficient. The implementation steps were the same as the description of Example 2. The result is shown in the lung coefficients in Table 2.

The result shows that: compared with the control group (abbreviated as C in Table 2), the lung coefficient of the rats in the model group (abbreviated as B in Table 2) increased significantly; compared with the model group, there were different degree of significant decrease in the lung coefficient of rats in each of N1 to N54 treatment groups, indicating that all of N1 to N54 can significantly inhibit pneumonedema and pulmonary fibrosis caused by bleomycin, and the therapeutic efficacy of N2 to N54 were all better than that of the N1 treatment group.

Example 18 HE Staining of Pathological Section of Rat Lung Tissue

Figure 17:
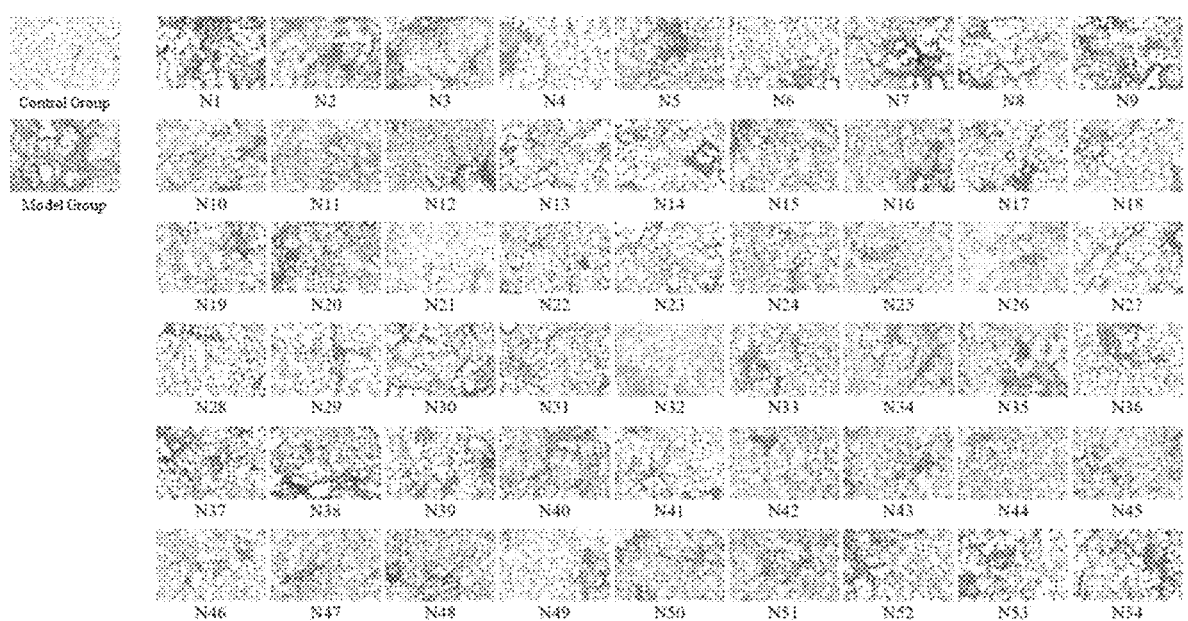
FIG. 17 shows the pathological examination (HE) of lung tissue of the experimental animals (the route of administration: intratracheal instillation)

The lung tissue of the rats of the control group, the model group and the treatment groups of Example 15 was taken and subjected to HE staining and scoring. The specific implementation steps and the evaluation method of the degree of alveolitis were the same as the description of Example 3. The HE staining result is shown in FIG. 17. The result of the inflammatory pathology score is shown in the HE score value in Table 2.

The results of HE staining and scoring show that: compared with the control group (abbreviated as C in Table 2), there were significant inflammatory pathological changes in the lung tissue in the model group (abbreviated as B in Table 2); compared with the rats in the model group, there were different degrees of significant alleviation in the inflammatory lesions in rat lung tissue in each of N1 to N54 treatment groups, indicating that all of N1 to N54 can significantly inhibit lung inflammation caused by bleomycin, and the therapeutic effect of N2 to N54 were all better than that of the N1 treatment group.

Example 19 Masson Staining of Pathological Section of Rat Lung Tissue

Figure 18:
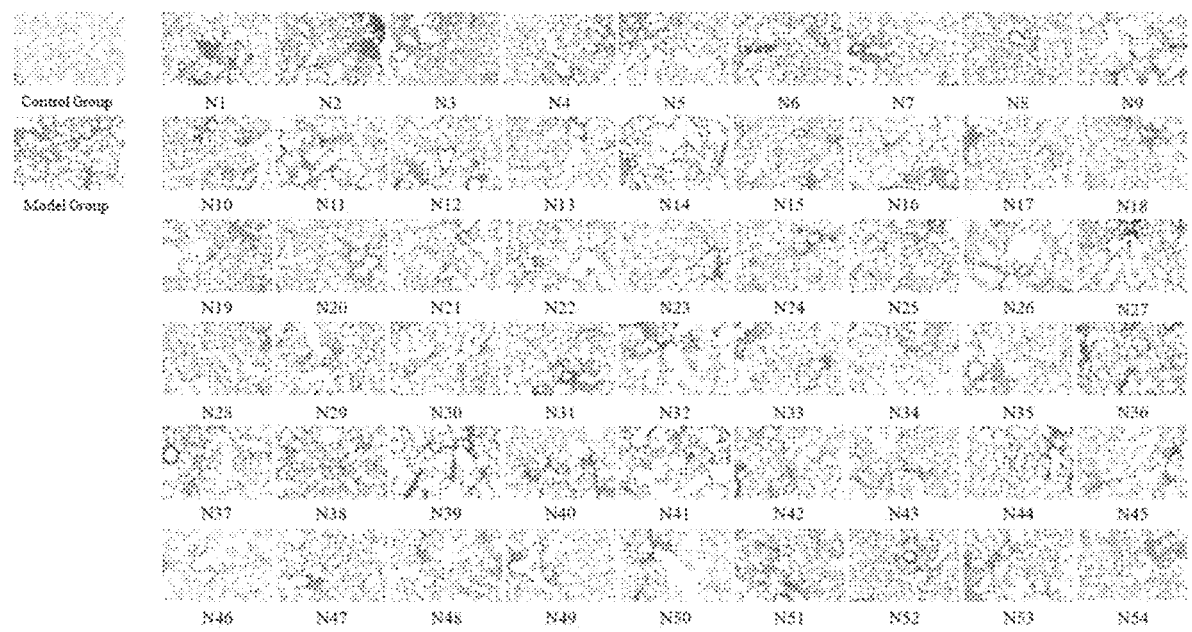
FIG. 18 shows the pathological examination (Masson) of lung tissue of the experimental animals (the route of administration: intratracheal instillation)

The lung tissue of the control group, the model group and the treatment groups of Example 15 was taken and subjected to Masson staining and scoring. The specific implementation steps were the same as the description of Example 13. The Masson staining result is shown in FIG. 18. The result of fibrosis pathology score is shown in the Masson score values in Table 2.

The results of Masson staining and scoring show that: compared with the control group (abbreviated as C in Table 2), there were extremely significant pathological changes in the lung tissue in the model group (abbreviated as B in Table 2); compared with the model group, there were different degrees of significant alleviation in lung fibrosis lesions in the rats in each of N1 to N54 treatment groups, indicating that all of N1 to N54 can significantly inhibit lung fibrosis lesions by bleomycin, and the therapeutic effects of N2 to N54 were all better than that of the N1 treatment group.

TABLE 2

Results of Weight Ratio, Lung Coefficient, HE Score, and Masson Score of Experimental Rats
(Route of Administration: intratracheal instillation) (Mean ± SEM)

| No. | Weight Ratio | Lung Coefficient | HE Score | Masson Score |
|---|---|---|---|---|
| C | 1.49 ± 0.02 | 4.61 ± 0.07 | 0.53 ± 0.08 | 0.45 ± 0.06 |
| N1 | 1.05 ± 0.02 | 8.49 ± 0.09 | 2.45 ± 0.09 | 3.93 ± 0.09 |
| N2 | 1.12 ± 0.06 | 8.15 ± 0.11 | 2.44 ± 0.05 | 3.88 ± 0.07 |
| N3 | 1.15 ± 0.02 | 7.39 ± 0.46 | 2.43 ± 0.34 | 3.86 ± 0.17 |
| N4 | 1.30 ± 0.05 | 6.44 ± 0.56 | 2.40 ± 0.48 | 3.80 ± 0.26 |
| N5 | 1.30 ± 0.10 | 6.61 ± 0.23 | 2.40 ± 0.33 | 3.80 ± 0.07 |
| N6 | 1.41 ± 0.04 | 5.42 ± 0.49 | 2.12 ± 0.32 | 3.45 ± 0.52 |
| N7 | 1.27 ± 0.06 | 6.68 ± 0.38 | 2.41 ± 0.32 | 3.81 ± 0.16 |
| N8 | 1.41 ± 0.06 | 5.43 ± 0.48 | 2.13 ± 0.37 | 3.45 ± 0.19 |
| N9 | 1.25 ± 0.07 | 6.79 ± 0.21 | 2.42 ± 0.25 | 3.83 ± 0.12 |
| N10 | 1.40 ± 0.02 | 5.48 ± 0.29 | 2.13 ± 0.10 | 3.48 ± 0.18 |
| N11 | 1.22 ± 0.05 | 7.08 ± 0.54 | 2.42 ± 0.32 | 3.83 ± 0.17 |
| N12 | 1.39 ± 0.02 | 5.49 ± 0.41 | 2.14 ± 0.11 | 3.49 ± 0.20 |
| N13 | 1.39 ± 0.03 | 5.52 ± 0.16 | 2.15 ± 0.48 | 3.53 ± 0.21 |
| N14 | 1.38 ± 0.02 | 5.53 ± 0.54 | 2.16 ± 0.38 | 3.54 ± 0.13 |
| N15 | 1.38 ± 0.01 | 5.53 ± 0.69 | 2.19 ± 0.44 | 3.56 ± 0.13 |
| N16 | 1.38 ± 0.05 | 5.55 ± 0.67 | 2.20 ± 0.38 | 3.57 ± 0.08 |
| N17 | 1.38 ± 0.06 | 5.61 ± 0.54 | 2.22 ± 0.34 | 3.58 ± 0.02 |
| N18 | 1.38 ± 0.02 | 5.62 ± 0.54 | 2.23 ± 0.13 | 3.60 ± 0.21 |
| N19 | 1.38 ± 0.02 | 5.65 ± 0.46 | 2.24 ± 0.06 | 3.60 ± 0.22 |
| N20 | 1.37 ± 0.04 | 5.69 ± 0.73 | 2.24 ± 0.56 | 3.60 ± 0.11 |
| N21 | 1.53 ± 0.01 | 4.39 ± 0.59 | 1.65 ± 0.16 | 2.22 ± 0.28 |
| N22 | 1.52 ± 0.07 | 4.41 ± 0.51 | 1.66 ± 0.26 | 2.94 ± 0.25 |
| N23 | 1.48 ± 0.07 | 4.45 ± 0.26 | 1.81 ± 0.25 | 2.99 ± 0.44 |
| N24 | 1.48 ± 0.04 | 4.50 ± 0.11 | 1.83 ± 0.12 | 3.00 ± 0.53 |
| N25 | 1.47 ± 0.07 | 4.56 ± 0.35 | 1.85 ± 0.16 | 3.03 ± 0.30 |
| N26 | 1.46 ± 0.01 | 4.58 ± 0.26 | 1.86 ± 0.42 | 3.11 ± 0.66 |
| N27 | 1.46 ± 0.06 | 4.59 ± 0.23 | 1.89 ± 0.39 | 3.16 ± 0.72 |
| B | 0.89 ± 0.04 | 9.86 ± 0.44 | 3.05 ± 0.08 | 4.41 ± 0.08 |
| N28 | 1.46 ± 0.04 | 4.65 ± 0.18 | 1.90 ± 0.46 | 3.19 ± 0.61 |
| N29 | 1.45 ± 0.03 | 4.68 ± 0.10 | 1.90 ± 0.24 | 3.23 ± 0.72 |
| N30 | 1.45 ± 0.03 | 4.69 ± 0.30 | 1.91 ± 0.19 | 3.26 ± 0.25 |
| N31 | 1.37 ± 0.04 | 5.71 ± 0.87 | 2.25 ± 0.12 | 3.61 ± 0.26 |
| N32 | 1.37 ± 0.08 | 5.72 ± 0.49 | 2.26 ± 0.18 | 3.62 ± 0.10 |
| N33 | 1.36 ± 0.07 | 5.81 ± 0.58 | 2.28 ± 0.16 | 3.62 ± 0.14 |
| N34 | 1.35 ± 0.05 | 5.83 ± 0.37 | 2.28 ± 0.43 | 3.63 ± 0.11 |
| N35 | 1.35 ± 0.07 | 5.85 ± 0.36 | 2.29 ± 0.44 | 3.70 ± 0.15 |
| N36 | 1.35 ± 0.08 | 5.86 ± 0.47 | 2.31 ± 0.32 | 3.70 ± 0.26 |
| N37 | 1.34 ± 0.07 | 5.92 ± 0.61 | 2.31 ± 0.26 | 3.70 ± 0.24 |
| N38 | 1.34 ± 0.05 | 5.95 ± 0.79 | 2.32 ± 0.16 | 3.71 ± 0.21 |
| N39 | 1.33 ± 0.12 | 5.96 ± 0.22 | 2.35 ± 0.18 | 3.71 ± 0.27 |
| N40 | 1.33 ± 0.02 | 6.02 ± 0.75 | 2.36 ± 0.13 | 3.72 ± 0.11 |
| N41 | 1.44 ± 0.04 | 4.81 ± 0.55 | 1.94 ± 0.33 | 3.26 ± 0.42 |
| N42 | 1.44 ± 0.09 | 4.92 ± 0.38 | 1.96 ± 0.17 | 3.27 ± 0.08 |
| N43 | 1.43 ± 0.03 | 4.97 ± 0.33 | 1.96 ± 0.42 | 3.28 ± 0.14 |
| N44 | 1.42 ± 0.04 | 4.99 ± 0.56 | 1.96 ± 0.13 | 3.31 ± 0.24 |
| N45 | 1.42 ± 0.04 | 5.04 ± 0.61 | 2.00 ± 0.43 | 3.31 ± 0.57 |
| N46 | 1.42 ± 0.03 | 5.08 ± 0.41 | 2.01 ± 0.07 | 3.36 ± 0.05 |
| N47 | 1.42 ± 0.07 | 5.09 ± 0.55 | 2.02 ± 0.40 | 3.38 ± 0.14 |
| N48 | 1.41 ± 0.04 | 5.09 ± 0.32 | 2.04 ± 0.44 | 3.39 ± 0.24 |
| N49 | 1.41 ± 0.02 | 5.18 ± 0.47 | 2.08 ± 0.25 | 3.40 ± 0.25 |
| N50 | 1.41 ± 0.06 | 5.21 ± 0.55 | 2.12 ± 0.54 | 3.44 ± 0.19 |
| N51 | 1.32 ± 0.07 | 6.10 ± 0.38 | 2.36 ± 0.52 | 3.74 ± 0.30 |
| N52 | 1.31 ± 0.13 | 6.11 ± 0.77 | 2.38 ± 0.33 | 3.75 ± 0.25 |
| N53 | 1.31 ± 0.02 | 6.12 ± 0.28 | 2.38 ± 0.55 | 3.78 ± 0.19 |
| N54 | 1.30 ± 0.08 | 6.39 ± 0.71 | 2.39 ± 0.24 | 3.78 ± 0.20 |

Example 20 Rat Model of Pulmonary Fibrosis and Treatment by Intravenous Injection Administration Route The rats were weighed before administration, intramuscularly injected with 65 mg/kg Zoletil anesthetic solution. After the rats entered the stage III anesthesia, the experimental rats were fixated in the lateral decubitus. Gavage needle size 12 was inserted into rat trachea through oral cavity along the glottis to instill sterile saline or bleomycin (4 mg/kg) (Day 0). After the anesthesia, the rats in control group were intratracheally instilled with an equal volume of sterile saline, and the rats in model group and treatment groups were intratracheally instilled with bleomycin (4 mg/kg). On the $4^{th}$ day, the sterile saline or peptide drug was injected through the tail vein once a day until the $13^{th}$ day. The rats were sacrificed on the $14^{th}$ day for subsequent experiments. The rats in the control group were received no drug treatment; the rats in the model group were injected with sterile saline through the tail vein; the rats in the treatment groups were injected with corresponding peptide drug (10 mg/kg) through the tail vein. All of the experimental animals were fed normally from the $1^{st}$ day to the $14^{th}$ day, and were weighed every day with feed and water ad libitum.

Example 21 Determination of Rat Body Weight

The model and the administration route were referred to Example 20. The experimental rats in the control group, the model group, and the treatment groups described in Example 20 were weighted every day from the $1^{st}$ day until the $14^{th}$ day. The method of determination of body weight was the same as the description of Example 16. The result is shown in the weight ratios in FIG. 3 (Day 14/Day 0).

The result shows that: compared with the control group (abbreviated as C in Table 3), the weight growth rate of the rats in the model group (abbreviated as B in Table 3) decreased significantly; compared with the model group, the body weight growth rate of rats in each of N1 to N54 treatment groups had different degrees of recovery, indicating that intravenous injection of any of the ingredients of N1 to N54 can improve the decline of life quality caused by bleomycin, and the therapeutic efficacy of N2 to N54 were all better than that of the N1 treatment group.

Example 22 Determination of Lung Coefficient in Rat

The experimental rats of the control group, the model group and the treatment groups of Example 20 were taken, the lung weight was measured and the lung coefficient was calculated. The specific implementation steps were the same as the description of Example 2. The result is shown in the lung coefficient in Table 3.

The result shows that: compared with the control group (abbreviated as C in Table 3), the lung coefficient of the rats in the model group (abbreviated as B in Table 3) increased significantly; compared with the model group, there were different degrees of significant decrease in the lung coefficient of rats in each of N1 to N54 treatment groups, indicating that intravenous injection of any of the ingredients of N1 to N54 can significantly inhibit pulmonary edema and pulmonary fibrosis caused by bleomycin in rats, and the therapeutic efficacy of N2 to N54 were all better than that of the N1 treatment group.

Example 23 HE Staining of Pathological Section of Rat Lung Tissue

Figure 19:
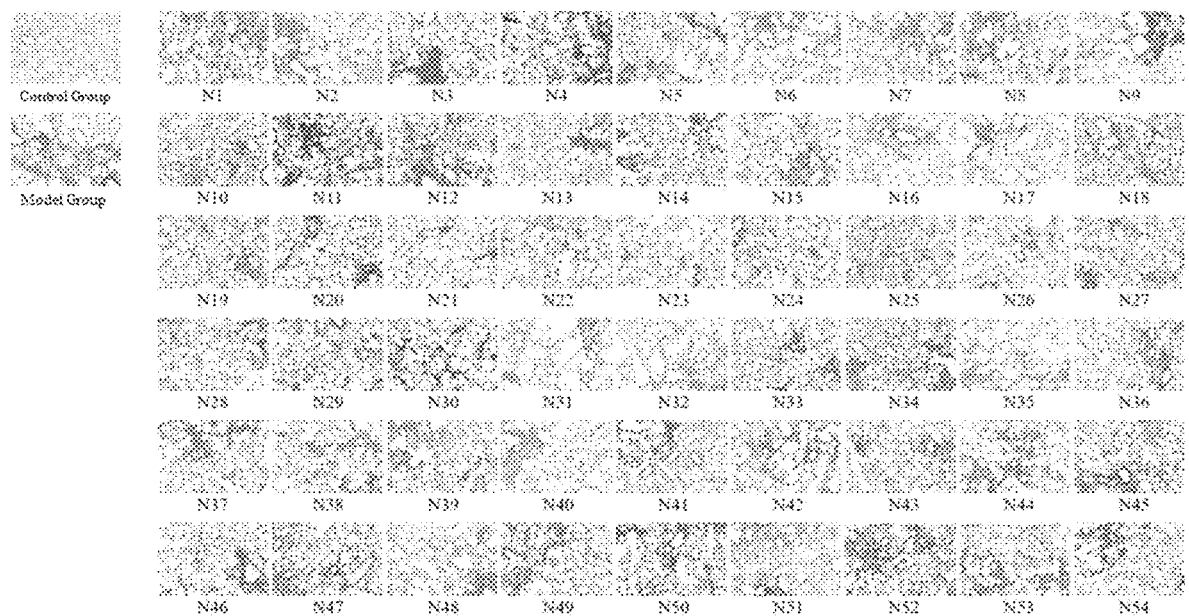
FIG. 19 shows the pathological examination (HE) of lung tissue of the experimental animals (the route of administration: intravenous injection)
Figure 20:
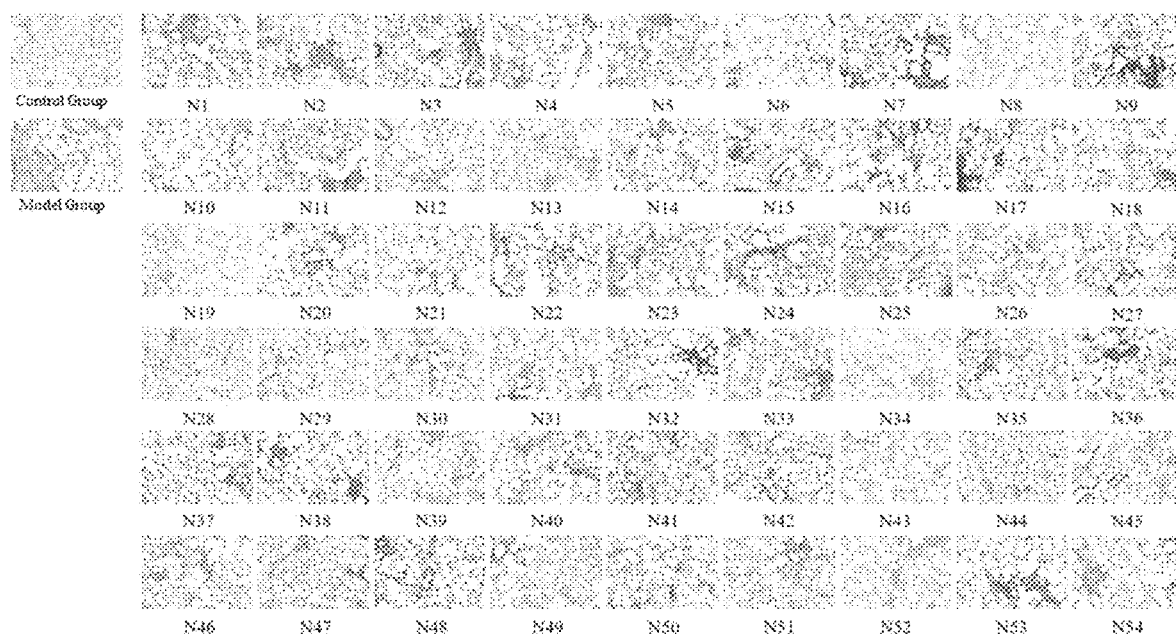
FIG. 20 shows the pathological examination (Masson) of lung tissue of the experimental animals (the route of administration: intravenous injection)

The lung tissue of the control group, the model group and the treatment groups of Example 20 was taken and subjected to HE staining and scoring. The specific implementation steps were the same as the description of Example 3. The HE staining result is shown in FIG. 19. The result of the inflammatory pathology score is shown in the HE score value in Table 3.

The results of HE staining and scoring show that: compared with the control group (abbreviated as C in Table 3), there were significant inflammatory pathological changes in the lung tissue in the model group (abbreviated as B in Table 3); compared with the rats in the model group, there were different degrees of significant alleviation of the inflammatory lesions in rat lung tissue in each of N1 to N54 treatment groups, indicating that intravenous injection of any of the ingredients of N1 to N54 can significantly inhibit lung inflammation caused by bleomycin, and the therapeutic effects of N2 to N54 were all better than that of the N1 treatment group.

Example 24 Masson Staining of Pathological Section of Rat Lung Tissue

The lung tissue of the control group, the model group and the treatment groups of Example 20 was taken and subjected to Masson staining and scoring. The implementation steps were the same as the description of Example 13. The Masson staining result is shown in FIG. 18. The result of fibrosis pathology score is shown in the Masson score values in Table 3.

The results of Masson staining and scoring show that: compared with the control group (abbreviated as C in Table 3), there were extremely significant pathological changes in the lung tissue in the model group (abbreviated as B in Table 3); compared with the model group, there were different degrees of significant improvements of lung fibrosis lesions in the rats in each of N1 to N54 treatment groups, indicating that intravenous injection of any of the components of N1 to N54 could significantly inhibit lung fibrosis lesions caused by bleomycin, and the therapeutic effects of N2 to N54 were all better than that of the N1 treatment group.

TABLE 3

Results of Weight Ratio, Lung Coefficient, HE Score, and Masson Score of Experimental Rats
(Route of Administration: intravenous injection) (Mean ± SEM)

| No. | Weight Ratio | Lung Coefficient | HE Score | Masson Score |
| --- | --- | --- | --- | --- |
| C | 1.55 ± 0.02 | 4.40 ± 0.09 | 0.53 ± 0.07 | 0.47 ± 0.12 |
| N1 | 1.05 ± 0.02 | 9.25 ± 0.28 | 2.44 ± 0.24 | 3.85 ± 0.11 |
| N2 | 1.12 ± 0.06 | 9.03 ± 0.36 | 2.44 ± 0.15 | 3.83 ± 0.06 |
| N3 | 1.15 ± 0.02 | 8.94 ± 0.41 | 2.42 ± 0.20 | 3.83 ± 0.03 |
| N4 | 1.30 ± 0.05 | 8.16 ± 0.45 | 2.38 ± 0.27 | 3.73 ± 0.16 |
| N5 | 1.30 ± 0.10 | 8.26 ± 0.34 | 2.39 ± 0.32 | 3.74 ± 0.03 |
| N6 | 1.41 ± 0.04 | 6.88 ± 0.92 | 2.04 ± 0.21 | 3.42 ± 0.52 |
| N7 | 1.27 ± 0.06 | 8.35 ± 0.40 | 2.39 ± 0.29 | 3.75 ± 0.17 |
| N8 | 1.41 ± 0.06 | 6.90 ± 0.31 | 2.04 ± 0.11 | 3.43 ± 0.29 |
| N9 | 1.25 ± 0.07 | 8.35 ± 0.48 | 2.41 ± 0.35 | 3.78 ± 0.16 |
| N10 | 1.40 ± 0.02 | 6.90 ± 0.74 | 2.08 ± 0.13 | 3.44 ± 0.38 |
| N11 | 1.22 ± 0.05 | 8.81 ± 0.14 | 2.42 ± 0.22 | 3.82 ± 0.14 |
| N12 | 1.39 ± 0.02 | 6.97 ± 1.24 | 2.08 ± 0.22 | 3.45 ± 0.18 |
| N13 | 1.39 ± 0.03 | 7.15 ± 0.60 | 2.11 ± 0.22 | 3.45 ± 0.50 |
| N14 | 1.38 ± 0.02 | 7.19 ± 1.08 | 2.12 ± 0.29 | 3.47 ± 0.18 |
| N15 | 1.38 ± 0.01 | 7.21 ± 1.22 | 2.14 ± 0.49 | 3.48 ± 0.25 |
| N16 | 1.38 ± 0.05 | 7.22 ± 1.15 | 2.14 ± 0.27 | 3.50 ± 0.14 |
| N17 | 1.38 ± 0.06 | 7.25 ± 0.97 | 2.15 ± 0.23 | 3.51 ± 0.13 |
| N18 | 1.38 ± 0.02 | 7.25 ± 1.48 | 2.16 ± 0.27 | 3.53 ± 0.28 |
| N19 | 1.38 ± 0.02 | 7.26 ± 1.03 | 2.17 ± 0.40 | 3.54 ± 0.30 |
| N20 | 1.37 ± 0.04 | 7.27 ± 0.64 | 2.21 ± 0.30 | 3.54 ± 0.23 |
| N21 | 1.53 ± 0.01 | 4.67 ± 0.26 | 1.57 ± 0.30 | 2.62 ± 0.42 |
| N22 | 1.52 ± 0.07 | 5.13 ± 0.50 | 1.63 ± 0.45 | 3.05 ± 0.48 |
| N23 | 1.49 ± 0.09 | 5.49 ± 0.11 | 1.65 ± 0.24 | 3.12 ± 0.54 |
| N24 | 1.48 ± 0.04 | 5.67 ± 0.52 | 1.69 ± 0.37 | 3.14 ± 0.46 |
| N25 | 1.47 ± 0.07 | 5.68 ± 0.44 | 1.76 ± 0.35 | 3.14 ± 0.39 |
| N26 | 1.46 ± 0.01 | 5.80 ± 0.65 | 1.81 ± 0.09 | 3.17 ± 0.70 |
| N27 | 1.46 ± 0.06 | 5.83 ± 0.53 | 1.85 ± 0.35 | 3.21 ± 0.37 |
| B | 0.89 ± 0.04 | 10.53 ± 0.65 | 3.02 ± 0.07 | 4.45 ± 0.08 |
| N28 | 1.46 ± 0.04 | 6.02 ± 0.54 | 1.85 ± 0.16 | 3.23 ± 0.58 |
| N29 | 1.45 ± 0.03 | 6.02 ± 0.97 | 1.91 ± 0.34 | 3.23 ± 0.30 |
| N30 | 1.45 ± 0.03 | 6.03 ± 0.65 | 1.91 ± 0.32 | 3.26 ± 0.11 |
| N31 | 1.37 ± 0.04 | 7.27 ± 1.20 | 2.21 ± 0.04 | 3.56 ± 0.13 |
| N32 | 1.37 ± 0.08 | 7.30 ± 1.60 | 2.22 ± 0.59 | 3.57 ± 0.37 |
| N33 | 1.35 ± 0.05 | 7.37 ± 1.31 | 2.23 ± 0.40 | 3.57 ± 0.29 |
| N34 | 1.35 ± 0.07 | 7.40 ± 0.68 | 2.24 ± 0.18 | 3.59 ± 0.34 |
| N35 | 1.35 ± 0.08 | 7.49 ± 0.20 | 2.28 ± 0.17 | 3.60 ± 0.21 |
| N36 | 1.34 ± 0.07 | 7.49 ± 0.77 | 2.30 ± 0.08 | 3.61 ± 0.29 |
| N37 | 1.34 ± 0.05 | 7.56 ± 0.88 | 2.31 ± 0.14 | 3.63 ± 0.27 |
| N38 | 1.33 ± 0.12 | 7.64 ± 1.32 | 2.32 ± 0.19 | 3.64 ± 0.15 |
| N39 | 1.33 ± 0.09 | 7.68 ± 0.88 | 2.34 ± 0.28 | 3.67 ± 0.33 |
| N40 | 1.33 ± 0.01 | 7.68 ± 0.31 | 2.35 ± 0.21 | 3.68 ± 0.19 |
| N41 | 1.44 ± 0.04 | 6.16 ± 0.42 | 1.91 ± 0.33 | 3.27 ± 0.62 |
| N42 | 1.44 ± 0.09 | 6.16 ± 0.42 | 1.94 ± 0.31 | 3.28 ± 0.33 |
| N43 | 1.43 ± 0.03 | 6.29 ± 0.85 | 1.95 ± 0.49 | 3.29 ± 0.07 |
| N44 | 1.42 ± 0.04 | 6.36 ± 0.85 | 1.96 ± 0.11 | 3.33 ± 0.35 |
| N45 | 1.42 ± 0.04 | 6.50 ± 0.90 | 1.97 ± 0.19 | 3.33 ± 0.23 |
| N46 | 1.42 ± 0.03 | 6.55 ± 0.41 | 1.98 ± 0.39 | 3.36 ± 0.11 |
| N47 | 1.42 ± 0.07 | 6.63 ± 0.81 | 1.98 ± 0.27 | 3.40 ± 0.10 |
| N48 | 1.41 ± 0.04 | 6.75 ± 1.14 | 1.98 ± 0.01 | 3.40 ± 0.22 |
| N49 | 1.41 ± 0.02 | 6.80 ± 1.21 | 1.99 ± 0.33 | 3.41 ± 0.20 |
| N50 | 1.41 ± 0.06 | 6.83 ± 0.61 | 2.03 ± 0.12 | 3.41 ± 0.35 |
| N51 | 1.32 ± 0.07 | 7.70 ± 0.58 | 2.35 ± 0.27 | 3.69 ± 0.14 |
| N52 | 1.31 ± 0.13 | 7.84 ± 0.81 | 2.35 ± 0.32 | 3.70 ± 0.18 |
| N53 | 1.31 ± 0.02 | 7.87 ± 0.32 | 2.37 ± 0.25 | 3.72 ± 0.23 |
| N54 | 1.30 ± 0.08 | 8.01 ± 0.32 | 2.37 ± 0.06 | 3.72 ± 0.29 |

Example 25 Detection of Hydroxyproline Content in Rat Lung Tissue by Acid Hydrolysis Method The lung tissue in the model group, the control group and the treatment groups of Example 20 was taken, and the hydroxyproline content in lung tissue was detected using BioVision Hydroxyproline Acid Hydrolysis Assay Kit (Cat. No. K555-100), the result is shown in the HYP values in Table 4.

The result shows that: compared with the control group (abbreviated as C in Table 4), the hydroxyproline content in lung tissue in the model group (abbreviated as B in Table 4)

increased significantly; compared with the model group, there were different degrees of significant decrease of the hydroxyproline content in lung tissue in each of N1 to N54 treatment groups, indicating that intravenous injection of any of the ingredients of N1 to N54 can significantly inhibit lung fibrosis caused by bleomycin, and the therapeutic effects of N2 to N54 were all better than that of the N1 treatment group.

Example 26 Detection of mRNA Content of tgf-β in Rat Lung Tissue By qPCR Method

The rat lung tissue in the control group, the model group and the treatment groups of Example 20 was taken. RNA in lung tissue was extracted using TRIZOL method. After obtaining cDNA using reverse transcription, fluorescence quantitative PCR (qPCR) kit (Applied Biosystems, Cat. No. 4319413E) was used to detect the mRNA content of tgf-β (forward primer: GAGGTGACCTGGGCACCAT, reverse primer: GGCCATGAGGAGCAGGAA), 18S RNA was used as an internal reference, and the result is shown in the tgf-β values in Table 4.

The result shows that: compared with the control group (abbreviated as C in Table 4), the mRNA content of rat tgf-β in the model group (abbreviated as B in Table 4) increased significantly; compared with the model group, there were different degrees of significant decrease in the mRNA content of rat tgf-β in each of N1 to N54 treatment groups, indicating that intravenous injection of any of the ingredients of N1 to N54 can significantly inhibit tgf-β gene expression caused by bleomycin, and the therapeutic effects of N2 to N54 were all better than that of the N1 treatment group.

Example 27 Detection of Active TGF-β Content in Rat Lung Tissue By ELISA

The rat lung tissue in the model group, the control group and the treatment groups of Example 20 was taken, and the active TGF-β content was measured by ELISA. The specific implementation steps were the same as the description of Example 9. The result is shown in the active TGF-β contents in Table 4 (active TGF-β/total TGF-β).

Compared with the control group (abbreviated as C in Table 4), the active TGF-β content in rat lung tissue in the model group (abbreviated as B in Table 4) increased significantly; compared with the model group, there were different degrees of significant decrease in the active TGF-β content in rat lung tissue in each of N1 to N54 treatment groups, indicating that intravenous injection of any of the ingredients of N1 to N54 can significantly inhibit TGF-β activation caused by bleomycin, and the therapeutic effects of N2 to N54 were all better than that of the N1 treatment group.

TABLE 4

The Contents of HYP, mRNA of TGF-β (tgf-β), and the Active TGF-β protein in Experimental Rat Lung Tissue (Route of Administration: Intravenous Injection) (Mean ± SEM)

| No. | HYP | tgf-β | TGF-β |
|---|---|---|---|
| C | 8.82 ± 0.15 | 0.73 ± 0.11 | 5.89 ± 0.54 |
| N1 | 34.09 ± 5.01 | 2.50 ± 0.04 | 13.15 ± 0.48 |
| N2 | 30.19 ± 2.78 | 2.23 ± 0.12 | 12.85 ± 0.63 |
| N3 | 30.18 ± 4.67 | 2.13 ± 0.16 | 12.64 ± 0.75 |
| N4 | 28.63 ± 1.89 | 2.06 ± 0.42 | 12.27 ± 0.04 |
| N5 | 28.84 ± 2.46 | 2.06 ± 0.41 | 12.31 ± 0.85 |
| N6 | 19.27 ± 2.59 | 1.58 ± 0.41 | 8.38 ± 0.56 |
| N7 | 29.12 ± 1.83 | 2.07 ± 0.03 | 12.37 ± 0.49 |
| N8 | 19.35 ± 1.16 | 1.61 ± 0.28 | 8.97 ± 0.31 |
| N9 | 29.67 ± 4.00 | 2.09 ± 0.37 | 12.47 ± 0.65 |
| N10 | 20.10 ± 2.97 | 1.62 ± 0.13 | 9.11 ± 0.22 |
| N11 | 29.82 ± 3.97 | 2.12 ± 0.10 | 12.48 ± 2.12 |
| N12 | 20.32 ± 2.87 | 1.70 ± 0.46 | 9.21 ± 0.23 |
| N13 | 20.32 ± 3.99 | 1.72 ± 0.40 | 9.35 ± 0.04 |
| N14 | 20.90 ± 3.25 | 1.72 ± 0.35 | 9.35 ± 0.53 |
| N15 | 21.50 ± 4.72 | 1.73 ± 0.17 | 9.53 ± 0.71 |
| N16 | 21.92 ± 4.56 | 1.75 ± 0.36 | 9.63 ± 0.79 |
| N17 | 22.41 ± 2.13 | 1.76 ± 0.36 | 9.99 ± 0.26 |
| N18 | 22.67 ± 2.65 | 1.78 ± 0.31 | 10.06 ± 0.34 |
| N19 | 22.68 ± 4.86 | 1.78 ± 0.44 | 10.11 ± 0.97 |
| N20 | 22.68 ± 3.58 | 1.80 ± 0.16 | 10.27 ± 0.55 |
| N21 | 14.12 ± 0.87 | 0.64 ± 0.04 | 5.58 ± 0.91 |
| N22 | 15.08 ± 1.44 | 0.98 ± 0.24 | 5.78 ± 0.26 |
| N23 | 15.33 ± 2.57 | 1.03 ± 0.04 | 5.84 ± 0.38 |
| N24 | 15.64 ± 2.12 | 1.03 ± 0.68 | 6.23 ± 0.44 |
| N25 | 16.30 ± 4.50 | 1.07 ± 0.36 | 6.45 ± 0.04 |
| N26 | 16.33 ± 1.91 | 1.09 ± 0.84 | 6.49 ± 0.41 |
| N27 | 16.49 ± 3.72 | 1.14 ± 0.65 | 6.58 ± 0.18 |
| B | 67.86 ± 11.16 | 3.45 ± 0.38 | 16.61 ± 1.16 |
| N28 | 16.75 ± 2.57 | 1.17 ± 0.57 | 6.78 ± 0.80 |
| N29 | 16.76 ± 3.66 | 1.18 ± 0.24 | 6.81 ± 0.86 |
| N30 | 16.87 ± 2.17 | 1.18 ± 0.28 | 6.85 ± 0.79 |
| N31 | 22.87 ± 2.12 | 1.81 ± 0.53 | 10.41 ± 0.97 |
| N32 | 22.96 ± 1.26 | 1.81 ± 0.23 | 10.48 ± 0.77 |
| N33 | 23.21 ± 2.93 | 1.82 ± 0.16 | 10.50 ± 0.45 |
| N34 | 23.81 ± 1.50 | 1.84 ± 0.08 | 10.78 ± 0.33 |
| N35 | 24.94 ± 1.20 | 1.89 ± 0.37 | 10.79 ± 0.44 |
| N36 | 25.53 ± 4.84 | 1.90 ± 0.25 | 10.79 ± 0.87 |
| N37 | 25.67 ± 1.72 | 1.90 ± 0.13 | 10.84 ± 0.22 |
| N38 | 26.22 ± 1.72 | 1.92 ± 0.15 | 10.95 ± 0.53 |
| N39 | 26.50 ± 2.98 | 1.92 ± 0.03 | 11.09 ± 0.50 |
| N40 | 26.82 ± 1.63 | 1.92 ± 0.03 | 11.83 ± 0.19 |
| N41 | 16.99 ± 4.53 | 1.20 ± 0.02 | 6.98 ± 0.90 |
| N42 | 17.68 ± 2.86 | 1.25 ± 0.16 | 7.11 ± 0.22 |
| N43 | 17.71 ± 3.75 | 1.28 ± 0.41 | 7.19 ± 0.21 |
| N44 | 17.81 ± 2.26 | 1.29 ± 0.15 | 7.28 ± 0.28 |
| N45 | 17.90 ± 1.44 | 1.35 ± 0.55 | 7.31 ± 0.71 |
| N46 | 17.92 ± 3.96 | 1.40 ± 0.26 | 7.52 ± 0.22 |
| N47 | 17.93 ± 3.65 | 1.46 ± 0.83 | 7.55 ± 0.15 |
| N48 | 18.46 ± 2.70 | 1.54 ± 0.60 | 7.92 ± 0.95 |
| N49 | 18.97 ± 1.12 | 1.54 ± 0.45 | 8.21 ± 0.98 |
| N50 | 19.04 ± 3.83 | 1.54 ± 0.34 | 8.24 ± 0.64 |
| N51 | 26.82 ± 2.20 | 1.93 ± 0.25 | 11.88 ± 0.77 |
| N52 | 27.19 ± 1.10 | 1.95 ± 0.07 | 12.02 ± 0.32 |
| N53 | 27.71 ± 2.38 | 1.98 ± 0.37 | 12.16 ± 0.40 |
| N54 | 28.37 ± 1.22 | 2.05 ± 0.38 | 12.18 ± 0.21 |

Example 28 Acute Toxicity Test

C57BL/6J mouse was used as experimental subject (purchased from Chengdu Dashuo Experimental Animal Co., Ltd., male, weighing 16 to 17 g). Sterile saline or polypeptide drug was injected through the tail vein once a day until the 13' day. The mice in control group were injected with sterile saline, the mice in treatment groups were injected with polypeptide drug (20 mg/kg). After the mice were sacrificed on the $14^{th}$ day, the brain, heart, liver, lung, kidney, and spleen were stripped for pathological examination (HE staining), and the results are shown in FIGS. 21 to 26.

Figure 21:
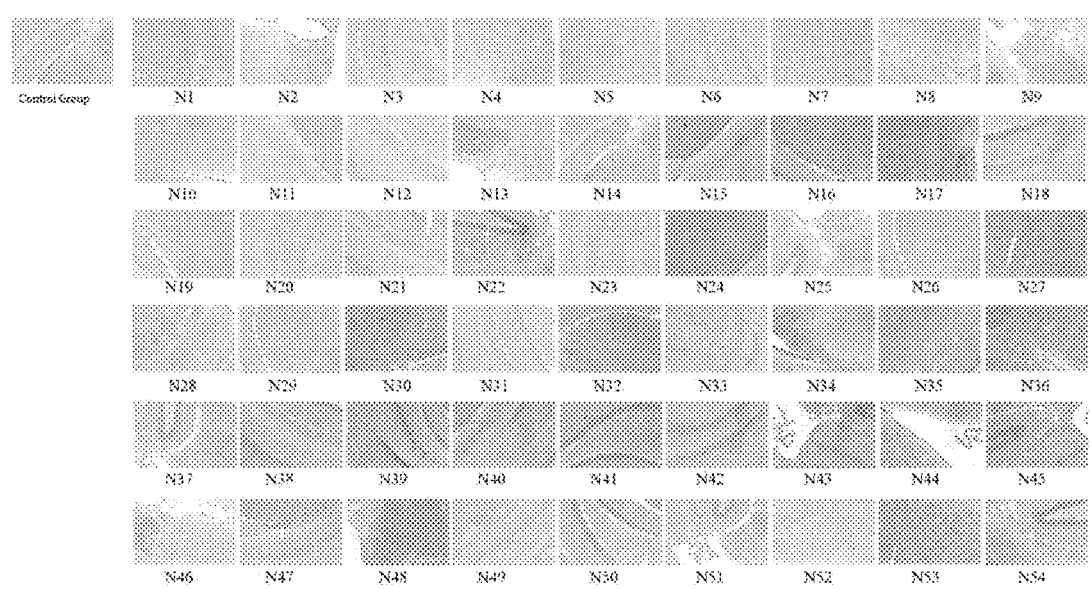
FIG. 21 shows the pathological examination (HE) of brain tissue of the experimental animals (the route of administration: intravenous injection)
Figure 22:
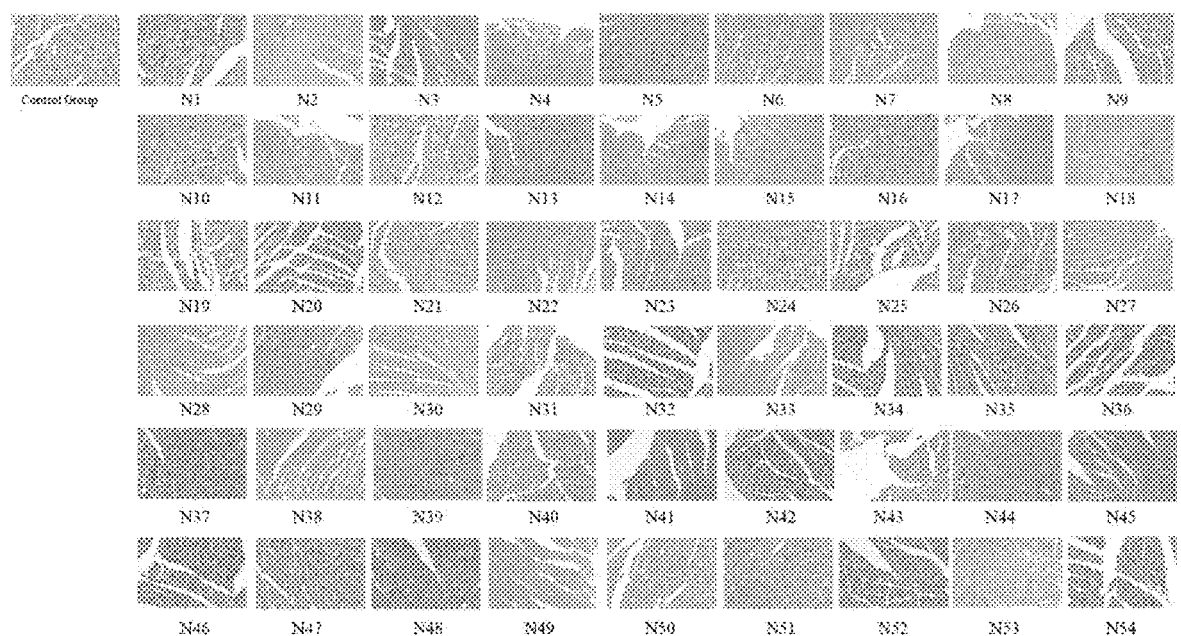
FIG. 22 shows the pathological examination (HE) of heart tissue of the experimental animals (the route of administration: intravenous injection)

FIG. 21 shows that: there was no significant difference between the staining results of each of the N1 to N54 drug administration groups and the control group, that is, the hippocampus neurons in the mouse brain were neatly orga- FIG. 22 shows that: there was no significant difference between the staining results of each of the N1 to N54 drug administration groups and the control group, that is, for the myocardial cells, there was no edema or hypertrophy, and there was no inflammatory cell infiltration, capillary and fibroblast proliferation or other pathological phenomenon.

Figure 23:
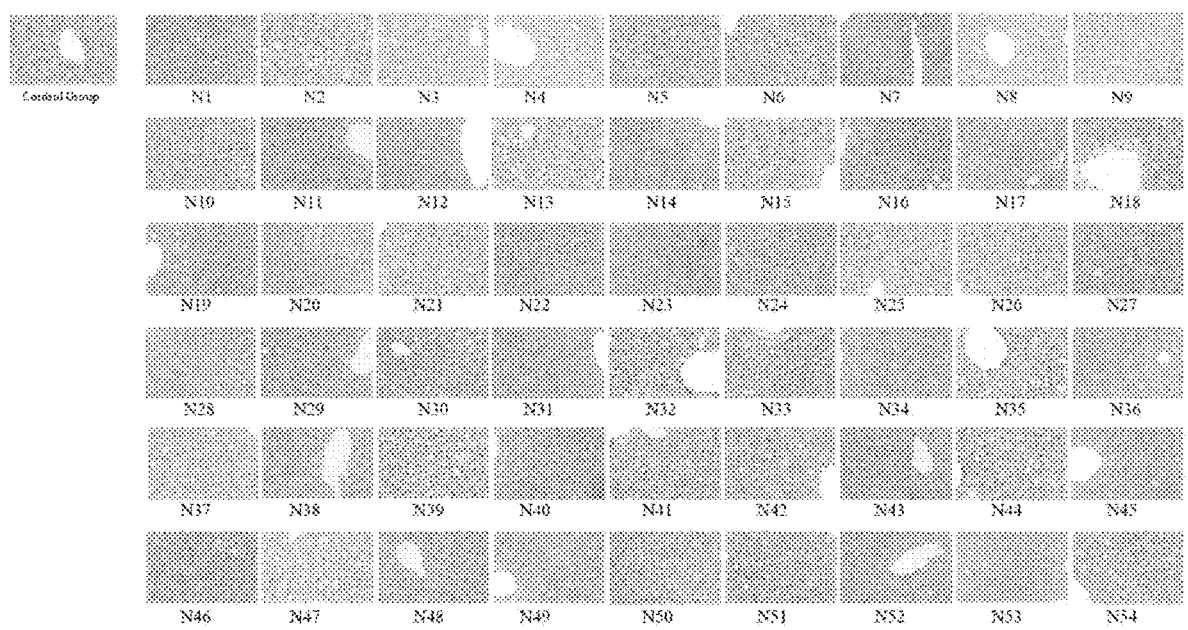
FIG. 23 shows the pathological examination (HE) of liver tissue of the experimental animals (the route of administration: intravenous injection)

FIG. 23 shows that: there was no significant difference between the staining results of each of the N1 to N54 drug administration groups and the control group, that is, the hepatocytes were arranged in a single row with the central vein as the center, and for the hepatocytes, there was no vacuolar degeneration or necrosis, and there was no inflammatory cell infiltration, marginal fibrosis or other pathological phenomenon.

Figure 24:
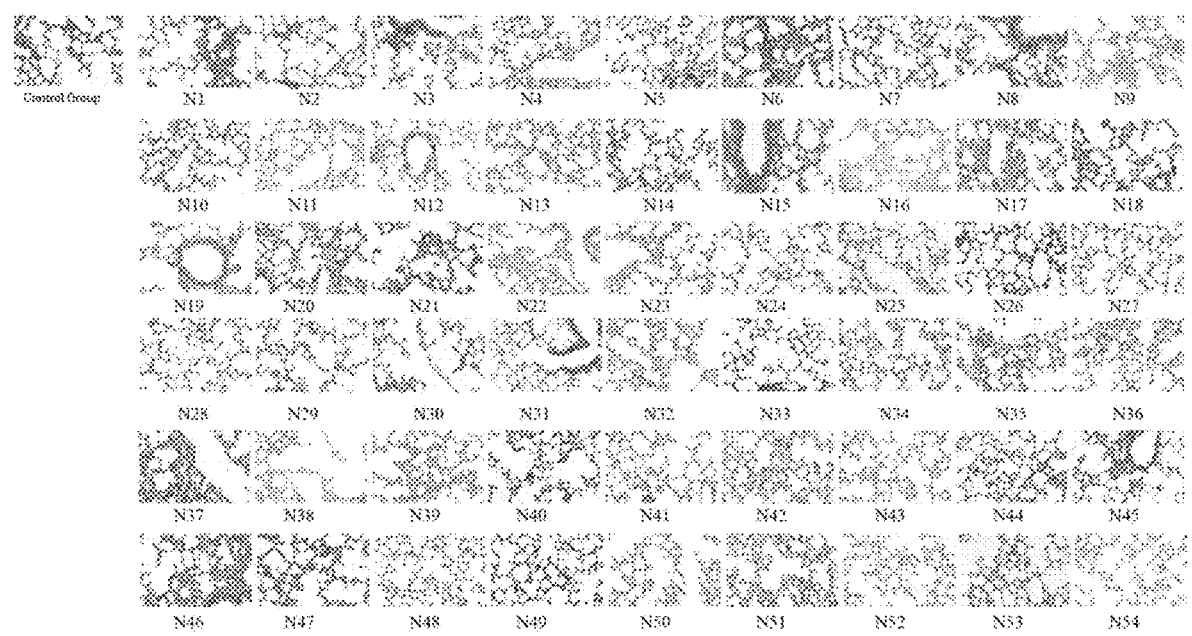
FIG. 24 shows a pathological examination (HE) of lung tissue of the experimental animals (the route of administration: intravenous injection)

FIG. 24 shows that: there was no significant difference between the staining results of each of the N1 to N54 drug administration groups and the control group, that is, the alveolar cavity was a vacuole-like thin-walled structure without thickening of the alveolar wall, inflammatory cell infiltration or other pathological phenomena.

Figure 25:
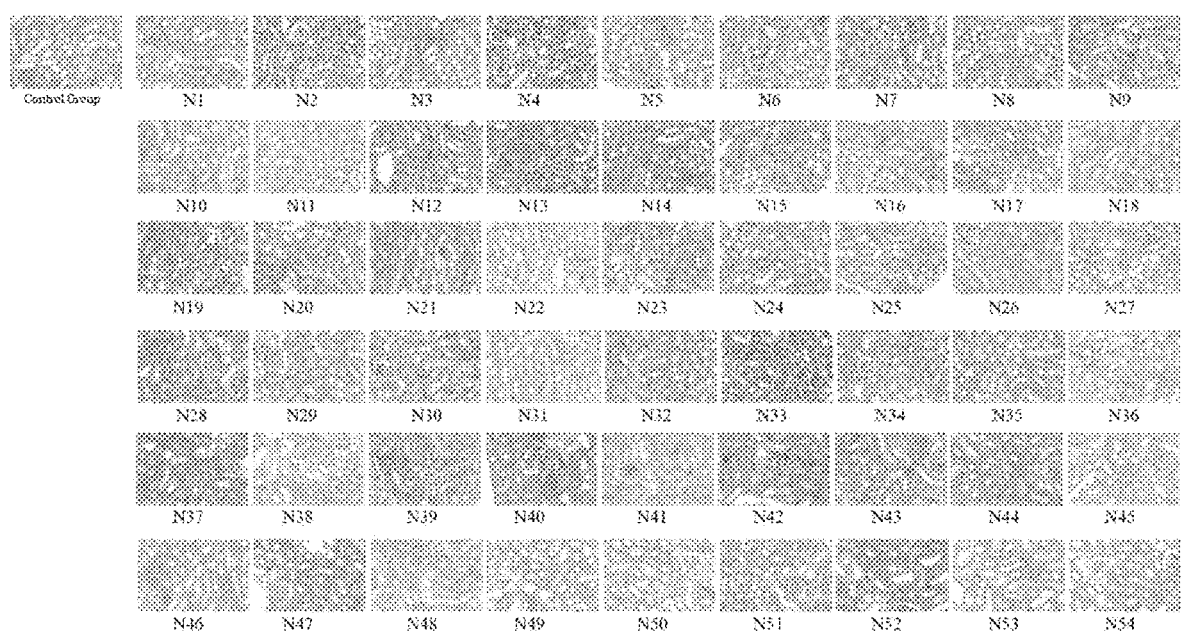
FIG. 25 shows the pathological examination (HE) of kidney tissue of the experimental animals (the route of administration: intravenous injection)

FIG. 25 shows that: there was no significant difference between the staining results of each of the N1 to N54 drug administration groups and the control group, that is, the structure of the glomerulus was clear, there was no granular degeneration, inflammatory cell infiltration, capillary congestion or other pathological phenomena.

Figure 26:
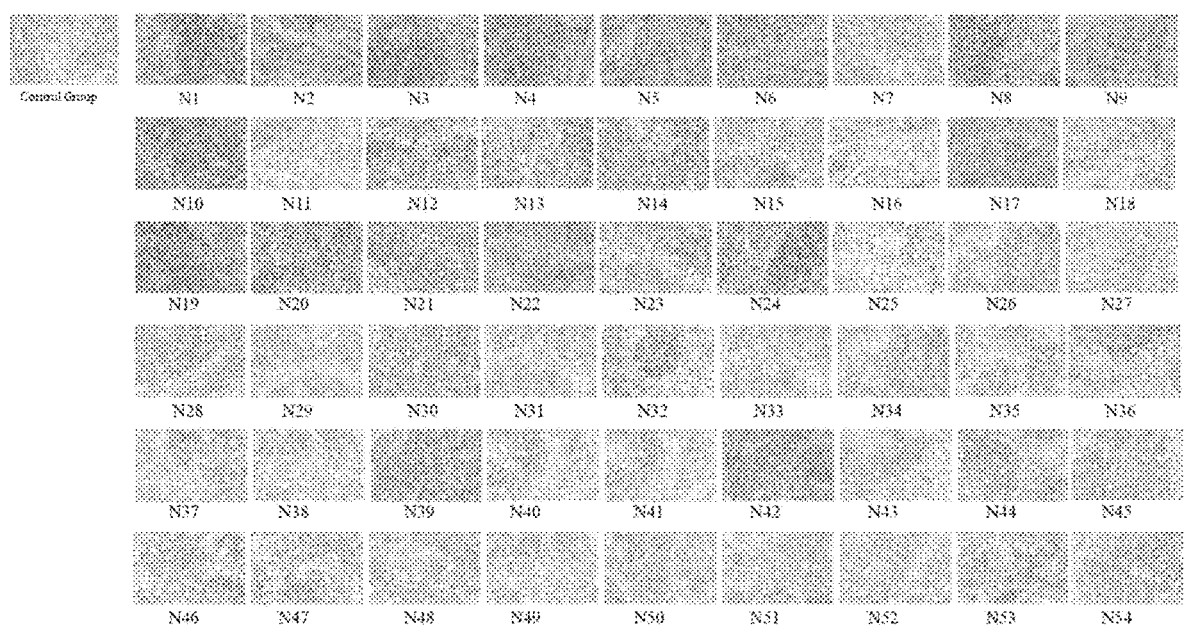
FIG. 26 shows the pathological examination (HE) of spleen tissue of the experimental animals (the route of administration: intravenous injection).

FIG. 26 shows that: there was no significant difference between the staining results of each of the N1 to N54 drug administration groups and the control group, that is, the structure of the spleen was intact, the splenic sinusoids were surrounded by the splenic cords, and connected to each other into a net, there was no thickening of the lymphatic sheath around the artery, no increasing in the number of spleen bodies or other pathological phenomena.

The result of the acute toxicity shows that intravenous injection of any ingredient of N1 to N54 did not produce associated organ toxicity in mice.

The above descriptions are only examples of the present invention, and do not limit the patent scope of the present invention. Any equivalent structure or equivalent process transformation, or directly or indirectly application to other related technical fields using the content of the patent specification of the present invention is equally included in the patent protection scope of the present invention.

The invention claimed is:

1. A polypeptide comprising the amino acid sequence of SEQ ID NO: 8.

2. The polypeptide according to claim 1, wherein the polypeptide has a modification and the modification is selected from the group consisting of polyethylene glycol modification, fatty acid modification, glycosylation modification, acetylation modifications, amidation modification, and phosphorylation modification.

3. A method of treating a fibrosis disease, comprising administering a subject in need thereof the polypeptide according to claim 1, wherein the fibrosis disease is pulmonary fibrosis.

4. The polypeptide according to claim 2, wherein the modification is polyethylene glycol modification.

5. The method according to claim 3, wherein the polypeptide is administered as a single active ingredient, or in combination with other drugs.

6. The method according to claim 3, wherein the polypeptide is administered via oral administration, pulmonary administration, nasal administration, transdermal administration, ocular administration, intravenous drip, intraperitoneal injection, subcutaneous injection, or intramuscular injection.

* * * * *

SEQUENCE LISTING

```
<160> NUMBER OF SEQ ID NOS: 54

<210> SEQ ID NO 1
<211> LENGTH: 18
<212> TYPE: PRT
<213> ORGANISM: Homo sapiens

<400> SEQUENCE: 1

Tyr Arg Val Arg Phe Leu Ala Lys Glu Asn Val Thr Gln Asp Ala Glu
1               5                   10                  15

Asp Asn

<210> SEQ ID NO 2
<211> LENGTH: 17
<212> TYPE: PRT
<213> ORGANISM: Homo sapiens

<400> SEQUENCE: 2

Tyr Arg Val Arg Phe Leu Ala Lys Glu Asn Val Thr Gln Asp Ala Glu
1               5                   10                  15

Asp

<210> SEQ ID NO 3
<211> LENGTH: 17
<212> TYPE: PRT
<213> ORGANISM: Homo sapiens
<220> FEATURE:
<221> NAME/KEY: MOD_RES
<222> LOCATION: (1)..(17)
<223> OTHER INFORMATION: PEG2 is linked to the N-terminus via an amide
      bond

<400> SEQUENCE: 3

Tyr Arg Val Arg Phe Leu Ala Lys Glu Asn Val Thr Gln Asp Ala Glu
1               5                   10                  15

Asp

<210> SEQ ID NO 4
```

```
<211> LENGTH: 11
<212> TYPE: PRT
<213> ORGANISM: Homo sapiens

<400> SEQUENCE: 4

Arg Phe Leu Ala Lys Glu Asn Val Thr Gln Asp
1               5                   10

<210> SEQ ID NO 5
<211> LENGTH: 16
<212> TYPE: PRT
<213> ORGANISM: Homo sapiens

<400> SEQUENCE: 5

Arg Phe Leu Ala Lys Glu Asn Val Thr Gln Asp Ala Glu Asp Asn Cys
1               5                   10                  15

<210> SEQ ID NO 6
<211> LENGTH: 14
<212> TYPE: PRT
<213> ORGANISM: Homo sapiens

<400> SEQUENCE: 6

Tyr Arg Val Arg Phe Leu Ala Lys Glu Asn Val Thr Gln Asp
1               5                   10

<210> SEQ ID NO 7
<211> LENGTH: 19
<212> TYPE: PRT
<213> ORGANISM: Homo sapiens

<400> SEQUENCE: 7

Tyr Arg Val Arg Phe Leu Ala Lys Glu Asn Val Thr Gln Asp Arg Glu
1               5                   10                  15

Asp Asn Cys

<210> SEQ ID NO 8
<211> LENGTH: 11
<212> TYPE: PRT
<213> ORGANISM: Homo sapiens

<400> SEQUENCE: 8

Tyr Arg Phe Leu Ala Lys Glu Asn Thr Gln Asp
1               5                   10

<210> SEQ ID NO 9
<211> LENGTH: 14
<212> TYPE: PRT
<213> ORGANISM: Homo sapiens
<220> FEATURE:
<221> NAME/KEY: MOD_RES
<222> LOCATION: (1)..(14)
<223> OTHER INFORMATION: PEG2 is linked to the N-terminus via an amide
      bond

<400> SEQUENCE: 9

Tyr Arg Val Arg Phe Leu Ala Lys Glu Asn Val Thr Gln Asp
1               5                   10

<210> SEQ ID NO 10
<211> LENGTH: 11
<212> TYPE: PRT
<213> ORGANISM: Homo sapiens
<220> FEATURE:
<221> NAME/KEY: MOD_RES
<222> LOCATION: (1)..(11)
```

```
<223> OTHER INFORMATION: PEG2 is linked to the N-terminus via an amide
      bond

<400> SEQUENCE: 10

Arg Phe Leu Ala Lys Glu Asn Val Thr Gln Asp
1               5                   10

<210> SEQ ID NO 11
<211> LENGTH: 11
<212> TYPE: PRT
<213> ORGANISM: Homo sapiens
<220> FEATURE:
<221> NAME/KEY: MOD_RES
<222> LOCATION: (1)..(11)
<223> OTHER INFORMATION: PEG2 is linked to the N-terminus via an amide
      bond

<400> SEQUENCE: 11

Arg Phe Leu Ala Lys Glu Asn Val Thr Gln Asp
1               5                   10

<210> SEQ ID NO 12
<211> LENGTH: 15
<212> TYPE: PRT
<213> ORGANISM: Homo sapiens

<400> SEQUENCE: 12

Val Arg Phe Leu Ala Lys Glu Asn Val Thr Gln Asp Ala Glu Asp
1               5                   10                  15

<210> SEQ ID NO 13
<211> LENGTH: 9
<212> TYPE: PRT
<213> ORGANISM: Homo sapiens

<400> SEQUENCE: 13

Leu Ala Lys Glu Asn Val Thr Gln Asp
1               5

<210> SEQ ID NO 14
<211> LENGTH: 14
<212> TYPE: PRT
<213> ORGANISM: Homo sapiens

<400> SEQUENCE: 14

Leu Ala Lys Glu Asn Val Thr Gln Asp Ala Glu Asp Asn Cys
1               5                   10

<210> SEQ ID NO 15
<211> LENGTH: 19
<212> TYPE: PRT
<213> ORGANISM: Homo sapiens

<400> SEQUENCE: 15

Tyr Arg Val Arg Phe Leu Ala Lys Glu Asn Val Thr Gln Asp Ala Glu
1               5                   10                  15

Asp Arg Cys

<210> SEQ ID NO 16
<211> LENGTH: 19
<212> TYPE: PRT
<213> ORGANISM: Homo sapiens

<400> SEQUENCE: 16

Tyr Arg Val Arg Phe Leu Arg Lys Glu Asn Val Thr Gln Asp Ala Glu
```

-continued

```
1               5                   10                  15

Asp Asn Cys

<210> SEQ ID NO 17
<211> LENGTH: 20
<212> TYPE: PRT
<213> ORGANISM: Homo sapiens

<400> SEQUENCE: 17

Tyr Arg Val Arg Phe Leu Ala Lys Glu Asn Val Thr Gln Asp Ala Glu
1               5                   10                  15

Asp Asn Cys Thr
            20

<210> SEQ ID NO 18
<211> LENGTH: 20
<212> TYPE: PRT
<213> ORGANISM: Homo sapiens

<400> SEQUENCE: 18

Phe Tyr Arg Val Arg Phe Leu Ala Lys Glu Asn Val Thr Gln Asp Ala
1               5                   10                  15

Glu Asp Asn Cys
            20

<210> SEQ ID NO 19
<211> LENGTH: 11
<212> TYPE: PRT
<213> ORGANISM: Homo sapiens

<400> SEQUENCE: 19

Leu Ala Lys Glu Asn Val Thr Gln Asp Arg Cys
1               5                   10

<210> SEQ ID NO 20
<211> LENGTH: 18
<212> TYPE: PRT
<213> ORGANISM: Homo sapiens

<400> SEQUENCE: 20

Arg Tyr Arg Val Arg Phe Leu Ala Lys Glu Asn Val Thr Gln Asp Ala
1               5                   10                  15

Glu Asp

<210> SEQ ID NO 21
<211> LENGTH: 10
<212> TYPE: PRT
<213> ORGANISM: Homo sapiens

<400> SEQUENCE: 21

Ser Leu Ala Lys Glu Asn Val Thr Gln Asp
1               5                   10

<210> SEQ ID NO 22
<211> LENGTH: 11
<212> TYPE: PRT
<213> ORGANISM: Homo sapiens

<400> SEQUENCE: 22

Arg Phe Leu Arg Lys Glu Asn Val Thr Gln Asp
1               5                   10
```

```
<210> SEQ ID NO 23
<211> LENGTH: 16
<212> TYPE: PRT
<213> ORGANISM: Homo sapiens

<400> SEQUENCE: 23

Tyr Arg Val Arg Phe Leu Arg Lys Glu Asn Thr Gln Asp Ala Glu Asp
1               5                   10                  15

<210> SEQ ID NO 24
<211> LENGTH: 15
<212> TYPE: PRT
<213> ORGANISM: Homo sapiens

<400> SEQUENCE: 24

Val Arg Phe Leu Arg Lys Glu Asn Val Thr Gln Asp Ala Glu Asp
1               5                   10                  15

<210> SEQ ID NO 25
<211> LENGTH: 20
<212> TYPE: PRT
<213> ORGANISM: Homo sapiens

<400> SEQUENCE: 25

Tyr Arg Val Arg Phe Leu Ala Lys Glu Asn Val Thr Gln Asp Ala Glu
1               5                   10                  15

Asp Arg Cys Thr
            20

<210> SEQ ID NO 26
<211> LENGTH: 20
<212> TYPE: PRT
<213> ORGANISM: Homo sapiens

<400> SEQUENCE: 26

Phe Tyr Arg Val Arg Phe Leu Ala Lys Glu Asn Val Thr Gln Asp Arg
1               5                   10                  15

Glu Asp Asn Cys
            20

<210> SEQ ID NO 27
<211> LENGTH: 19
<212> TYPE: PRT
<213> ORGANISM: Homo sapiens
<220> FEATURE:
<221> NAME/KEY: MOD_RES
<222> LOCATION: (1)..(19)
<223> OTHER INFORMATION: PEG2 is linked to the C-terminus via an amide
      bond

<400> SEQUENCE: 27

Tyr Arg Val Arg Phe Leu Ala Lys Glu Asn Val Thr Gln Asp Ala Glu
1               5                   10                  15

Asp Asn Cys

<210> SEQ ID NO 28
<211> LENGTH: 15
<212> TYPE: PRT
<213> ORGANISM: Homo sapiens
<220> FEATURE:
<221> NAME/KEY: MOD_RES
<222> LOCATION: (1)..(15)
<223> OTHER INFORMATION: PEG2 is linked to the N-terminus via an amide
      bond

<400> SEQUENCE: 28
```

Val Arg Phe Leu Ala Lys Glu Asn Val Thr Gln Asp Ala Glu Asp
1               5                   10                  15

<210> SEQ ID NO 29
<211> LENGTH: 9
<212> TYPE: PRT
<213> ORGANISM: Homo sapiens
<220> FEATURE:
<221> NAME/KEY: MOD_RES
<222> LOCATION: (1)..(9)
<223> OTHER INFORMATION: Xaa(1)= PEG2 is linked to the N-terminus via an
      amide bond

<400> SEQUENCE: 29

Leu Ala Lys Glu Asn Val Thr Gln Asp
1               5

<210> SEQ ID NO 30
<211> LENGTH: 9
<212> TYPE: PRT
<213> ORGANISM: Homo sapiens
<220> FEATURE:
<221> NAME/KEY: MOD_RES
<222> LOCATION: (1)..(9)
<223> OTHER INFORMATION: PEG2 is linked to the C-terminus via an amide
      bond

<400> SEQUENCE: 30

Leu Ala Lys Glu Asn Val Thr Gln Asp
1               5

<210> SEQ ID NO 31
<211> LENGTH: 11
<212> TYPE: PRT
<213> ORGANISM: Homo sapiens
<220> FEATURE:
<221> NAME/KEY: MOD_RES
<222> LOCATION: (1)..(11)
<223> OTHER INFORMATION: PEG2 is linked to the N-terminus via an amide
      bond

<400> SEQUENCE: 31

Tyr Arg Phe Leu Ala Lys Glu Asn Thr Gln Asp
1               5                   10

<210> SEQ ID NO 32
<211> LENGTH: 16
<212> TYPE: PRT
<213> ORGANISM: Homo sapiens
<220> FEATURE:
<221> NAME/KEY: MOD_RES
<222> LOCATION: (1)..(16)
<223> OTHER INFORMATION: PEG2 is linked to the C-terminus via an amide
      bond

<400> SEQUENCE: 32

Arg Phe Leu Ala Lys Glu Asn Val Thr Gln Asp Ala Glu Asp Asn Cys
1               5                   10                  15

<210> SEQ ID NO 33
<211> LENGTH: 14
<212> TYPE: PRT
<213> ORGANISM: Homo sapiens
<220> FEATURE:
<221> NAME/KEY: MOD_RES
<222> LOCATION: (1)..(14)
<223> OTHER INFORMATION: PEG2 is linked to the C-terminus via an amide
      bond

```
<400> SEQUENCE: 33

Leu Ala Lys Glu Asn Val Thr Gln Asp Ala Glu Asp Asn Cys
1               5                   10

<210> SEQ ID NO 34
<211> LENGTH: 19
<212> TYPE: PRT
<213> ORGANISM: Homo sapiens
<220> FEATURE:
<221> NAME/KEY: MOD_RES
<222> LOCATION: (1)..(19)
<223> OTHER INFORMATION: is linked to the N-terminus via an amide bond

<400> SEQUENCE: 34

Tyr Arg Val Arg Phe Leu Ala Lys Glu Asn Val Thr Gln Asp Arg Glu
1               5                   10                  15

Asp Asn Cys

<210> SEQ ID NO 35
<211> LENGTH: 19
<212> TYPE: PRT
<213> ORGANISM: Homo sapiens
<220> FEATURE:
<221> NAME/KEY: MOD_RES
<222> LOCATION: (1)..(19)
<223> OTHER INFORMATION: PEG2 is linked to the C-terminus via an amide
      bond

<400> SEQUENCE: 35

Tyr Arg Val Arg Phe Leu Ala Lys Glu Asn Val Thr Gln Asp Arg Glu
1               5                   10                  15

Asp Asn Cys

<210> SEQ ID NO 36
<211> LENGTH: 19
<212> TYPE: PRT
<213> ORGANISM: Homo sapiens
<220> FEATURE:
<221> NAME/KEY: MOD_RES
<222> LOCATION: (1)..(19)
<223> OTHER INFORMATION: PEG2 is linked to the C-terminus via an amide
      bond

<400> SEQUENCE: 36

Tyr Arg Val Arg Phe Leu Arg Lys Glu Asn Val Thr Gln Asp Ala Glu
1               5                   10                  15

Asp Asn Cys

<210> SEQ ID NO 37
<211> LENGTH: 20
<212> TYPE: PRT
<213> ORGANISM: Homo sapiens
<220> FEATURE:
<221> NAME/KEY: MOD_RES
<222> LOCATION: (1)..(20)
<223> OTHER INFORMATION: PEG2 is linked to the N-terminus via an amide
      bond

<400> SEQUENCE: 37

Tyr Arg Val Arg Phe Leu Ala Lys Glu Asn Val Thr Gln Asp Ala Glu
1               5                   10                  15

Asp Asn Cys Thr
            20

<210> SEQ ID NO 38
```

```
<211> LENGTH: 20
<212> TYPE: PRT
<213> ORGANISM: Homo sapiens
<220> FEATURE:
<221> NAME/KEY: MOD_RES
<222> LOCATION: (1)..(20)
<223> OTHER INFORMATION: PEG2 is linked to the C-terminus via an amide
      bond

<400> SEQUENCE: 38

Phe Tyr Arg Val Arg Phe Leu Ala Lys Glu Asn Val Thr Gln Asp Ala
1               5                   10                  15

Glu Asp Asn Cys
            20

<210> SEQ ID NO 39
<211> LENGTH: 20
<212> TYPE: PRT
<213> ORGANISM: Homo sapiens
<220> FEATURE:
<221> NAME/KEY: MOD_RES
<222> LOCATION: (1)..(20)
<223> OTHER INFORMATION: PEG2 is linked to the C-terminus via an amide
      bond

<400> SEQUENCE: 39

Tyr Arg Val Arg Phe Leu Ala Lys Glu Asn Val Thr Gln Asp Ala Glu
1               5                   10                  15

Asp Asn Thr Cys
            20

<210> SEQ ID NO 40
<211> LENGTH: 11
<212> TYPE: PRT
<213> ORGANISM: Homo sapiens
<220> FEATURE:
<221> NAME/KEY: MOD_RES
<222> LOCATION: (1)..(11)
<223> OTHER INFORMATION: PEG2 is linked to the N-terminus via an amide
      bond

<400> SEQUENCE: 40

Leu Ala Lys Glu Asn Val Thr Gln Asp Arg Cys
1               5                   10

<210> SEQ ID NO 41
<211> LENGTH: 18
<212> TYPE: PRT
<213> ORGANISM: Homo sapiens
<220> FEATURE:
<221> NAME/KEY: MOD_RES
<222> LOCATION: (1)..(18)
<223> OTHER INFORMATION: PEG2 is linked to the C-terminus via an amide
      bond

<400> SEQUENCE: 41

Arg Tyr Arg Val Arg Phe Leu Ala Lys Glu Asn Val Thr Gln Asp Ala
1               5                   10                  15

Glu Asp

<210> SEQ ID NO 42
<211> LENGTH: 10
<212> TYPE: PRT
<213> ORGANISM: Homo sapiens
<220> FEATURE:
<221> NAME/KEY: MOD_RES
<222> LOCATION: (1)..(10)
<223> OTHER INFORMATION: PEG2 is linked to the N-terminus via an amide
``` bond

<400> SEQUENCE: 42

Leu Ala Lys Glu Asn Val Thr Gln Asp Arg
1               5                   10

<210> SEQ ID NO 43
<211> LENGTH: 18
<212> TYPE: PRT
<213> ORGANISM: Homo sapiens
<220> FEATURE:
<221> NAME/KEY: MOD_RES
<222> LOCATION: (1)..(18)
<223> OTHER INFORMATION: PEG2 is linked to the C-terminus via an amide
      bond

<400> SEQUENCE: 43

Arg Tyr Arg Val Arg Phe Leu Ala Lys Glu Asn Val Thr Gln Asp Ala
1               5                   10                  15

Glu Asp

<210> SEQ ID NO 44
<211> LENGTH: 18
<212> TYPE: PRT
<213> ORGANISM: Homo sapiens
<220> FEATURE:
<221> NAME/KEY: MOD_RES
<222> LOCATION: (1)..(18)
<223> OTHER INFORMATION: PEG2 is linked to the C-terminus via an amide
      bond

<400> SEQUENCE: 44

Tyr Arg Ser Val Arg Phe Leu Ala Lys Glu Asn Val Thr Gln Asp Ala
1               5                   10                  15

Glu Asp

<210> SEQ ID NO 45
<211> LENGTH: 9
<212> TYPE: PRT
<213> ORGANISM: Homo sapiens
<220> FEATURE:
<221> NAME/KEY: MOD_RES
<222> LOCATION: (1)..(9)
<223> OTHER INFORMATION: PEG2 is linked to the C-terminus via an amide
      bond

<400> SEQUENCE: 45

Leu Ala Lys Glu Asn Arg Thr Gln Asp
1               5

<210> SEQ ID NO 46
<211> LENGTH: 16
<212> TYPE: PRT
<213> ORGANISM: Homo sapiens
<220> FEATURE:
<221> NAME/KEY: MOD_RES
<222> LOCATION: (1)..(16)
<223> OTHER INFORMATION: PEG2 is linked to the N-terminus via an amide
      bond

<400> SEQUENCE: 46

Tyr Arg Val Arg Phe Leu Arg Lys Glu Asn Thr Gln Asp Ala Glu Asp
1               5                   10                  15

<210> SEQ ID NO 47
<211> LENGTH: 17
<212> TYPE: PRT

```
<213> ORGANISM: Homo sapiens
<220> FEATURE:
<221> NAME/KEY: MOD_RES
<222> LOCATION: (1)..(17)
<223> OTHER INFORMATION: PEG2 is linked to the C-terminus via an amide
      bond

<400> SEQUENCE: 47

Val Arg Phe Leu Ala Lys Glu Asn Val Thr Gln Asp Ala Glu Asp Arg
1               5                   10                  15

Cys

<210> SEQ ID NO 48
<211> LENGTH: 16
<212> TYPE: PRT
<213> ORGANISM: Homo sapiens
<220> FEATURE:
<221> NAME/KEY: MOD_RES
<222> LOCATION: (1)..(16)
<223> OTHER INFORMATION: PEG2 is linked to the C-terminus via an amide
      bond

<400> SEQUENCE: 48

Tyr Arg Val Arg Phe Leu Arg Lys Glu Asn Thr Gln Asp Ala Glu Asp
1               5                   10                  15

<210> SEQ ID NO 49
<211> LENGTH: 15
<212> TYPE: PRT
<213> ORGANISM: Homo sapiens
<220> FEATURE:
<221> NAME/KEY: MOD_RES
<222> LOCATION: (1)..(15)
<223> OTHER INFORMATION: PEG2 is linked to the C-terminus via an amide
      bond

<400> SEQUENCE: 49

Val Arg Phe Leu Arg Lys Glu Asn Val Thr Gln Asp Ala Glu Asp
1               5                   10                  15

<210> SEQ ID NO 50
<211> LENGTH: 20
<212> TYPE: PRT
<213> ORGANISM: Homo sapiens
<220> FEATURE:
<221> NAME/KEY: MOD_RES
<222> LOCATION: (1)..(20)
<223> OTHER INFORMATION: PEG2 is linked to the N-terminus via an amide
      bond

<400> SEQUENCE: 50

Tyr Arg Val Arg Phe Leu Ala Lys Glu Asn Val Thr Gln Asp Ala Glu
1               5                   10                  15

Asp Arg Cys Thr
            20

<210> SEQ ID NO 51
<211> LENGTH: 20
<212> TYPE: PRT
<213> ORGANISM: Homo sapiens
<220> FEATURE:
<221> NAME/KEY: MOD_RES
<222> LOCATION: (1)..(20)
<223> OTHER INFORMATION: PEG2 is linked to the N-terminus via an amide
      bond

<400> SEQUENCE: 51

Phe Tyr Arg Val Arg Phe Leu Ala Lys Glu Asn Val Thr Gln Asp Arg
```

```
1               5                   10                  15

Glu Asp Asn Cys
            20

<210> SEQ ID NO 52
<211> LENGTH: 20
<212> TYPE: PRT
<213> ORGANISM: Homo sapiens
<220> FEATURE:
<221> NAME/KEY: MOD_RES
<222> LOCATION: (1)..(20)
<223> OTHER INFORMATION: PEG2 is linked to the C-terminus via an amide
      bond

<400> SEQUENCE: 52

Tyr Arg Val Arg Phe Leu Ala Lys Glu Asn Val Thr Gln Asp Ala Glu
1               5                   10                  15

Asp Arg Cys Thr
            20

<210> SEQ ID NO 53
<211> LENGTH: 20
<212> TYPE: PRT
<213> ORGANISM: Homo sapiens
<220> FEATURE:
<221> NAME/KEY: MOD_RES
<222> LOCATION: (1)..(20)
<223> OTHER INFORMATION: PEG2 is linked to the C-terminus via an amide
      bond

<400> SEQUENCE: 53

Phe Tyr Arg Val Arg Phe Leu Ala Lys Glu Asn Val Thr Gln Asp Arg
1               5                   10                  15

Glu Asp Asn Cys
            20

<210> SEQ ID NO 54
<211> LENGTH: 20
<212> TYPE: PRT
<213> ORGANISM: Homo sapiens
<220> FEATURE:
<221> NAME/KEY: MOD_RES
<222> LOCATION: (1)..(20)
<223> OTHER INFORMATION: PEG2 is linked to the C-terminus via an amide
      bond

<400> SEQUENCE: 54

Tyr Arg Val Arg Phe Leu Arg Lys Glu Asn Val Thr Gln Asp Ala Glu
1               5                   10                  15

Asp Asn Thr Cys
            20
```